US012612450B2

(12) United States Patent　　　(10) Patent No.: US 12,612,450 B2
Mond et al.　　　　　　　　　　　　(45) Date of Patent: *Apr. 28, 2026

(54) ANTI-PNEUMOCOCCAL HYPERIMMUNE GLOBULIN FOR THE TREATMENT AND PREVENTION OF PNEUMOCOCCAL INFECTION

(71) Applicant: ADMA BIOMANUFACTURING, LLC, Boca Raton, FL (US)

(72) Inventors: James Mond, Silver Spring, MD (US); Adam S. Grossman, Saddle River, NJ (US)

(73) Assignee: ADMA BIOMANUFACTURING, LLC, Boca Raton, FL (US)

( * ) Notice: Subject to any disclaimer, the term of this patent is extended or adjusted under 35 U.S.C. 154(b) by 89 days.

This patent is subject to a terminal disclaimer.

(21) Appl. No.: 18/438,693

(22) Filed: Feb. 12, 2024

(65) Prior Publication Data

US 2024/0262896 A1　　Aug. 8, 2024

Related U.S. Application Data

(63) Continuation of application No. 17/397,915, filed on Aug. 9, 2021, now Pat. No. 11,897,943, which is a
(Continued)

(51) Int. Cl.
C07K 16/12　　　(2006.01)
A61K 9/00　　　　(2006.01)
(Continued)

(52) U.S. Cl.
CPC ........ *C07K 16/1275* (2013.01); *A61K 9/0019* (2013.01); *A61K 35/16* (2013.01);
(Continued)

(58) Field of Classification Search
CPC .. C07K 16/1275; C07K 16/06; C07K 16/065; C07K 2317/10; C07K 2317/21;
(Continued)

(56) References Cited

U.S. PATENT DOCUMENTS 4,021,540　A　　5/1977　Pollack et al.
4,174,388　A　　11/1979　McAleer et al.
(Continued)

FOREIGN PATENT DOCUMENTS

AU　　　　692678　　　3/1996
AU　　2002368447　　6/2004
(Continued)

OTHER PUBLICATIONS

Romero-Steiner et al., (Clin Vaccine Immunol. Feb. 2006; 13(2): 165-169). (Year: 2006).*
(Continued)

*Primary Examiner* — Jana A Hines
(74) *Attorney, Agent, or Firm* — Tyler Sisk; Casimir Jones SC

(57)　　　　　　　ABSTRACT

The present invention relates to compositions and methods for the treatment of infection caused by *Streptococcus pneumonia*. In particular, the invention provides human hyperimmune globulin and compositions thereof for preventing or treating pneumococcal infection. The invention provides methods of producing hyperimmune globulin containing high titers of opsonophagocytic anti-pneumococcal antibodies, compositions containing same, and methods of using the compositions for the prevention and treatment of pneumococcal infection. The invention further provides methods of preventing or treating pneumococcal infection (e.g., upper respiratory infections (e.g., bronchitis, otitis, sinusitis, etc.)) in immunocompromised subjects via administration of hyperimmune globulin compositions of the
(Continued)

Pneumococcal serotype specific IgG Concentrations in individual donor sera drawn at different time points

| Donor ID | Time Point | Sample ID | Serotype specific IgG concentration (µg/mL) | | | | | | | | | | | |
|---|---|---|---|---|---|---|---|---|---|---|---|---|---|---|
| | | | 1 | 3 | 4 | 5 | 6B | 7F | 9V | 14 | 18C | 19A | 19F | 23F |
| Donor #34443 | Pre | 1010183980 | 2.14 | 0.13 | 0.19 | 0.57 | 0.15 | 0.81 | 0.04 | 0.65 | 0.57 | 0.25 | 1.19 | 1.29 |
| | Week 4 | 1010187977 | 1086.8 | 2.12 | 28.50 | 3.24 | 4.56 | 12.82 | 10.27 | 0.56 | 10.12 | 23.76 | 166.82 | 56.74 |
| | Week 8 | 1010191870 | 683.56 | 1.04 | 18.37 | 1.72 | 2.57 | 8.75 | 7.14 | 0.39 | 5.55 | 14.62 | 99.79 | 35.07 |
| | Week 10 | 1010193841 | 894.33 | 2.85 | 27.24 | 2.74 | 2.80 | 12.26 | 8.92 | 0.66 | 7.88 | 18.69 | 118.51 | 51.77 |
| | Week 12 | 1010193848 | 814.20 | 2.30 | 22.37 | 2.68 | 2.60 | 12.29 | 8.07 | 0.65 | 7.30 | 16.70 | 143.87 | 45.81 |
| | Week 16 | 1010199412 | 632.08 | 1.90 | 19.35 | 2.32 | 2.21 | 10.83 | 6.47 | 0.81 | 6.71 | 15.16 | 103.09 | 39.97 |
| Donor #7942 | Pre | 1010184203 | 0.52 | 0.32 | <LOD | 0.39 | 0.24 | 0.14 | 0.03 | <LOD | <LOD | 0.18 | <LOD | 0.36 |
| | Week 4 | 1010187944 | 36.04 | 15.09 | 3.49 | 2.54 | 0.28 | 4.95 | 9.76 | 3.14 | 23.07 | 3.40 | 0.17 | 1.43 |
| | Week 8 | 1010191587 | 33.01 | 10.17 | 5.92 | 2.35 | 0.27 | 2.85 | 8.91 | 3.23 | 19.45 | 2.11 | 0.24 | 1.63 |
| | Week 10 | 1010193786 | 31.93 | 10.72 | 6.50 | 2.78 | 0.49 | 2.66 | 7.64 | 3.29 | 15.99 | 5.54 | 0.35 | 1.57 |
| | Week 12 | 1010195777 | 26.03 | 8.66 | 5.42 | 2.82 | 0.48 | 2.33 | 6.99 | 3.18 | 14.71 | 6.28 | 0.39 | 1.62 |
| | Week 16 | 1010200569 | 15.36 | 5.78 | 3.98 | 2.72 | 0.56 | 1.69 | 5.70 | 2.96 | 11.31 | 6.72 | 0.54 | 1.83 |
| Donor #20063 | Pre | 1010184756 | 0.44 | 1.00 | <LOD | 13.52 | 3.90 | 1.26 | 0.68 | 2.38 | 1.17 | 6.54 | 17.69 | 2.85 |
| | Week 4 | 1010188381 | 0.72 | 3.12 | 1.16 | 90.54 | 19.40 | 16.61 | 0.93 | 5.47 | 39.95 | 8.65 | 23.85 | 8.03 |
| | Week 8 | 1010192069 | 0.76 | 2.48 | 1.06 | 84.87 | 8.83 | 9.42 | 11.78 | 4.34 | 27.09 | 9.24 | 23.12 | 7.03 |
| | Week 10 | 1010193932 | 1.05 | 3.18 | 1.85 | 216.25 | 8.50 | 8.98 | 1.04 | 4.13 | 30.70 | 8.41 | 17.11 | 7.26 |
| | Week 12 | 1010195963 | 1.08 | 2.49 | 1.49 | 251.97 | 6.82 | 5.63 | 0.99 | 3.87 | 20.26 | 6.96 | 14.72 | 5.80 |
| | Week 16 | 1010260933 | 1.03 | 2.34 | 1.24 | 268.43 | 6.96 | 3.93 | 1.05 | 3.18 | 14.30 | 6.92 | 13.96 | 4.38 |
| Donor #1892 | Pre | 1010184804 | 0.13 | <LOD | <LOD | 0.19 | <LOD | 0.04 | <LOD | <LOD | <LOD | <LOD | 0.06 | <LOD |
| | Week 4 | 1010188291 | 22.50 | 1.98 | 0.59 | 0.52 | 6.37 | 41.00 | 1.25 | 0.49 | 18.30 | 3.92 | 1.59 | 1.98 |
| | Week 8 | 1010192199 | 9.75 | 6.93 | 0.21 | 0.50 | 0.10 | 19.40 | 0.59 | 0.15 | 6.91 | 2.52 | 0.37 | 1.27 |
| | Week 10 | 1010194156 | 6.67 | 1.40 | 0.20 | 0.85 | 0.14 | 11.42 | 0.69 | 0.21 | 4.55 | 1.91 | 0.59 | 1.21 | invention (e.g., containing a high titer of opsonophagocytic anti-pneumococcal antibodies) to immunocompromised subjects.

19 Claims, 25 Drawing Sheets

Related U.S. Application Data continuation of application No. 16/384,334, filed on Apr. 15, 2019, now Pat. No. 11,084,870, which is a continuation of application No. 15/460,147, filed on Mar. 15, 2017, now Pat. No. 10,259,865.

(51) Int. Cl.
| | |
|---|---|
| *A61K 35/16* | (2015.01) |
| *C07K 16/06* | (2006.01) |
| *C07K 16/1275* | (2026.01) |

(52) U.S. Cl.
CPC ............ *C07K 16/06* (2013.01); *C07K 16/065* (2013.01); *C07K 2317/10* (2013.01); *C07K 2317/21* (2013.01)

(58) Field of Classification Search
CPC .... A61K 9/0019; A61K 35/16; A61K 39/085; A61K 38/16; A61K 31/04; A61K 37/04; A61K 2039/505; A61P 31/04
See application file for complete search history.

(56) References Cited

U.S. PATENT DOCUMENTS

| | | | |
|---|---|---|---|
| 4,185,084 A | 1/1980 | Mochida et al. |
| 4,256,631 A | 3/1981 | Yokoo et al. |
| 4,305,870 A | 12/1981 | Liu et al. |
| 4,308,026 A | 12/1981 | Mochida et al. |
| 4,318,902 A | 3/1982 | Stephan |
| 4,346,073 A | 8/1982 | Aronson et al. |
| 4,356,170 A | 10/1982 | Jennings et al. |
| 4,376,110 A | 3/1983 | David et al. |
| 4,402,939 A | 9/1983 | Fournier |
| 4,482,483 A | 11/1984 | Curry et al. |
| 4,486,530 A | 12/1984 | David et al. |
| 4,587,121 A | 5/1986 | Collins et al. |
| 4,617,379 A | 10/1986 | Dobkin et al. |
| 4,659,563 A | 4/1987 | Dobkin |
| 4,665,159 A | 5/1987 | Dobkin |
| 4,717,564 A | 1/1988 | Dobkin |
| 4,717,766 A | 1/1988 | Dobkin |
| 4,800,078 A | 1/1989 | Prince et al. |
| 4,801,450 A | 1/1989 | Collins et al. |
| 4,863,730 A | 9/1989 | Karpas |
| 5,075,425 A | 12/1991 | Kotitschke et al. |
| 5,138,034 A | 8/1992 | Uemura et al. |
| 5,360,897 A | 11/1994 | Anderson et al. |
| 5,412,077 A | 5/1995 | Siber et al. |
| 5,455,032 A | 10/1995 | Kenny et al. |
| 5,505,945 A | 4/1996 | Gristina |
| 5,530,102 A | 6/1996 | Gristina et al. |
| 5,582,827 A | 12/1996 | Siber et al. |
| 5,614,382 A | 3/1997 | Metcalf |
| 5,679,768 A | 10/1997 | Briles et al. |
| 5,728,387 A | 3/1998 | Briles et al. |
| 5,804,193 A | 9/1998 | Briles et al. |
| 5,817,312 A | 10/1998 | Gristina et al. |
| 5,847,112 A | 12/1998 | Kniskern et al. |
| 5,891,438 A | 4/1999 | Silverman |
| 5,945,098 A | 8/1999 | Sarno et al. |
| 5,965,141 A | 10/1999 | Briles et al. |
| 5,985,264 A | 11/1999 | Metzger et al. |
| 6,224,880 B1 | 5/2001 | Chan et al. |
| 6,262,029 B1 | 7/2001 | Press |
| 6,372,216 B1 | 4/2002 | Piazza |
| 6,685,942 B1 | 2/2004 | Burton et al. |
| 6,692,739 B1 | 2/2004 | Patti et al. |
| 6,815,172 B1 | 11/2004 | Martinez et al. |
| 6,818,216 B2 | 11/2004 | Young et al. |
| 6,893,639 B2 | 5/2005 | Levy et al. |
| 6,929,930 B2 | 8/2005 | Choi et al. |
| 6,962,700 B1 | 11/2005 | Pollack |
| 6,984,492 B2 | 1/2006 | Betez et al. |
| 7,045,131 B2 | 5/2006 | Patti et al. |
| 7,070,786 B2 | 7/2006 | Scallon |
| 7,229,619 B1 | 6/2007 | Young et al. |
| 7,323,172 B2 | 1/2008 | Young et al. |
| 7,364,742 B2 | 4/2008 | Scallon |
| 7,488,486 B2 | 2/2009 | Shimoni et al. |
| 7,553,489 B2 | 6/2009 | Young et al. |
| 7,597,891 B2 | 10/2009 | Simon |
| 7,879,331 B2 | 2/2011 | Zurlo et al. |
| 7,879,332 B2 | 2/2011 | Zurlo et al. |
| 8,221,759 B2 | 7/2012 | Pilkington et al. |
| 8,252,546 B2 | 8/2012 | Briles et al. |
| 8,293,242 B2 | 10/2012 | Zurlo et al. |
| 8,354,249 B2 | 1/2013 | Nur et al. |
| 8,546,548 B2 | 10/2013 | Teschner et al. |
| 8,772,462 B2 | 7/2014 | Teschner et al. |
| 8,796,430 B2 | 8/2014 | Bruckschwaiger et al. |
| 8,889,838 B2 | 11/2014 | Teschner et al. |
| 8,921,520 B2 | 12/2014 | Teschner et al. |
| 8,940,877 B2 | 1/2015 | Bruckschwaiger et al. |
| 8,993,734 B2 | 3/2015 | Bruckschwaiger et al. |
| 9,107,906 B1* | 8/2015 | Grossman ......... C07K 16/1271 |
| 9,139,642 B2 | 9/2015 | Williamson et al. |
| 9,175,068 B2 | 11/2015 | Teschner et al. |
| 9,365,635 B2 | 6/2016 | Nur et al. |
| 9,403,900 B2 | 8/2016 | Williamson et al. |
| 9,447,173 B2 | 9/2016 | Gurnett-Bander et al. |
| 9,468,675 B2 | 10/2016 | Teschner et al. |
| 9,708,391 B2 | 7/2017 | Teschner et al. |
| 9,714,283 B2 | 7/2017 | Grossman et al. |
| 9,815,886 B2 | 11/2017 | Grossman et al. |
| 9,969,793 B2 | 5/2018 | Grossman et al. |
| 2001/0051708 A1 | 12/2001 | Laursen |
| 2002/0010428 A1 | 1/2002 | Vedrine et al. |
| 2002/0038111 A1 | 3/2002 | Alchas |
| 2002/0051788 A1 | 5/2002 | Pozsgay |
| 2002/0094338 A1 | 7/2002 | Jonsdottir |
| 2002/0107265 A1 | 8/2002 | Chen |
| 2002/0159997 A1 | 10/2002 | Patti et al. |
| 2003/0099672 A1 | 5/2003 | Schultz |
| 2003/0105307 A1 | 6/2003 | Sampson et al. |
| 2003/0118591 A1 | 6/2003 | Levy |
| 2003/0133929 A1 | 7/2003 | Cham |
| 2003/0147922 A1 | 8/2003 | Capiau et al. |
| 2003/0162260 A1 | 8/2003 | Minion et al. |
| 2004/0047882 A1 | 3/2004 | Broeker |
| 2004/0052804 A1 | 3/2004 | Arumugham et al. |
| 2004/0156857 A1 | 8/2004 | Adalsteinsson et al. |
| 2004/0228879 A1 | 11/2004 | Deschamps et al. |
| 2005/0031646 A1 | 2/2005 | Capiau et al. |
| 2005/0053605 A1 | 3/2005 | Betz et al. |
| 2005/0070876 A1 | 3/2005 | Castellano |
| 2005/0158329 A1 | 7/2005 | Ghosh |
| 2005/0208608 A1 | 9/2005 | Raven |
| 2005/0260694 A1 | 11/2005 | Piasio |
| 2005/0287146 A1 | 12/2005 | Patti et al. |
| 2006/0002961 A1 | 1/2006 | Capiau et al. |
| 2006/0093626 A1 | 5/2006 | Capiau et al. |
| 2006/0110407 A1 | 5/2006 | Stopera et al. |
| 2006/0121059 A1 | 6/2006 | Garcon et al. |
| 2006/0198848 A1 | 9/2006 | Betz et al. |
| 2006/0222651 A1 | 10/2006 | Patti et al. |
| 2007/0009542 A1 | 1/2007 | Levin et al. |
| 2007/0037170 A1 | 2/2007 | Nur et al. |
| 2007/0154492 A1 | 7/2007 | Michon et al. |
| 2007/0161088 A1 | 7/2007 | Arumugham et al. |
| 2007/0231344 A1 | 10/2007 | Leadbetter et al. |
| 2007/0244305 A1 | 10/2007 | Parkkinen |
| 2007/0249550 A1 | 10/2007 | Sitkovsky |
| 2008/0026002 A1 | 1/2008 | Danzig |

(56)                References Cited

U.S. PATENT DOCUMENTS

| | | | |
|---|---|---|---|
| 2008/0066739 A1 | 3/2008 | LeMahieu | |
| 2008/0286838 A1 | 11/2008 | Yuan et al. | |
| 2009/0004218 A1 | 1/2009 | Hacohen et al. | |
| 2009/0010964 A1 | 1/2009 | Grobler et al. | |
| 2009/0028846 A1 | 1/2009 | Miescher et al. | |
| 2009/0047353 A1 | 2/2009 | O'Hagan | |
| 2009/0136547 A1 | 5/2009 | Telford et al. | |
| 2009/0191217 A1 | 7/2009 | de Wildt et al. | |
| 2009/0232798 A1 | 9/2009 | Betz et al. | |
| 2009/0269359 A1 | 10/2009 | Scuderi et al. | |
| 2010/0040601 A1 | 2/2010 | Cantin et al. | |
| 2010/0074922 A1 | 3/2010 | Biemans | |
| 2010/0143394 A1 | 6/2010 | Kasmi et al. | |
| 2010/0266625 A1 | 10/2010 | Tai et al. | |
| 2010/0290996 A1 | 11/2010 | Nickerson et al. | |
| 2011/0020386 A1 | 1/2011 | Gierahn et al. | |
| 2011/0059085 A1 | 3/2011 | Kim | |
| 2012/0027771 A1 | 2/2012 | Cantor | |
| 2012/0121578 A1 | 5/2012 | Block | |
| 2013/0108619 A1 | 5/2013 | Melamed | |
| 2013/0195876 A1 | 8/2013 | Smith | |
| 2014/0322263 A1* | 10/2014 | Siber | A61K 39/02 |
| | | | 424/197.11 |
| 2015/0133644 A1 | 5/2015 | Bruckschwaiger et al. | |
| 2016/0024186 A1 | 1/2016 | Wang | |
| 2016/0114037 A1 | 4/2016 | Grossman et al. | |
| 2016/0145321 A1 | 5/2016 | Wadia et al. | |
| 2016/0145322 A1 | 5/2016 | Wadia et al. | |
| 2016/0194383 A1 | 7/2016 | Williamson et al. | |
| 2016/0244512 A1 | 8/2016 | Teschner et al. | |
| 2017/0029488 A1 | 2/2017 | Gurnett-Bander et al. | |
| 2017/0121394 A1 | 5/2017 | Vora et al. | |

FOREIGN PATENT DOCUMENTS

| | | |
|---|---|---|
| CA | 2472818 | 12/2005 |
| CA | 2749367 | 7/2010 |
| CN | 1241937 | 1/2000 |
| CN | 1899609 | 1/2007 |
| CN | 101024079 | 8/2007 |
| CN | 101130071 | 2/2008 |
| CN | 101374548 | 2/2009 |
| CN | 101590224 | 12/2009 |
| CN | 101785857 | 7/2010 |
| CN | 102068690 | 5/2011 |
| CO | 5210947 | 10/2002 |
| EP | 0035429 | 9/1981 |
| EP | 0161188 | 11/1985 |
| EP | 0168322 | 1/1986 |
| EP | 0186576 | 7/1986 |
| EP | 0208375 | 1/1987 |
| EP | 0378881 | 7/1990 |
| EP | 0383184 | 8/1990 |
| EP | 0399001 | 11/1990 |
| EP | 0427347 | 5/1991 |
| EP | 0449856 | 10/1991 |
| EP | 0471177 | 2/1992 |
| EP | 0477508 | 4/1992 |
| EP | 0497524 | 8/1992 |
| EP | 0497525 | 8/1992 |
| EP | 0571538 | 12/1993 |
| EP | 0622081 | 11/1994 |
| EP | 0625910 | 11/1994 |
| EP | 0720485 | 7/1996 |
| EP | 0778781 | 6/1997 |
| EP | 0831901 | 4/1998 |
| EP | 0848011 | 6/1998 |
| EP | 0877624 | 11/1998 |
| EP | 0894008 | 2/1999 |
| EP | 0969873 | 1/2000 |
| EP | 0971945 | 1/2000 |
| EP | 0977588 | 2/2000 |
| EP | 0983087 | 3/2000 |
| EP | 1015027 | 7/2000 |

| | | |
|---|---|---|
| EP | 1019437 | 7/2000 |
| EP | 1035137 | 9/2000 |
| EP | 1076662 | 2/2001 |
| EP | 1109576 | 6/2001 |
| EP | 1137789 | 10/2001 |
| EP | 1162998 | 12/2001 |
| EP | 1171159 | 1/2002 |
| EP | 1296715 | 4/2003 |
| EP | 1317279 | 6/2003 |
| EP | 1501542 | 2/2005 |
| EP | 1558280 | 8/2005 |
| EP | 1590373 | 11/2005 |
| EP | 1638601 | 3/2006 |
| EP | 1651261 | 5/2006 |
| EP | 1704167 | 9/2006 |
| EP | 1776962 | 4/2007 |
| EP | 1791860 | 6/2007 |
| EP | 1838345 | 10/2007 |
| EP | 1868645 | 12/2007 |
| EP | 1880735 | 1/2008 |
| EP | 1928418 | 6/2008 |
| EP | 1962899 | 9/2008 |
| EP | 2167531 | 3/2010 |
| EP | 2180901 | 5/2010 |
| EP | 2277535 | 1/2011 |
| JP | 2010260849 | 11/2010 |
| JP | 2011057713 | 3/2011 |
| KR | 20110068831 | 6/2011 |
| WO | WO 91/01146 | 2/1991 |
| WO | WO 91/12819 | 9/1991 |
| WO | WO 93/15758 | 8/1993 |
| WO | WO 94/04195 | 3/1994 |
| WO | WO 95/13294 | 5/1995 |
| WO | WO 96/21465 | 7/1996 |
| WO | WO 96/40225 | 12/1996 |
| WO | WO 97/20940 | 6/1997 |
| WO | WO 98/18931 | 5/1998 |
| WO | WO 98/33521 | 8/1998 |
| WO | WO 98/39450 | 9/1998 |
| WO | WO 99/03884 | 1/1999 |
| WO | WO 99/15205 | 4/1999 |
| WO | WO 99/40936 | 8/1999 |
| WO | WO 99/47168 | 9/1999 |
| WO | WO 00/12132 | 3/2000 |
| WO | WO 01/72337 | 3/2000 |
| WO | WO 00/56360 | 9/2000 |
| WO | WO 00/61761 | 10/2000 |
| WO | WO 00/62801 | 10/2000 |
| WO | WO 00/062802 | 10/2000 |
| WO | WO 00/63385 | 10/2000 |
| WO | WO 01/96368 | 12/2001 |
| WO | WO 02/40518 | 5/2002 |
| WO | WO 02/056909 | 7/2002 |
| WO | WO 03/040170 | 5/2003 |
| WO | WO 03/051392 | 6/2003 |
| WO | WO 2004/064864 | 8/2004 |
| WO | WO 2004/097000 | 11/2004 |
| WO | WO 2005/058940 | 6/2005 |
| WO | WO 2005/065382 | 7/2005 |
| WO | WO 2005/070458 | 8/2005 |
| WO | WO 2005/073252 | 8/2005 |
| WO | WO 2005/108580 | 11/2005 |
| WO | WO 2005/120563 | 12/2005 |
| WO | WO 2006/027685 | 3/2006 |
| WO | WO 2006/065137 | 6/2006 |
| WO | WO 2006/084467 | 8/2006 |
| WO | WO 2007/017859 | 2/2007 |
| WO | WO 2007/068907 | 6/2007 |
| WO | WO 2007/071711 | 6/2007 |
| WO | WO 2007/109129 | 9/2007 |
| WO | WO 2007/113598 | 10/2007 |
| WO | WO 2007/116028 | 10/2007 |
| WO | WO 2007/116322 | 10/2007 |
| WO | WO 2007/116409 | 10/2007 |
| WO | WO 2008/021076 | 2/2008 |
| WO | WO 2008/081014 | 7/2008 |
| WO | WO 2008/081022 | 7/2008 |
| WO | WO 2008/102173 | 8/2008 |
| WO | WO 2008/119358 | 10/2008 |

(56)                    References Cited

FOREIGN PATENT DOCUMENTS

| WO | WO 2008/157590 | 12/2008 |
|----|----------------|---------|
| WO | WO 2009/000826 | 12/2008 |
| WO | WO 2009/016515 | 2/2009 |
| WO | WO 2009/076158 | 6/2009 |
| WO | WO 2009/106085 | 9/2009 |
| WO | WO 2009/143413 | 11/2009 |
| WO | WO 2010/015701 | 2/2010 |
| WO | WO 2010/064243 | 6/2010 |
| WO | WO 2010/094720 | 8/2010 |
| WO | WO 2010/109324 | 9/2010 |
| WO | WO 2010/109325 | 9/2010 |
| WO | WO 2010/141312 | 12/2010 |
| WO | WO 2010/150242 | 12/2010 |
| WO | WO 2011/031893 | 3/2011 |
| WO | WO 2011/041691 | 4/2011 |
| WO | WO 2011/067758 | 6/2011 |
| WO | WO 2011/080595 | 7/2011 |
| WO | WO 2011/103588 | 8/2011 |
| WO | WO 2011/110241 | 9/2011 |
| WO | WO 2011/110531 | 9/2011 |
| WO | WO 2013/071267 | 5/2013 |
| WO | WO 2013/115962 | 8/2013 |
| WO | WO 2016/069693 | 5/2016 |

OTHER PUBLICATIONS

Adler, S. P., & Nigro, G. (2009). Findings and conclusions from CMV hyperimmune globulin treatment trials. Journal of Clinical Virology, 46, S54-S57.

Alejandria, M. M., Lansang, M. A. D., Dans, L. F., & Mantaring III, J. B. (2013). Intravenous immunoglobulin for treating sepsis, severe sepsis and septic shock. The Cochrane Library., full document.

Aschermann, S., Lux, A., Baerenwaldt, A., Biburger, M., & Nimmerjahn, F. (2010). The other side of immunoglobulin G: suppressor of inflammation. Clinical & Experimental Immunology, 160(2), 161-167.

Balmer et al., Anti-pneumococcal antibody titre measurement: what useful information does it yield? J Clin Pathol., 2006;60(4):345-350.

Balmer et al., Measurement and interpretation of pneumococcal IgG levels for clinical management, Clin Exp Immunol. Sep. 2003;133(3):364-9.

Ben-Nathan, D., Gershoni-Yahalom, O., Samina, I., Khinich, Y., Nur, I., Laub, O., . . . & Orr, N. (2009). Using high titer West Nile intravenous immunoglobulin from selected Israeli donors for treatment of West Nile virus infection. BMC infectious diseases, 9(1), 18.

Bhakdi, S. U. C. H. A. R. I. T., Mannhardt, U., Muhly, M., Hugo, F., Ronneberger, H., & Hungerer, K. D. (1989). Human hyperimmune globulin protects against the cytotoxic action of staphylococcal alpha-toxin in vitro and in vivo. Infection and immunity, 57(10), 3214-3220.

Boukhvalova et al, Treatment with 1-15 C97K novel RSV Ig RI-992 controls viral A61K replication and reduces pulmonary damage in Unocompromised Sigmodon hispidus, Bone Marrow Transplantation, vol. 1, No. 1, Sep. 14, 2015 (2015-99-14), pp. 119-126.

Brandtzaeg, P. (2009). Mucosal immunity: induction, dissemination, and effector functions. Scandinavian journal of immunology, 70(6), 505-515.

Buchacher, Purification of intravenous immunoglobulin G from human plasma—aspects of yield and virus safety, Biotechnol. J., 1, pp. 148-163, 2006.

Buehring et al., Chronic sinusitis refractory to standard management in patients with humoral immunodeficiencies, Clin Exp Immunol 1997, 109:468-472.

Busse, P. J., Razvi, S., & Cunningham-Rundles, C. (2002). Efficacy of intravenous immunoglobulin in the prevention of pneumonia in patients with common variable immunodeficiency. Journal of Allergy and Clinical Immunology, 109(6), 1001-1004.

Casadevall, A., & Scharff, M. D. (1994). Serum therapy revisited: animal models of infection and development of passive antibody therapy. Antimicrobial agents and chemotherapy, 38(8), 1695-1702.

Casadevall, A., Dadachova, E., & Pirofski, L. A. (2004). Passive antibody therapy for infectious diseases. Nature Reviews Microbiology, 2(9), 695-703.

Casal, J., Aguilar, L., Jado, I., Yuste, J., Giménez, M. J., Prieto, J., & Fenoll, A. (2002). Effects of specific antibodies against Streptococcus pneumoniae on pharmacodynamic parameters of β-lactams in a mouse sepsis model. Antimicrobial agents and chemotherapy, 46(5), 1340-1344.

Clark, L. A., & Easmon, C. S. (1986). Opsonic activity of intravenous immunoglobulin preparations against Staphylococcus epidermidis. Journal of clinical pathology, 39(8), 856-860.

Cohn et al., Preparation and properties of serum and plasma proteins; a system for the separation into fractions of the protein and lipoprotein components of biological tissues and fluids, J Am Chem Soc, 62, 459-475 (1946).

Cortez, K., Murphy, B. R., Almeida, K. N., Beeler, J., Levandowski, R. A., Gill, V. J., . . . & Bennett, J. E. (2002). Immune-globulin prophylaxis of respiratory syncytial virus infection in patients undergoing stem-cell transplantation. The Journal of infectious diseases, 186(6), 834-838.

Corthesy, Recombinant secretory IgA for immune intervention against mucosal pathogens, Biochem. Soc. Trans. 1997; 25:471-475.

Crottet et al., Expression, purification and biochemical characterization of recombinant murine secretory component: a novel tool in mucosal immunology, Biochem. J. 1999; 341:299-306.

De Hennezel, L., Ramisse, F., Binder, P., Marchal, G., & Alonso, J. M. (2001). Effective combination therapy for invasive pneumococcal pneumonia with ampicillin and intravenous immunoglobulins in a mouse model. Antimicrobial agents and chemotherapy, 45(1), 316-318.

Devincenzo et al, Respiratory syncytial virus immune globulin treatment of lower respiratory tract infection in pediatric patients undergoing bone marrow transplantation—a compassionate use experience, Bone Marrow Transplantation, vol. 25, No. 2, Jan. 1, 2000 (2090-91-91), pp. 161-165.

Dorner et al., At what stage should virus inactivation be carried out?, Dev Biol Stand 1993 vol 81, pp. 137-143.

European Search Report of co-pending European patent application No. 15190963.7 dated May 3, 2016, 10 pages.

European Search Report of co-pending European patent application No. 18161907 dated Jun. 19, 2018, 11 pages.

Falsey et al, A Summary of the Study of a Polyclonal Human IVIG with A Standardized High-Levels of RSV Neutralizing Antibodies, IDSA International Conference, Aug. 21, 2013.

Falsey et al., Acute respiratory tract infection in daycare centers for older persons, J Am Geriatr Soc. 1995;43:30-36.

Falsey et al., Human metapneumovirus infections in young and elderly adults, J Infect Dis. 2003;187:785-790.

Falsey et al., The "common cold" in frail older persons: impact of rhinovirus and coronavirus in a senior daycare center, J Am Geriatr Soc. 1997;45:706-711.

Falsey et al., Viral respiratory infections in the institutionalized elderly: clinical and epidemiologic findings, J Am Geriat Soc. 1992;40:115-119.

Favre et al., Intravenous immunoglobulin replacement prevents severe and lower respiratory tract infections, but not upper respiratory tract and non-respiratory infections in common variable immune deficiency, Allergy 2005 60:385-390.

Fischer, L., Gerstel, P. F., Poncet, A., Siegrist, C. A., Laffitte, E., Gabay, C., . . . & Ribi, C. (2015). Pneumococcal polysaccharide vaccination in adults undergoing immunosuppressive treatment for inflammatory diseases—a longitudinal study. Arthritis research & therapy, 17(1), 151.

Fried, A. J., & Bonilla, F. A. (2009). Pathogenesis, diagnosis, and management of primary antibody deficiencies and infections. Clinical microbiology reviews, 22(3), 396-414.

Gelfand, Clinical uses of intravenous immunoglobulin continue to expand, Medscape Allergy & Immunology, 2004, pp. 1-4.

(56) References Cited

OTHER PUBLICATIONS

Goldblatt et al., The immunogenicity of 7-valent pneumococcal conjugate vaccine versus 23-valent polysaccharide vaccine in adults aged 50-80 years. Clin Infect Dis. Nov. 1, 2009;49(9):1318-25.

Hamill et al., IgG Antibody Reactive with Five Serotypes of *Streptococcus pneumoniae* in Commercial Intravenous Immunoglobulin Preparations, The Journal of Infectious Diseases, vol. 166, No. 1 (Jul. 1992), pp. 38-42.

Hemming, V. G., Prince, G. A., Groothuis, J. R., & Siber, G. R. (1995). Hyperimmune globulins in prevention and treatment of respiratory syncytial virus infections. Clinical microbiology reviews, 8(1), 22-33.

Hopkins, Clinical Efficacy of Intramuscular Vaccinia Immune Globulin: A Literature Review, Clinical Infectious Diseases, 39, pp. 819-826, 2004.

Hügler, P., Siebrecht, P., Hoffmann, K., Stücker, M., Windeler, J., Altmeyer, P., & Laubenthal, H. (2002). Prevention of postherpetic neuralgia with varicella-zoster hyperimmune globulin. European journal of pain, 6(6), 435-445.

International Search Report and Written Opinion for PCT/US2018/022701, mailed Jul. 10, 2018, 10 pages.

Ishizaka, A., Sakiyama, Y., Otsu, M., Ozutsumi, K., & Matsumoto, S. (1994). Successful intravenous immunoglobulin therapy for recurrent pneumococcal otitis media in young children. European journal of pediatrics, 153(3), 174-178.

Iwata et al., Immunogenicity and safety of the 10-valent pneumococcal nontypeable Haemophilus influenzae protein D conjugate vaccine (PHiD-CV) co-administered with DTPa vaccine in Japanese children: A randomized, controlled study. Hum Vaccin Immunother. 2015;11(4):826-37.

Jones et al., Controlled trial of Pseudomonas immunoglobulin and vaccine in burn patients, Lancet. Dec. 13, 1980;2(8207):1263-5.

Keller and Stiehm, Passive Immunity in Prevention and Treatment of Infectious Diseases, Clin. Microbiol. Rev. 2000, 13(4): pp. 602-614.

Kim et al., Opsonophagocytic Antibodies to Serotype Ia, Ib, and III Group B *Streptococcus* among Korean Infants and in Intravenous Immunoglobulin Products. J Korean Med Sci. May 2017;32(5):737-743.

Kudoyarova-Zubavichene, N. M., Sergeyev, N. N., Chepurnov, A. A., & Netesov, S. V. (1999). Preparation and use of hyperimmune serum for prophylaxis and therapy of Ebola virus infections. Journal of Infectious Diseases, 179(Supplement 1), S218-S223.

Lake, J. R. (2008). Do we really need long-term hepatitis B hyperimmune globulin? What are the alternatives?. Liver Transplantation, 14(S2), S23-S26.

Lal, G., Balmer, P., Stanford, E., Martin, S., Warrington, R., & Borrow, R. (2005). Development and validation of a nonaplex assay for the simultaneous quantitation of antibodies to nine *Streptococcus pneumoniae* serotypes. Journal of immunological methods, 296(1), 135-147.

Laupland, K. B., Kirkpatrick, A. W., & Delaney, A. (2007). Polyclonal intravenous immunoglobulin for the treatment of severe sepsis and septic shock in critically ill adults: a systematic review and meta-analysis. Critical care medicine, 35(12), 2686-2692.

Lejtenyi, D., & Mazer, B. (2008). Consistency of protective antibody levels across lots of intravenous immunoglobulin preparations. Journal of Allergy and Clinical Immunology, 121(1), 254-255.

Lullau et al., Antigen binding properties of purified immunoglobulin A and reconstituted secretory immunoglobulin A antibodies, J. Biol. Chem. 1996; 271:16300-16309.

Martin, Remington's Pharmaceutical Sciences, 15th Ed., Mack Publ. Co., Easton, Pa. (1975).

Martinez et al., A Flow Cytometric Opsonophagocytic Assay for Measurement of Functional Antibodies Elicted after Vaccination with the 23-Valent Pneumococcal Polysaccharide Vaccine. Clin Diagnostic Lab Immunol., 1999;6(4):581-6.

Meijvis, S. C. A., Grutters, J. C., Thijsen, S. F., Rijkers, G. T., Biesma, D. H., & Endeman, H. (2011). therapy in pneumonia: what is beyond antibiotics?. Arterial and venous thrombosis: more in common than previously thought, 21.

Miernyk et al., Immunogenicity and Reactogenicity of Pneumococcal Polysaccharide and Conjugate Vaccines in Alaska Native Adults 55-70 Years of Age. Clinical Infections Diseases Jul. 2009;49(2)241-248.

Mikolajczyk, M. G., Concepcion, N. F., Wang, T., Frazier, D., Golding, B., Frasch, C. E., & Scott, D. E. (2004). Characterization of antibodies to capsular polysaccharide antigens of Haemophilus influenzae type b and *Streptococcus pneumoniae* in human immune globulin intravenous preparations. Clinical and diagnostic laboratory immunology, 11(6), 1158-1164.

Mikolajczyk et al., Characterization of antibodies to capsular polysaccharide antigens of Haemophilus influenzae type b and *Streptococcus pneumoniae* in human immune globulin intravenous preparations. Clinical and diagnostic laboratory immunology, (2004). 11(6), 1158-1164.

Mofenson et al.,Intravenous immune globulin for the prevention of bacterial infections in children with symptomatic human immunodeficiency virus infection. The National Institute of Child Health and Human Developments Intravenous Immunoglobulin Study Group, The New England Journal of Medicine, Jul. 11, 1991, vol. 325, No. 2, pp. 73-80.

Murphy, B. R., Prince, G. A., Walsh, E. E., Kim, H. W., Parrott, R. H., Hemming, V. G., . . . & Chanock, R. M. (1986). Dissociation between serum neutralizing and glycoprotein antibody responses of infants and children who received inactivated respiratory syncytial virus vaccine. Journal of clinical microbiology, 24(2), 197-202.

Nation, N. S., Pierce, N. F., Adler, S. J., Chinnock, R. F., & Wehrle, P. F. (1963). Tetanus—the use of human hyperimmune globulin in treatment. California medicine, 98(6), 305.

Navarrete-Navarro, S., Aguilar-Setien, A., Avila-Figueroa, C., Hernández-Sierra, F., & Santos-Preciado, J. I. (1999). Improved serological response to human diploid cell rabies vaccine when given simultaneously with antirabies hyperimmune globulin. Archives of medical research, 30(4), 332-337.

Nimmerjahn, F., & Ravetch, J. V. (2008). Anti-inflammatory actions of intravenous immunoglobulin. Annu. Rev. Immunol., 26, 513-533.

Oncely, J. L. et al., The Separation of the Antibodies, Isoagglutinins, Prothrombin, Plasminogen and B1-Lipoprotein into subfractions of human plasma, J. Am Chem Soc. 71:541-550 (1949).

Orange et al., Therapeutic Immunoglobulin Selected for High Antibody Titer to RSV also Contains High Antibody Titers to Other Respiratory Viruses, Frontiers in Immunology, vol. 6, Aug. 28, 2015 (2915-98-28), pp. 1-7.

Orange, J. S., Hossny, E. M., Weiler, C. R., Ballow, M., Berger, M., Bonilla, F. A., . . . & Nelson Jr, R. P. (2006). Primary Immunodeficiency Committee of the American Academy of Allergy, Asthma and Immunology. Use of intravenous immunoglobulin in human disease: a review of evidence by members of the Primary Immunodeficiency Committee of the American Academy of Allergy, Asthma and Immunology. J Allergy Clin Immunol, 117(4 Suppl), S525-S553.

Ottolini, M. G., Porter, D. D., Hemming, V. G., Zimmerman, M. N., Schwab, N. M., & Prince, G. A. (1999). Effectiveness of RSVIG prophylaxis and therapy of respiratory syncytial virus in an immunosuppressed animal model. Bone marrow transplantation, 24(1), 41-45.

Paris, K., & Sorensen, R. U. (2007). Assessment and clinical interpretation of polysaccharide antibody responses. Annals of Allergy, Asthma & Immunology, 99(5), 462-464.

Ramakrishna et al., Passively administered pooled human immunoglobulins exert IL-10 dependent anti-inflammatory effects that protect against fatal HSV encephalitis, Plos Pathogens. 2011. 7:6:e1002071.

Ramisse et al., Passive and active immunotherapy for experimental pneumococcal pneumonia by polyvalent human immunoglobulin or F(ab')2 fragments administered intranasally. J Infect Dis. May 1996;173(5):1123-8.

Roe, E. A., Jones, R. J., & Dyster, R. E. (1986). Passive immunization of mice against Klebsiella aerogenes. British journal of experimental pathology, 67(1), 25-32.

(56) References Cited

OTHER PUBLICATIONS

Romero-Steiner et al., Multilaboratory Evaluation of a Viability Assay for Measurement of Opsonophagocytic Antibodies Specific to the Capsular Polysaccharides of *Streptococcus pneumoniae*. Clin Diagn Lab Immunol. Nov. 2003;10(6):1019-24.

Romero-Steiner et al., Standardization of an opsonophagocytic assay for the measurement of functional antibody activity against *Streptococcus pneumoniae* using differentiated HL-60 cells, 1997 Clin Diagn Lab Immunol. Jul;4(4):415-22.

Rudrawar, Novel sialic acid derivatives lock open the 150-loop of an influenza A virus group-1 sialidase, Nature Communications, 1(113), 2010.

Salehzadeh et al., Evaluation of Immunoglobulin Levels and Infection Rate in Patients with Common Variable Immunodeficiency After Immunoglobulin Replacement Therapy, J Microbiol Immunol Infect 2010, 43(1):11-17.

Schwab, IVIg-mediated amelioration of ITP in mice is dependent on sialic acid and SIGNR1, Eur. J. Immunol., 42, pp. 826-830, 2012.

Scott et al., Phase 1 trial of a 13-valent pneumococcal conjugate vaccine in healthy adults. Vaccine. Aug. 14, 2007;25(33):6164-6.

Shurin et al., Bacterial polysaccharide immune globulin for prophylaxis of acute otitis media in high-risk children, The Journal of Pediatrics, Nov. 1993, pp. 801-810.

Siber George R. et al, Comparison of antibody concentrations and protective activity of respiratory syncytial virus A immune globulin and conventional immune globulin, Journal of Infectious Diseases. JID, University of Chicago Press, Chicago, IL, vol. 169, No. 6, Jan. 1, 1994 (1994-81-81), pp. 1368-1373.

Siber, G. R., Ambrosino, D. M., McIver, J., Ervin, T. J., Schiffman, G., Sallan, S., & Grady, G. F. (1984). Preparation of human hyperimmune globulin to Haemophilus influenzae b, *Streptococcus pneumoniae*, and Neisseria meningitidis. Infection and immunity, 45(1), 248-254.

Siber, G. R., Leszczynski, J., Pena-Cruz, V., Ferren-Gardner, C., Anderson, R., Hemming, V. G., . . . & Anderson, L. J. (1992). Protective activity of a human respiratory syncytial virus immune globulin prepared from donors screened by microneutralization assay. Journal of Infectious Diseases, 165(3), 456-463.

Simao-Gurge et al., Prospective evaluation of *Streptococcus pneumoniaeserum* antibodies in patients with primaryimmunodeficiency on regular intravenousimmunoglobulin treatment, Allergo Immnopathol 2017, 45: 55-62.

Simoes et al., Respiratory syncytial virus-enriched globulin for the prevention of acute otitis media in high-risk children, Journal of Pediatrics v 129, No. 2, pp. 214-219, 1996.

Spiekermann, G. M., Finn, P. W., Ward, E. S., Dumont, J., Dickinson, B. L., Blumberg, R. S., & Lencer, W. I. (2002). Receptor-mediated immunoglobulin G transport across mucosal barriers in adult life. Journal of Experimental Medicine, 196(3), 303-310.

Stiehm, Standard and special human immune serum globulins as therapeutic agents, Pediatrics, vol. 63, No. 1, 301-319 (1979).

Stott, E. J. et al., Respiratory syncytial virus. Brief review, Archives of Virology, 84:1-52 (1985).

Tanaka, High quality human immunoglobulin G purified from Cohn fractions by liquid chromatography, Brazilian Journal of Medical and Biological Research, 33: 27-30, 2000.

Teschner et al., A new liquid, intravenous immunoglobulin product (IGIV 10%) highly purified by a state-of-the-art process, Vox Sang. Jan. 2007;92(1):42-55.

Tijssen, P., Laboratory Techniques in Biochemistry and Molecular Biology: Practice and Theory of Enzyme Immunoassays, (Burdon & van Knippenberg eds., 3rd ed., 1985) Elsevier, New York.

Tuerlinckx, D., Florkin, B., Ferster, A., De Schutter, I., Chantrain, C., Haerynck, F., . . . & Laub, R. (2014). Pneumococcal antibody levels in children with PID receiving immunoglobulin. Pediatrics, 133(1), e154-e162.

US FDA standards for immune globulin preparation (37 CFR §§640.100; 640.101; 640.102; 640.103; and 640.104, Apr. 1, 2013).

Westerman, L. E., McClure, H. M., Jiang, B., Almond, J. W., & Glass, R. I. (2005). Serum IgG mediates mucosal immunity against rotavirus infection. Proceedings of the National Academy of Sciences of the United States of America, 102(20), 7268-7273.

World Health Organization. (2007). Pneumococcal conjugate vaccine for childhood immunization, WHO position paper. Wkly Epidemiol Rec, 82(12), 93-104.

World Intellectual Property Organization, Patent Landscape Report on Vaccines for Selected Infectious Diseases, 2012.

Wu et al., Immunoprophylaxis of RSV Infection: Advancing from RSV-IGIV to Palivizumab and Motavizumab, Curr Topics Microbiol Immunol. vol. 317, pp. 103-123, 2008.

Yoshida, M., Claypool, S. M., Wagner, J. S., Mizoguchi, E., Mizoguchi, A., Roopenian, D. C., . . . & Blumberg, R. S. (2004). Human neonatal Fc receptor mediates transport of IgG into luminal secretions for delivery of antigens to mucosal dendritic cells. Immunity, 20(6), 769-783.

Zaia et al., A practical method for preparation of varicella-zoster immune globulin, The Journal of Infectious Diseases, vol. 137, No. 5, 601-604 (1978).

European Patent Office, Extended European Search Report for European Application No. 21212658.5 mailed Jun. 13, 2022.

Cordonnier C et al: "Relationship between IgG titers and opsonocytophagocytic activity of anti-pneumococcal antibodies after immunization with the 7-valent conjugate vaccine in allogeneic stem cell transplant", Bone Marrow Transplantation, Nature Publishing Group, GB, vol. 45, No. 9, Dec. 21, 2009 (Dec. 21, 2009), pp. 1423-1426, XP037761143 ISSN: 0268-3369, DO1: 10.1038/BMT.2009.

* cited by examiner

FIG. 1

Pneumococcal serotype specific IgG Concentrations in individual donor sera drawn at different time points

| Donor ID | Time Point | Sample ID | Serotype specific IgG concentration (µg/mL) | | | | | | | | | | | |
|---|---|---|---|---|---|---|---|---|---|---|---|---|---|---|
| | | | 1 | 3 | 4 | 5 | 6B | 7F | 9V | 14 | 18C | 19A | 19F | 23F |
| Donor #34440 | Pre | 1010183980 | 2.14 | 0.13 | 0.19 | 0.57 | 0.15 | 0.81 | 0.04 | 0.65 | 0.57 | 0.25 | 1.10 | 1.29 |
| | Week 4 | 1010187977 | 1086.8 | 2.12 | 28.50 | 3.24 | 4.56 | 12.82 | 10.27 | 0.56 | 10.12 | 23.76 | 166.82 | 56.74 |
| | Week 8 | 1010191870 | 683.56 | 1.04 | 18.37 | 1.72 | 2.57 | 8.75 | 7.14 | 0.39 | 5.55 | 14.62 | 99.79 | 35.07 |
| | Week 10 | 1010193841 | 894.33 | 2.85 | 27.24 | 2.74 | 2.80 | 12.26 | 8.92 | 0.66 | 7.88 | 18.69 | 118.51 | 51.77 |
| | Week 12 | 1010195848 | 814.20 | 2.30 | 22.37 | 2.58 | 2.60 | 12.29 | 8.07 | 0.65 | 7.30 | 16.70 | 143.87 | 45.81 |
| | Week 16 | 1010199412 | 632.08 | 1.90 | 19.35 | 2.32 | 2.21 | 10.83 | 6.47 | 0.81 | 6.71 | 15.16 | 103.09 | 39.97 |
| Donor #7942 | Pre | 1010184203 | 0.52 | 0.32 | <LOD | 0.39 | 0.24 | 0.14 | 0.03 | <LOD | <LOD | 0.18 | <LOD | 0.36 |
| | Week 4 | 1010187944 | 36.04 | 15.06 | 5.49 | 2.54 | 0.28 | 4.95 | 9.76 | 3.14 | 23.07 | 3.40 | 0.17 | 1.43 |
| | Week 8 | 1010191587 | 33.01 | 10.17 | 3.92 | 2.35 | 0.27 | 2.85 | 8.91 | 3.23 | 19.45 | 2.11 | 0.24 | 1.63 |
| | Week 10 | 1010193786 | 31.43 | 10.72 | 6.50 | 2.78 | 0.49 | 2.66 | 7.64 | 3.29 | 15.90 | 5.54 | 0.35 | 1.57 |
| | Week 12 | 1010195777 | 26.03 | 8.66 | 5.42 | 2.82 | 0.48 | 2.22 | 6.99 | 3.18 | 14.71 | 6.26 | 0.30 | 1.62 |
| | Week 16 | 1010200569 | 18.36 | 5.78 | 3.98 | 2.72 | 0.56 | 1.69 | 5.70 | 2.96 | 11.31 | 6.72 | 0.54 | 1.83 |
| Donor #20003 | Pre | 1010184756 | 0.44 | 1.00 | <LOD | 13.52 | 3.90 | 1.26 | 0.68 | 2.38 | 1.17 | 6.54 | 17.69 | 2.85 |
| | Week 4 | 1010188381 | 0.72 | 3.12 | 1.16 | 90.54 | 10.40 | 16.61 | 0.93 | 5.47 | 39.95 | 8.65 | 23.85 | 8.03 |
| | Week 8 | 1010192000 | 0.76 | 2.48 | 1.06 | 84.87 | 8.83 | 9.42 | 0.78 | 4.34 | 27.09 | 9.24 | 23.12 | 7.03 |
| | Week 10 | 1010193932 | 1.05 | 3.18 | 1.85 | 216.25 | 8.50 | 8.98 | 1.04 | 4.13 | 30.70 | 8.41 | 17.11 | 7.26 |
| | Week 12 | 1010195963 | 1.08 | 2.49 | 1.49 | 251.97 | 6.82 | 5.63 | 0.99 | 3.37 | 20.26 | 6.96 | 14.72 | 5.80 |
| | Week 16 | 1010200033 | 1.03 | 2.34 | 1.24 | 268.43 | 6.96 | 3.93 | 1.05 | 3.18 | 14.30 | 6.92 | 13.96 | 4.38 |
| Donor #1892 | Pre | 1010184804 | 0.13 | <LOD | <LOD | 0.19 | <LOD | 0.04 | <LOD | <LOD | <LOD | <LOD | 0.06 | <LOD |
| | Week 4 | 1010188291 | 22.30 | 1.98 | 0.59 | 0.52 | 0.37 | 41.00 | 1.25 | 0.49 | 18.30 | 3.92 | 1.50 | 1.98 |
| | Week 8 | 1010192199 | 9.75 | 0.93 | 0.21 | 0.50 | 0.10 | 19.40 | 0.59 | 0.15 | 6.91 | 2.52 | 0.37 | 1.27 |
| | Week 10 | 1010194156 | 6.67 | 1.40 | 0.20 | 0.85 | 0.14 | 11.42 | 0.69 | 0.21 | 4.53 | 1.91 | 0.50 | 1.21 |

FIG. 1 (CONT'D)

| Donor | Week | Sample ID | | | | | | | | | | | | | |
|---|---|---|---|---|---|---|---|---|---|---|---|---|---|---|---|
| (continued) | Week 12 | 1010196213 | 6.77 | 0.17 | 1.29 | 0.17 | 1.08 | 0.12 | 10.79 | 0.67 | 0.17 | 4.05 | 2.15 | 0.34 | 1.25 |
| (continued) | Week 16 | 1010200305 | 5.03 | 0.08 | 0.77 | 0.34 | 0.88 | 0.06 | 8.77 | 0.48 | 0.10 | 2.30 | 1.62 | 0.19 | 0.94 |
| Donor #677 | Pre | 1010185343 | 0.15 | 0.17 | 1.12 | 0.34 | 0.34 | 1.87 | 1.18 | 1.38 | 0.70 | 6.70 | 4.00 | 1.28 | 0.60 |
| Donor #677 | Week 4 | 1010189076 | 14.50 | 3.81 | 3.24 | 3.40 | 4.24 | 4.49 | 11.53 | 5.40 | 2.34 | 19.00 | 10.00 | 12.15 | 4.37 |
| Donor #677 | Week 8 | 1010193275 | 12.50 | 2.92 | 2.62 | 2.71 | 3.40 | 4.21 | 9.45 | 5.67 | 2.71 | 20.30 | 9.89 | 11.66 | 3.53 |
| Donor #677 | Week 10 | 1010195037 | 11.90 | 1.23 | 3.56 | 3.34 | 3.34 | 4.18 | 7.16 | 5.99 | 4.27 | 21.10 | 8.63 | 11.25 | 3.69 |
| Donor #677 | Week 12 | 1010196826 | 10.70 | 2.63 | 3.27 | 3.99 | 3.99 | 3.98 | 6.28 | 5.40 | 4.48 | 19.27 | 12.47 | 9.80 | 3.48 |
| Donor #677 | Week 16 | 1010200652 | 10.40 | 2.12 | 3.38 | 4.94 | 4.94 | 4.15 | 8.12 | 6.10 | 5.48 | 19.80 | 18.44 | 10.28 | 3.99 |
| Donor #5462 | Pre | 1010184953 | 0.01 | 0.02 | 0.20 | 0.20 | 0.20 | 0.80 | 4.64 | 0.99 | 0.90 | 0.60 | 11.80 | 0.44 | 0.80 |
| Donor #5462 | Week 4 | 1010189023 | 0.13 | 2.36 | 3.05 | 0.76 | 0.76 | 116.68 | 59.50 | 36.45 | 10.10 | 28.60 | 18.91 | 12.17 | 70.93 |
| Donor #5462 | Week 8 | 1010192671 | 0.12 | 1.20 | 2.32 | 0.81 | 0.81 | 95.55 | 39.71 | 18.50 | 8.90 | 27.30 | 12.63 | 9.88 | 145.80 |
| Donor #5462 | Week 10 | 1010194625 | 0.22 | 1.05 | 3.70 | 1.02 | 1.02 | 81.89 | 38.20 | 27.86 | 9.40 | 36.70 | 16.53 | 13.60 | 150.66 |
| Donor #5462 | Week 12 | 1010196589 | 0.19 | 0.84 | 3.20 | 1.05 | 1.05 | 76.62 | 34.66 | 22.59 | 8.42 | 34.70 | 20.10 | 13.12 | 96.22 |
| Donor #9722 | Pre | 1010185005 | 0.18 | 0.30 | 0.15 | 0.30 | 0.94 | 0.90 | 2.20 | 0.80 | 0.60 | 0.04 | 1.52 | 2.56 | 0.80 |
| Donor #9722 | Week 4 | 1010188743 | 2.28 | 8.43 | 1.24 | 8.69 | 8.69 | 34.41 | 12.66 | 5.40 | 2.43 | 0.48 | 4.42 | 15.60 | 35.23 |
| Donor #9722 | Week 8 | 1010192740 | 2.23 | 9.18 | 1.30 | 8.36 | 8.36 | 25.70 | 13.86 | 6.10 | 2.04 | 0.62 | 4.14 | 17.40 | 39.36 |
| Donor #9722 | Week 10 | 1010194693 | 3.50 | 8.98 | 1.80 | 5.00 | 5.00 | 21.38 | 12.24 | 5.10 | 2.47 | 0.91 | 2.62 | 17.90 | 40.74 |
| Donor #9722 | Week 12 | 1010196667 | 3.40 | 8.55 | 1.86 | 4.91 | 4.91 | 23.32 | 13.63 | 5.70 | 3.99 | 0.96 | 3.20 | 19.68 | 34.18 |
| Donor #6762 | Pre | 1010185392 | 0.29 | 0.45 | 0.45 | 5.18 | 5.18 | 8.04 | 2.50 | 1.00 | 0.16 | 2.20 | 3.40 | 3.28 | 1.60 |
| Donor #6762 | Week 4 | 1010188487 | 8.85 | 2.10 | 1.13 | 50.22 | 69.74 | 13.50 | 32.50 | 5.33 | 1.80 | 19.10 | 8.52 | 10.21 | 41.06 |
| Donor #6762 | Week 8 | 1010192605 | 7.29 | 2.02 | 0.78 | 72.33 | 50.22 | 11.50 | 32.10 | 5.20 | 1.68 | 14.20 | 6.75 | 4.90 | 72.26 |
| Donor #6762 | Week 10 | 1010194533 | 5.67 | 2.45 | 0.72 | 48.43 | 72.33 | 9.36 | 23.80 | 4.40 | 2.34 | 14.30 | 7.10 | 5.15 | 61.24 |
| Donor #6762 | Week 12 | 1010197012 | 4.63 | 1.61 | 0.97 | 3.20 | 48.43 | 9.66 | 11.66 | 4.00 | 2.71 | 14.40 | 5.85 | 4.23 | 65.40 |
| Donor #17767 | Pre | 1010188097 | 1.10 | 0.03 | 0.26 | 0.26 | 3.20 | 0.37 | 4.40 | 0.67 | 0.10 | 0.08 | 2.43 | 1.31 | 0.42 |
| Donor #17767 | Week 4 | 1010191949 | 12.80 | 1.51 | 1.21 | 1.21 | 13.04 | 3.77 | 79.70 | 2.50 | 0.33 | 0.18 | 5.50 | 21.87 | 2.56 |
| Donor #17767 | Week 8 | 1010195914 | 10.90 | 0.86 | 2.10 | 2.10 | 14.33 | 3.55 | 88.11 | 2.28 | 0.24 | 0.12 | 4.05 | 19.52 | 2.26 |
| Donor #17767 | Week 10 | 1010197884 | 13.10 | 1.60 | 1.91 | 1.91 | 13.28 | 3.91 | 88.60 | 3.26 | 0.86 | 0.86 | 7.64 | 23.80 | 2.43 |

FIG. 1 (CONT'D)

| | Donor #7689 | 12.80 | 1.86 | 1.91 | 11.66 | 3.13 | 92.10 | 2.40 | 1.90 | 0.67 | 5.91 | 18.55 | 2.21 |
|---|---|---|---|---|---|---|---|---|---|---|---|---|---|
| Week 12 | 1010200542 | 12.80 | 1.86 | 1.91 | 11.66 | 3.13 | 92.10 | 2.40 | 1.90 | 0.67 | 5.91 | 18.55 | 2.21 |
| Pre | 1010188158 | 1.10 | 5.53 | 0.05 | 0.68 | 0.02 | 0.20 | 0.40 | 0.09 | 0.04 | 1.00 | 1.77 | 0.50 |
| Week 4 | 1010191946 | 10.60 | 21.60 | 0.64 | 3.15 | 0.44 | 10.80 | 5.80 | 0.20 | 0.35 | 3.72 | 7.74 | 2.18 |
| Week 8 | | NOT COLLECTED | | | | | | | | | | | |
| Week 10 | 1010197682 | 15.6 | 22.6 | 0.89 | 3.4 | 0.98 | 11.29 | 5.34 | 0.64 | 1 | 5.5 | 11.01 | 2.2 |
| Week 12 | 1010199903 | 9.7 | 1 | 0.71 | 2.43 | 0.71 | 9.61 | 3.6 | 0.45 | 0.72 | 4.8 | 10.07 | 2.1 |
| Average Pre | | 0.61 | 0.89 | 0.12 | 2.52 | 1.44 | 1.74 | 0.60 | 0.55 | 1.2 | 2.77 | 2.95 | 0.92 |
| Average Week 4 | | 119.5 | 5.31 | 5.46 | 17.47 | 18.73 | 28.21 | 8.38 | 2.69 | 15.9 | 9.1 | 27.2 | 22.45 |
| Average Week 8 | | 84.46 | 4.74 | 4.42 | 18.51 | 16.92 | 24.85 | 6.13 | 2.96 | 13.5 | 7.33 | 20.76 | 34.25 |
| Average Week 10 | | 98.35 | 5.19 | 5.2 | 32.1 | 13.36 | 21.66 | 7.0 | 2.83 | 13.39 | 8.26 | 21.92 | 32.28 |
| Average Week 12 | | 89 | 2.69 | 4.57 | 33.1 | 12.82 | 19.89 | 6.04 | 2.93 | 11.7 | 8.44 | 23.47 | 25.81 |
| Pooled Pre | | 3 | 0.99 | 0.2 | 3.5 | 1.9 | 6.3 | 0.7 | 1 | 1.4 | 4 | 4.2 | 1 |
| Pooled Week 12 | | 91 | 2.6 | 4.5 | 32.1 | 12.8 | 24.2 | 5.8 | 3.2 | 11 | 9 | 23.1 | 24.5 |
| Fold Increase | | 30 | 2.6 | 22 | 9 | 6.7 | 3.8 | 8.3 | 3.2 | 7.9 | 2.2 | 5.5 | 24.5 |

FIG. 2

OPK titers in individual donor sera drawn at different time points

| Donor ID | Time Point | Sample ID | OPK Titer | | | | | | | | | | | |
|---|---|---|---|---|---|---|---|---|---|---|---|---|---|---|
| | | | 1 | 3 | 4 | 5 | 6B | 7F | 9V | 14 | 18C | 19A | 19F | 23F |
| Donor #34440 | Pre | 1010183980 | 256 | 32 | 64 | 64 | 16 | 64 | 4 | 64 | 16 | 32 | 16 | 8 |
| | Week 4 | 1010187977 | 161072 | 128 | 1024 | 128 | 256 | 1024 | 512 | 64 | 128 | 8192 | 128 | 128 |
| | Week 8 | 1010191870 | 65536 | 256 | 2048 | 256 | 128 | 1024 | 1024 | 128 | 512 | 8192 | 128 | 256 |
| | Week 10 | 1010193841 | 131072 | 256 | 4096 | 256 | 128 | 1024 | 512 | 128 | 256 | 8192 | 64 | 128 |
| | Week 12 | 1010195848 | 131072 | 256 | 2048 | 256 | 128 | 1024 | 512 | 128 | 256 | 8192 | 32 | 128 |
| | Week 16 | 1010199412 | 32768 | 128 | 2048 | 256 | 128 | 1024 | 512 | 128 | 256 | 8192 | 32 | 128 |
| Donor #7942 | Pre | 1010184203 | 64 | 32 | 4 | 16 | 64 | 16 | 4 | 4 | 32 | 32 | 4 | 8 |
| | Week 4 | 1010187944 | 1024 | 256 | 128 | 128 | 64 | 128 | 256 | 128 | 128 | 256 | 32 | 128 |
| | Week 8 | 1010191587 | 2048 | 128 | 64 | 64 | 64 | 64 | 512 | 128 | 128 | 256 | 32 | 128 |
| | Week 10 | 1010193786 | 2048 | 256 | 256 | 128 | 128 | 64 | 256 | 128 | 512 | 512 | 64 | 128 |
| | Week 12 | 1010195777 | 2048 | 256 | 256 | 128 | 256 | 64 | 256 | 128 | 128 | 256 | 64 | 128 |
| | Week 16 | 1010200569 | 1024 | 128 | 256 | 128 | 256 | 64 | 256 | 128 | 128 | 256 | 64 | 128 |
| Donor #20003 | Pre | 1010184756 | 32 | 64 | 4 | 512 | 256 | 256 | 64 | 128 | 16 | 256 | 8 | 16 |
| | Week 4 | 1010188381 | 64 | 128 | 64 | 4096 | 1024 | 2048 | 128 | 256 | 64 | 512 | 32 | 32 |
| | Week 8 | 1010192000 | 32 | 256 | 64 | 4096 | 2048 | 1024 | 128 | 512 | 128 | 1024 | 32 | 128 |
| | Week 10 | 1010193932 | 128 | 256 | 128 | 16384 | 2048 | 1024 | 64 | 512 | 256 | 512 | 32 | 512 |
| | Week 12 | 1010195963 | 128 | 256 | 128 | 16384 | 1024 | 1024 | 64 | 512 | 128 | 512 | 32 | 512 |
| | Week 16 | 1010200033 | 128 | 256 | 128 | 32768 | 1024 | 1024 | 64 | 512 | 256 | 512 | 32 | 512 |
| Donor #1892 | Pre | 1010184804 | 32 | 4 | 4 | 16 | 4 | 4 | 4 | 4 | 16 | 4 | 32 | 4 |
| | Week 4 | 1010188291 | 512 | 256 | 256 | 64 | 64 | 4096 | 64 | 64 | 32 | 256 | 128 | 256 |
| | Week 8 | 1010192199 | 256 | 128 | 128 | 64 | 32 | 4096 | 64 | 32 | 32 | 256 | 128 | 128 |

FIG. 2 (CONT'D)

| Donor | Week | ID | | | | | | | | | | | | | |
|---|---|---|---|---|---|---|---|---|---|---|---|---|---|---|---|
| | Week 10 | 1010194156 | 256 | 256 | 128 | 128 | 32 | 128 | 2048 | 32 | 64 | 128 | 256 | 128 | 128 |
| | Week 12 | 1010196213 | 256 | 256 | 128 | 128 | 32 | 128 | 2048 | 32 | 64 | 256 | 256 | 128 | 128 |
| | Week 16 | 1010200305 | 512 | 256 | 128 | 128 | 16 | 128 | 2048 | 64 | 256 | 256 | 256 | 64 | 64 |
| Donor #677 | Pre | 1010185343 | 32 | 64 | 32 | 64 | 128 | 64 | 256 | 64 | 32 | 128 | 128 | 32 | 64 |
| | Week 4 | 1010189076 | 512 | 256 | 128 | 256 | 512 | 512 | 1024 | 512 | 128 | 512 | 1024 | 256 | 512 |
| | Week 8 | 1010193275 | 1024 | 128 | 128 | 256 | 512 | 1024 | 1024 | 512 | 128 | 128 | 1024 | 256 | 256 |
| | Week 10 | 1010195037 | 512 | 256 | 128 | 256 | 512 | 512 | 1024 | 1024 | 64 | 64 | 1024 | 256 | 256 |
| | Week 12 | 1010196826 | 512 | 256 | 256 | 256 | 256 | 1024 | 1024 | 1024 | 64 | 64 | 1024 | 256 | 256 |
| | Week 16 | 1010200652 | 1024 | 256 | 256 | 256 | 512 | 1024 | 1024 | 1024 | 64 | 256 | 1024 | 512 | 512 |
| Donor #5462 | Pre | 1010184953 | 4 | 16 | 4 | 16 | 64 | 4 | 256 | 128 | 8 | 64 | 1024 | 64 | 128 |
| | Week 4 | 1010189023 | 32 | 128 | 128 | 128 | 16384 | 128 | 8192 | 8192 | 128 | 128 | 4096 | 512 | 16384 |
| | Week 8 | 1010192671 | 64 | 256 | 64 | 128 | 8192 | 64 | 8192 | 16384 | 128 | 8192 | 2048 | 1024 | 32768 |
| | Week 10 | 1010194625 | 128 | 256 | 64 | 128 | 32758 | 64 | 8192 | 16384 | 128 | 8192 | 2048 | 1024 | 32768 |
| | Week 12 | 1010196589 | 128 | 256 | 64 | 128 | 16384 | 128 | 8192 | 16384 | 256 | 16384 | 2048 | 1024 | 16384 |
| Donor #9722 | Pre | 1010185005 | 64 | 32 | 32 | 64 | 128 | 64 | 128 | 64 | 32 | 4 | 128 | 256 | 128 |
| | Week 4 | 1010188743 | 256 | 128 | 1024 | 512 | 1024 | 512 | 1024 | 1024 | 64 | 64 | 256 | 8192 | 4096 |
| | Week 8 | 1010192740 | 256 | 128 | 1024 | 512 | 2048 | 1024 | 2048 | 512 | 128 | 64 | 512 | 8192 | 8192 |
| | Week 10 | 1010194693 | 512 | 128 | 1024 | 1024 | 2048 | 1024 | 2048 | 1024 | 128 | 64 | 256 | 16384 | 8192 |
| | Week 12 | 1010196667 | 512 | 128 | 1024 | 1024 | 2048 | 1024 | 2048 | 512 | 128 | 128 | 512 | 8192 | 8192 |
| Donor #6762 | Pre | 1010185392 | 64 | 64 | 32 | 1024 | 1024 | 64 | 128 | 64 | 16 | 128 | 128 | 256 | 128 |
| | Week 4 | 1010188487 | 512 | 128 | 256 | 4096 | 2048 | 512 | 2048 | 512 | 128 | 2048 | 1024 | 1024 | 4096 |
| | Week 8 | 1010192605 | 512 | 128 | 256 | 8192 | 2048 | 1024 | 4096 | 1024 | 64 | 4096 | 1024 | 256 | 8192 |
| | Week 10 | 1010194533 | 1024 | 128 | 256 | 8192 | 2048 | 1024 | 2048 | 1024 | 64 | 4096 | 512 | 256 | 8192 |
| | Week 12 | 1010197012 | 512 | 128 | 128 | 8192 | 2048 | 512 | 4096 | 512 | 64 | 4096 | 1024 | 256 | 8192 |
| Donor #17767 | Pre | 1010188097 | 128 | 64 | 4 | 128 | 128 | 32 | 128 | 128 | 16 | 4 | 128 | 64 | 128 |
| | Week 4 | 1010191949 | 2048 | 128 | 128 | 2048 | 512 | 128 | 16384 | 512 | 64 | 64 | 512 | 4096 | 4096 |
| | Week 8 | 1010195914 | 1024 | 256 | 64 | 2048 | 512 | 64 | 16384 | 512 | 64 | 64 | 512 | 8192 | 512 |

FIG. 2 (CONT'D)

| | | | | | | | | | | | | | |
|---|---|---|---|---|---|---|---|---|---|---|---|---|---|
| Week 10 | 1010197884 | 2048 | 128 | 128 | 4096 | 512 | 16381 | 128 | 64 | 128 | 512 | 8192 | 512 |
| Week 12 | 1010200542 | 2048 | 128 | 128 | 2048 | 1024 | 16384 | 512 | 64 | 128 | 512 | 8192 | 512 |
| Donor #7689 — Pre | 1010188158 | 64 | 256 | 4 | 64 | 4 | 32 | 64 | 8 | 4 | 64 | 128 | 64 |
| Week 4 | 1010191946 | 512 | 4096 | 64 | 128 | 64 | 512 | 512 | 16 | 64 | 256 | 1024 | 256 |
| Week 8 | | | | | | | | | | | | | |
| Week 10 | 1010197682 | 1024 | 4096 | 128 | 256 | 128 | 512 | 512 | 16 | 64 | 256 | 4096 | 256 |
| Week 12 | 1010199903 | 1024 | 4096 | 128 | 128 | 128 | 1024 | 512 | 64 | 64 | 256 | 2048 | 256 |
| Average Pre | | 74 | 62.8 | 18.4 | 196.8 | 196.8 | 126.8 | 49.2 | 22 | 31 | 192.4 | 86 | 61 |
| Average Week 4 | | 16654 | 563.2 | 320 | 1158 | 2195 | 3852 | 1222 | 110 | 681 | 1638 | 1542 | 2649 |
| Average Week 8 | | 7804 | 1436 | 427 | 1735 | 1732 | 4217 | 2296 | 145 | 1482 | 1649 | 2027 | 5617 |
| Average Week 10 | | 13875 | 601 | 1030 | 3084 | 4034 | 2150 | 2099 | 146 | 1376 | 1408 | 3049 | 5107 |
| Average Week 12 | | 7899 | 601 | 428 | 2867 | 2333 | 3693 | 2035 | 163 | 2163 | 1459 | 2022 | 3494 |
| Pooled Pre | | 256 | 64 | 32 | 256 | 256 | 2048 | 64 | 64 | 32 | 256 | 128 | 64 |
| Pooled Week 12 | | 16384 | 1024 | 512 | 4096 | 2048 | 8192 | 2048 | 16384 | 2048 | 2048 | 2048 | 4096 |
| Fold Increase OPK Titer | | 64 | 16 | 16 | 16 | 8 | 4 | 32 | 256 | 64 | 8 | 16 | 64 |

FIG. 3

Pneumococcal serotype specific IgG Concentrations in pooled donor sera drawn at different time points after immunization

| Time Point | Serotype specific antibody concentration (µg/mL) | | | | | | | | | | | |
|---|---|---|---|---|---|---|---|---|---|---|---|---|
| | 1 | 3 | 4 | 5 | 6B | 7F | 9V | 14 | 18C | 19A | 19F | 23F |
| Pre | 1.38 | 1.15 | 0.13 | 2.08 | 0.99 | 4.79 | 0.21 | 2.20 | 1.82 | 1.58 | 0.55 | 0.57 |
| Week 8 | 42.25 | 9.17 | 5.85 | 47.24 | 7.74 | 31.43 | 6.88 | 17.64 | 24.85 | 14.97 | 11.57 | 36.73 |
| Week 10 | 42.76 | 7.80 | 4.55 | 39.87 | 7.46 | 25.66 | 6.46 | 13.89 | 20.59 | 16.46 | 10.88 | 27.40 |
| Week 12 | 39.03 | 7.09 | 4.58 | 32.71 | 6.81 | 26.14 | 8.11 | 12.62 | 18.35 | 16.03 | 12.60 | 26.82 |
| Week 16 | 34.36 | 6.83 | 3.97 | 29.73 | 5.37 | 17.27 | 4.82 | 8.90 | 11.43 | 11.73 | 7.61 | 17.21 |
| Month 5 | 29.58 | 5.52 | 3.05 | 24.38 | 4.95 | 19.50 | 3.71 | 10.31 | 13.22 | 12.13 | 6.03 | 6.40 |
| Average—Post Only | 37.59 | 7.28 | 4.40 | 34.79 | 6.46 | 24.00 | 6.00 | 12.67 | 17.69 | 14.26 | 9.74 | 22.91 |

FIG. 4

Fold increase in pneumococcal serotype specific IgG Concentrations in pooled donor sera drawn at different time points after immunization

| Time Point | Fold Increase | | | | | | | | | | | |
|---|---|---|---|---|---|---|---|---|---|---|---|---|
| | 1 | 3 | 4 | 5 | 6B | 7F | 9V | 14 | 18C | 19A | 19F | 23F |
| Pre* | 1.38 | 1.15 | 0.13 | 2.08 | 0.99 | 4.79 | 0.21 | 2.20 | 1.82 | 1.58 | 0.55 | 0.57 |
| Week 8 | 30.62 | 7.98 | 44.12 | 22.69 | 7.78 | 6.57 | 32.54 | 8.02 | 13.67 | 9.44 | 21.23 | 64.22 |
| Week 10 | 30.99 | 6.78 | 34.35 | 19.15 | 7.50 | 5.36 | 30.55 | 6.31 | 11.33 | 10.39 | 19.96 | 47.90 |
| Week 12 | 28.29 | 6.17 | 34.53 | 15.71 | 6.85 | 5.46 | 38.33 | 5.74 | 10.09 | 10.11 | 23.12 | 46.88 |
| Week 16 | 24.90 | 5.95 | 29.99 | 14.28 | 5.40 | 3.61 | 22.79 | 4.05 | 6.29 | 7.40 | 13.96 | 30.08 |
| Month 5 | 21.44 | 4.81 | 23.05 | 11.71 | 4.97 | 4.07 | 17.55 | 4.69 | 7.27 | 7.66 | 11.07 | 11.19 |
| Average—Post/Pre | 27.25 | 6.34 | 33.21 | 16.71 | 6.50 | 5.01 | 28.35 | 5.76 | 9.73 | 9.00 | 17.87 | 40.06 |

* = baseline

FIG. 5

Pneumococcal serotype specific OPK titers in pooled donor sera drawn at different time points after immunization

| Time Point | OPK titer | | | | | | | | | | | |
|---|---|---|---|---|---|---|---|---|---|---|---|---|
| | 1 | 3 | 4 | 5 | 6B | 7F | 9V | 14 | 18C | 19A | 19F | 23F |
| Pre | 32.00 | 16.00 | 8.00 | 64.00 | 16.00 | 128.00 | 8.00 | 32.00 | 32.00 | 32.00 | 16.00 | 16.00 |
| Week 8 | 32768.00 | 256.00 | 128.00 | 1024.00 | 1024.00 | 2048.00 | 256.00 | 1024.00 | 2048.00 | 1024.00 | 512.00 | 2048.00 |
| Week 10 | 65536.00 | 256.00 | 64.00 | 1024.00 | 1024.00 | 1024.00 | 256.00 | 2048.00 | 2048.00 | 1024.00 | 512.00 | 2048.00 |
| Week 12 | 32768.00 | 128.00 | 64.00 | 512.00 | 2048.00 | 2048.00 | 128.00 | 2048.00 | 1024.00 | 1024.00 | 256.00 | 2048.00 |
| Week 16 | 32768.00 | 256.00 | 128.00 | 1024.00 | 512.00 | 2048.00 | 128.00 | 1024.00 | 1024.00 | 512.00 | 256.00 | 1024.00 |
| Month 5 | 16384.00 | 128.00 | 64.00 | 1024.00 | 512.00 | 1024.00 | 64.00 | 1024.00 | 1024.00 | 512.00 | 256.00 | 1024.00 |
| Average—Post Only | 36044.80 | 204.80 | 89.60 | 921.60 | 1024.00 | 1638.40 | 166.40 | 1433.60 | 1433.60 | 819.20 | 358.40 | 1638.40 |

FIG.6

Pneumococcal serotype specific IgG Concentrations in purified IgG made from pooled donor plasma which was drawn at different time points after immunization

| Time Point | Serotype specific antibody concentration (µg/mL) | | | | | | | | | | | | | | |
|---|---|---|---|---|---|---|---|---|---|---|---|---|---|---|
| | 1 | 3 | 4 | 5 | 6B | 7F | 9V | 14 | 18C | 19A | 19F | 23F |
| Pre | 0.81 | 1.0 | 0.09 | 2.05 | 0.72 | 3.31 | 0.15 | 1.91 | 1.11 | 1.04 | 0.61 | 0.44 |
| Week 12 | 33.2 | 7.37 | 4.28 | 34.23 | 3.96 | 13.58 | 6.91 | 10.19 | 8.43 | 7.77 | 11.5 | 18.54 |
| Week 16 | 19.36 | 4.22 | 2.67 | 23.15 | 3.63 | 11.96 | 5.22 | 10.33 | 6.81 | 6.21 | 8.3 | 15.5 |
| Month 5 | 17.28 | 3.87 | 2.54 | 19.23 | 3.01 | 11.29 | 3.61 | 10.86 | 7.47 | 6.07 | 6.71 | 12.42 |
| Average Post only | 23.3 | 5.2 | 3.2 | 25.5 | 3.5 | 12.3 | 5.2 | 10.5 | 7.6 | 6.7 | 8.8 | 15.5 |

FIG. 7

Pneumococcal serotype specific OPK titers in purified IgG made from pooled donor plasma which was drawn at different time points after immunization

| Time Point | OPK titer | | | | | | | | | | | |
|---|---|---|---|---|---|---|---|---|---|---|---|---|
|  | 1 | 3 | 4 | 5 | 6B | 7F | 9V | 14 | 18C | 19A | 19F | 23F |
| Pre | 32 | 128 | 4 | 64 | 64 | 256 | 16 | 128 | 64 | 32 | 32 | 16 |
| Week 12 | 4096 | 1024 | 64 | 4096 | 256 | 8192 | 1024 | 2048 | 1024 | 256 | 256 | 4096 |
| Week 16 | 2048 | 1024 | 128 | 4096 | 512 | 8192 | 512 | 4096 | 1024 | 256 | 256 | 8192 |
| Month 5 | 2048 | 512 | 128 | 4096 | 512 | 1096 | 256 | 2048 | 512 | 128 | 128 | 2048 |
| Average Post only | 2730.7 | 853.3 | 106.7 | 4096.0 | 426.7 | 5826.7 | 597.3 | 2730.7 | 853.3 | 213.3 | 1109.3 | 4778.7 |

FIG. 8

Comparison of Pneumococcal serotype specific OPK titers in 9 different lots of commercial immunoglobulin as compared to a hyperimmune globulin preparation purified from a pool of plasma donors 12 weeks post immunization

| Sample ID | OPK Serotype Titer | | | | | | | | | | | |
|---|---|---|---|---|---|---|---|---|---|---|---|---|
| | 1 | 3 | 4 | 5 | 6B | 7F | 9V | 14 | 18C | 19A | 19F | 23F |
| A160314-A | 128 | 4 | 32 | 16 | 1024 | 2048 | 64 | 64 | 64 | 32 | 8 | 64 |
| A160314-B | 128 | 4 | 64 | 256 | 256 | 1024 | 64 | 128 | 256 | 32 | 32 | 128 |
| A160314-C | 64 | 4 | 32 | 32 | 256 | 2048 | 32 | 128 | 16 | 32 | 16 | 64 |
| A160314-D | 16 | 4 | 32 | 16 | 64 | 2048 | 32 | 4 | 16 | 32 | 16 | 64 |
| A160314-E | 32 | 4 | 16 | 64 | 32 | 1024 | 16 | 4 | 4 | 256 | 32 | 256 |
| A160314-F | 16 | 4 | 32 | 16 | 16 | 64 | 32 | 128 | 4 | 64 | 16 | 512 |
| A160314-G | 16 | 4 | 16 | 32 | 16 | 64 | 16 | 4 | 4 | 8 | 8 | 1024 |
| A160314-H | 32 | 4 | 16 | 32 | 8 | 512 | 16 | 16 | 16 | 8 | 32 | 16 |
| A160314-I | 32 | 4 | 64 | 16 | 16 | 256 | 16 | 16 | 16 | 8 | 16 | 16 |
| IVIG Average | 52 | 4 | 34 | 53 | 188 | 1010 | 32 | 55 | 44 | 52 | 20 | 238 |
| Pre | 16 | 128 | 8 | 128 | 32 | 512 | 32 | 128 | 128 | 64 | 64 | 32 |
| Hyper Immune IVIG | 2048 | 1024 | 256 | 4096 | 512 | 8192 | 1024 | 2048 | 1024 | 256 | 1024 | 8192 |
| Fold Increase over commercial IVIG | 40 | 256 | 8 | 77 | 3 | 16 | 32 | 37 | 23 | 5.00 | 52 | 34 |

FIG. 10

Percentage of subjects with primary immune deficiency disease that fall below protective levels (1.2 μg/ml) of anti-*S pneumonia* binding antibodies at trough after infusion of conventional IVIG

| | |
|---|---|
| Serotype 1 | 47.5 |
| Serotype 3 | 49.2 |
| Serotype 4 | 94.9 |
| Serotype 5 | none |
| Serotype 6B | 52.5 |
| Serotype 7F | 31.0 |
| Serotype 9V | 39.0 |
| Serotype 14 | none |
| Serotype 18C | none |
| Serotype 19A | none |
| Serotype 19F | none |
| Serotype 23F | 61.0 |

ANTI-PNEUMOCOCCAL HYPERIMMUNE GLOBULIN FOR THE TREATMENT AND PREVENTION OF PNEUMOCOCCAL INFECTION

CROSS-REFERENCE TO RELATED APPLICATIONS

The present application is a continuation of U.S. patent application Ser. No. 17/397,915, filed Aug. 9, 2021, now allowed as U.S. Pat. No. 11,897,943, which is a continuation of U.S. patent application Ser. No. 16/384,334, filed Aug. 15, 2019, now allowed as U.S. Pat. No. 11,084,870, which is a continuation of U.S. patent application Ser. No. 15/460, 147, filed Mar. 15, 2017, now allowed as U.S. Pat. No. 10,259,865, the contents of which is incorporated by reference in its entirety.

FIELD

The present invention relates to compositions and methods for the treatment of infection caused by or associated with *Streptococcus pneumonia*. In particular, the invention provides human hyperimmune globulin and compositions thereof for preventing or treating pneumococcal infection. The invention provides methods of producing immune globulin containing high titers of opsonic anti-pneumococcal antibodies, compositions containing same, and methods of using the compositions for the prevention and treatment of pneumococcal infection (e.g., upper respiratory tract infections (e.g., sinusitis, otitis media, pharyngitis, etc. (e.g., in an immunocompromised subject))).

BACKGROUND

There are many components to the immune system all of which cooperate to reject foreign invading pathogens. While most people have intact immune systems that serve to protect them from the wide variety of infectious organisms that commonly infect people including viruses, bacteria and fungi, many individuals have impaired or compromised immunity.

Primary immunodeficiencies (PIDs) are a group of greater than 200 genetically inherited disorders characterized by deficiencies in individual components of the innate or adaptive immune system with a clinical result of an increased susceptibility to infection. For example, a defect in the humoral immune system which impairs the ability of the body to make antibodies renders the person susceptible to many infections. To be considered a primary immunodeficiency, the cause of the immune deficiency must not be secondary in nature (e.g., caused by other disease, drug treatment, or environmental exposure to toxins). Most primary immunodeficiencies are genetic disorders and are diagnosed in children, although less severe forms may not be recognized until adulthood. About 1 in 500 people are born with a primary immunodeficiency.

Intravenous infusion of immune globulin has been shown to reconstitute the ability of immune defective individuals to defend themselves against infection. Since the immune globulin is pooled from many donors the antibody titers to the many infectious organisms for which protection must be sought varies greatly and may or may not be ample to meet the immune needs in case of infection in an immune compromised individual.

Most commercially available immunoglobulins are derived from human plasma collected, processed, and distributed for sale by the blood and plasma products industry. The first purified human immunoglobulin G (IgG) preparation used clinically was immune serum globulin which was produced in the 1940s (Cohn, E. J., et al "J. Am Chem. Soc., 68:459-475 (1946)) and Oncely, J. L. et al., J. Am Chem Soc. 71:541-550 (1949). The gammaglobulin produced by this method show a molecular distribution having a high molecular weight, when analyzed by way of high resolution size exclusion chromatography.

Standard immune globulin (IVIG) has been shown to have lot to lot variability for opsonic activity to a very common commensal organism that is ubiquitous on human skin, *S. epidermidis* (L. A. Clark and C. S. F. Easmon, J. Clin. Pathol. 39:856 (1986)). For example, in the study by Clark and Easmon, one third of the IVIG lots tested had poor opsonic activity with complement, and only two of fourteen were opsonic without complement. Thus, despite the fact that the IVIG lots were made from large plasma donor pools, good opsonic antibody to *S. epidermidis* was not uniformly present.

IVIG has generally been successful to prevent severe lower respiratory tract infections in immune compromised patients. However, despite the fact the immune compromised patients receiving IVIG appear to have acceptable levels of total immunoglobulin as well as sufficient levels of anti *S. pneumonia* antibody to prevent serious bacterial infections caused by *S. pneumonia*, there exists a significant percentage of the patients who experience upper respiratory tract infections and non-respiratory infections that is debilitating, lowers their quality of life, leads to increased use of antibiotics which are not effective and also leads to enhanced medical expenditures (See, e.g., Favre et al., Allergy 2005 60:385-390).

SUMMARY OF THE INVENTION

The present invention relates to compositions and methods for the treatment of infection caused by *Streptococcus pneumonia*. In particular, the invention provides human immune globulin and compositions thereof for preventing or treating pneumococcal infection. The invention provides methods of producing immune globulin containing high titers of anti-pneumococcal antibodies with opsonic activity (e.g., to a multitude of *S. pneumonia* serotypes), compositions containing same, and methods of using the compositions for the prevention and treatment of pneumococcal infection. The invention further provides methods of preventing or treating pneumococcal infection (e.g., upper respiratory infections (e.g., pharyngitis, otitis media, sinusitis, etc.)) in immunocompromised subjects (e.g., via administration of immune globulin compositions of the invention (e.g., containing a high titer of opsonic anti-pneumococcal antibodies) to immunocompromised subjects who have not been adequately protected by regular infusions of standard IVIG).

In one embodiment, it is an object of the invention to provide a novel immune globulin composition prepared from plasma donors according to methods of the invention (e.g., human plasma donors (e.g., healthy human plasma donors) that have been vaccinated with one or more pneumococcal vaccines according to methods described herein) that contains an elevated titer of anti-pneumococcal-specific, antibodies with opsonic activity when compared to a control sample.

The invention is not limited by the type of control sample utilized. For example, in one embodiment, a control sample is immune globulin prepared from a healthy human plasma donor(s) pre-vaccination (e.g., such that the pre-immunization levels of anti-pneumococcal-specific, opsonic antibody titers of the human plasma donors are used as a baseline to measure the increase in the anti-pneumococcal-specific, opsonic antibody titers post immunization). In another embodiment, a control sample is immune globulin prepared from a mixture of plasma samples obtained from random human plasma donors (e.g., 100, 300, 500, 1000 or more random human plasma donors) that have not been vaccinated with an anti-pneumococcal vaccine (e.g., such that the levels of anti-pneumococcal-specific, opsonic antibody titers of the non-vaccinated human plasma donors are used as a baseline to measure the increase in the anti-pneumococcal-specific, opsonic antibody titers present in human plasma donors vaccinated according to methods of the invention). Those of skill in the art will appreciate that other control samples may be utilized. The invention is not limited by the method or assay used to measure the opsonic (e.g., opsonophagocytic) titer of antibody present. Indeed, a variety of assays may be used including, but not limited to, those described herein (e.g., in Example 1).

In one embodiment, it is an object of the invention to provide a novel immune globulin composition containing a high titer of opsonic, anti-pneumococcal antibodies. It is a further object of the invention to provide a novel intravenous immune globulin composition containing a high titer of opsonic, anti-pneumococcal antibodies (e.g., "anti-pneumococcal hyper-immune globulin") and methods of producing and utilizing the same (e.g., for preventing and/or treating pneumococcal infection (e.g., in immune compromised patients)). The term "high titer" in this context means the presence of opsonic anti-pneumococcal antibody in an amount which is 2-fold or greater, e.g., 3-, 5-, 7-, 10-, 15-, 20-or more times higher than that found in a control sample.

Accordingly, a novel immune globulin composition (e.g., anti-pneumococcal hyper-immune globulin) containing a high titer of opsonic, anti-pneumococcal antibodies of the invention is different than standard/conventional immune globulin preparations (e.g., standard, conventional IVIG) and is different than other IVIG preparations (e.g., other hyper-immune IVIG preparations) in that it has a high titer of opsonic, human anti-pneumococcal antibodies that are functionally and broadly reactive against a multitude of S. pneumonia serotypes and enhance phagocytosis and killing of S. pneumonia (e.g., in vitro and/or in vivo (e.g., the antibodies are opsonophagocytic)), independent of the total amount of binding anti-pneumococcal antibodies (e.g., as measured by ELISA) that are present in the composition.

This is surprising since data generated and disclosed herein indicated that there was no consistent or predictable correlation between total anti-pneumococcal IgG antibody titer and the titer of opsonic anti-pneumococcal antibodies present in plasma or immune globulin prepared from vaccinated donors. Due to the surprising identification of the great discordance between the total amount of binding anti-pneumococcal IgG antibody titer and the titer of opsonic anti-pneumococcal antibodies present in plasma, or immune globulin prepared from same, from vaccinated donor plasma disclosed herein, it is a further object of the invention to provide a plasma and/or immune globulin composition (e.g., anti-pneumococcal hyper-immune globulin) containing significantly elevated functional, opsonic anti-pneumococcal antibody titers (e.g., regardless of the total amount of binding anti-pneumococcal antibody titer (e.g., by pooling plasma and/or immune globulin harvested from vaccinated donor plasma, or, by pooling vaccinated donor plasma together with immune globulin obtained from unvaccinated donors that may not have a high titer of opsonic anti-pneumococcal antibodies that when pooled with the significantly elevated titer opsonic anti-pneumococcal antibody donor plasma and/or immune globulin do not dilute the total opsonic titer to a non-protective level)) compared to a control sample. Encompassed by the invention is sera/plasma as well as immune globulin (e.g., hyper-immune globulin) prepared from same containing significantly elevated functional, and broadly reactive opsonic anti-pneumococcal antibody titers. In one embodiment, the invention provides plasma/sera and/or immune globulin prepared from same containing an elevated anti-pneumococcal-specific, opsonic antibody titer that is at least 2-fold, 3-fold, 4-fold, 5-fold, 7-fold, 10-fold, or more greater for at least about 55% or more (e.g., 60%, 65%, 70%, 75%, 80%, 85% or more) of S. pneumonia serotypes 1, 3, 4, 5, 6B, 7F, 9V, 14, 18C, 19A, 19F, and 23F) compared to the anti-pneumococcal-specific, opsonic antibody titers for the same serotypes present in a control sample (immune globulin prepared from a mixture of plasma samples obtained from random human plasma donors (e.g., 100, 300, 500, 1000 or more random human plasma donors) that have not been vaccinated with an anti-pneumococcal vaccine).

In another embodiment, the invention provides a hyper-immune globulin (e.g., IVIG) composition containing a titer of broadly reactive opsonic antibodies, specific for 70% or more of the S. pneumonia serotypes selected from serotypes 4, 6B, 9V, 14, 18C, 19F, and 23, that is 2 fold or greater (e.g., 3-25 fold or greater) than the titer of opsonic antibodies specific for the same S. pneumonia serotypes present in a control sample (e.g., immune globulin prepared from a mixture of plasma samples obtained from random human plasma donors (e.g., 100, 300, 500, 1000 or more random human plasma donors) that have not been vaccinated with an anti-pneumococcal vaccine. In another embodiment, the invention provides plasma/sera and/or immune globulin prepared from same containing an anti-pneumococcal-specific, opsonic antibody titer between 1:64 and 1:8192 (e.g., for at least 50% or more (e.g., 60%, 65%, 70%, 75%, 80%, 85% or more) of S. pneumonia serotypes 1, 3, 4, 5, 6B, 7F, 9V, 14, 18C, 19A, 19F, and 23F).

It is also an object of the invention to provide a novel immune globulin composition (e.g., anti-pneumococcal hyperimmune globulin) containing a high titer of opsonic, anti-pneumococcal antibodies that enhances immunity in vivo and/or preventatively and therapeutically inhibits infection (e.g., upper respiratory tract infection), in patients with compromised immune systems who do not adequately respond to regular infusions of conventional IVIG.

It is also another advantageous object of the present invention that while standard immunoglobulin pools of normal donors (e.g., used to generate commercially available, standard/conventional IVIG) do not have consistent, reproducible and fully protective levels of opsonic antibody for S. pneumonia, a hyperimmune globulin composition (e.g., anti-pneumococcal hyperimmune globulin) containing a high titer of opsonic, anti-pneumococcal antibodies of the invention when given intravenously immediately provides specific, functional (e.g., not merely binding) antibodies that promote phagocytosis and killing of S. pneumonia by phagocytes. The invention is not limited by the serotype or number of serotypes of S. pneumonia for which the functional, opsonic antibodies present within a hyperimmune globulin (e.g., IVIG) composition of the invention promotes the phagocytosis and/or killing. Indeed, it is a further object of the invention that a composition (e.g., a hyperimmune plasma composition and/or a hyperimmune globulin (e.g., IVIG) composition) of the invention contains broadly reactive, opsonic antibodies to at least 7 of 12, 8 of 12, 9 of 12, 10 of 12, 11 of 12 or all 12 of 12 of the following serotypes of *S. pneumonia*: 1, 3, 4, 5, 6B, 7F, 9V, 14, 18C, 19A, 19F, and 23F. That is, the invention provides compositions and methods of obtaining same that comprise an elevated opsonic anti-pneumococcal-specific antibody titer that is at least 2-fold, 3-fold, 4-fold, 5-fold, 7-fold, 10-fold, or more greater than the opsonic anti-pneumococcal-specific antibody titer present in a control sample (e.g., for at least about 55% or more (e.g., 60%, 65%, 70%, 75%, 80%, 85% or more)) of the pneumococcal serotypes selected from serotypes 1, 3, 4, 5, 6B, 7F, 9V, 14, 18C, 19A, 19F, and 23F). In one embodiment, the invention provides an immune globulin (e.g., a hyperimmune globulin (e.g., IVIG)) composition containing a titer of broadly reactive opsonic antibodies, specific for 70% or more of the *S. pneumonia* serotypes selected from serotypes 4, 6B, 9V, 14, 18C, 19F, and 23, that is 2 fold or greater (e.g., 3-25 fold or greater) than the titer of opsonic antibodies specific for the *S. pneumonia* serotypes present in a control sample (e.g., immune globulin prepared from a mixture of plasma samples obtained from random human plasma donors (e.g., 100, 300, 500, 1000 or more random human plasma donors) that have not been vaccinated with an anti-pneumococcal vaccine, or, immune globulin prepared from a healthy human plasma donor(s) pre-vaccination (e.g., such that the pre-immunization levels of serotype-specific, opsonic antibody titers of the human plasma donors are used as a baseline to measure the increase in the serotype-specific, opsonic antibody titers post immunization)). In another embodiment, the invention provides an immune globulin (e.g., a hyperimmune globulin (e.g., IVIG)) composition that contains a high titer of broadly reactive, opsonic antibodies to at least 50%, to at least 55%, to at least 60%, to at least 65%, to at least 70%, at least 75%, at least 80%, at least 85%, at least 90%, 95%, 98%, or more of each serotype present in a vaccine or a plurality of vaccines utilized to immunize one or more plasma donors from which the immune globulin composition is derived.

It is a further advantage and object of the invention to provide a hyperimmune globulin (e.g., IVIG) composition containing broadly reactive, opsonic antibodies specific for *S. pneumonia* to a patient (e.g., an immune compromised patient (e.g., a PIDD patient)) in order to treat or prevent pneumococcal infection in the patient (e.g., by inhibiting *S. pneumonia* growth and/or clearing *S. pneumonia* from the blood of the patient). Another advantage and object of the invention is to provide a hyperimmune globulin (e.g., IVIG) composition of the invention containing broadly reactive, opsonic antibodies specific for *S. pneumonia* to a patient (e.g., an immune compromised patient (e.g., a PIDD patient)) in order to treat pneumococcal infection in the patient (e.g., by improving or enhancing *S. pneumonia* clearance from the blood of the patient). It is a further advantage and object of the invention to provide a hyperimmune globulin (e.g., IVIG) composition of the invention containing broadly reactive, opsonic antibodies specific for *S. pneumonia* to a patient (e.g., an immune compromised patient (e.g., a PIDD patient)) in order to prevent upper respiratory tract infections in the patient that are not preventable with conventional IVIG treatment. The invention is not limited by the type of upper respiratory tract infection prevented and/or treated and may include, but is not limited to, rhinosinusitis (sinusitis), otitis media, pharyngitis, epiglottitis, laryngotracheitis, and laryngotracheobronchitis. Similarly, compositions and methods of using (e.g., administering) the same find use in preventing and/or treating signs or symptoms of upper respiratory tract infection including, but not limited to, cough, sneezing, nasal discharge, nasal congestion, runny nose, fever, scratchy or sore throat, and nasal breathing.

In one embodiment, the invention provides compositions and methods for obtaining a composition comprising pooled plasma samples (e.g., plasma from a plurality of donors (e.g., donors that have been vaccinated with one or more pneumococcal vaccines)) that contain high titers of opsonic anti-pneumococcal antibodies.

Thus, it is an object of the invention to provide methods of generating compositions (e.g., blood, plasma, and/or immune globulin (e.g., hyperimmune globulin) compositions) containing a high titer of opsonic, anti-pneumococcal antibodies. In one embodiment, one or a plurality of healthy adult human subjects (e.g., human subjects with no known medical conditions) are administered a pneumococcal immunogen, recombinant pneumococcal protein, or a combination thereof. In some embodiments, a *S. pneumonia* immunogen is a *S. pneumonia* cell membrane sugar (e.g., a polysaccharide). In some embodiments, the *S. pneumonia* immunogen is a *S. pneumonia* vaccine containing one or a plurality of *S. pneumonia* proteins (e.g., recombinant or isolated proteins). In some embodiments, a *S. pneumonia* immunogen is a conjugate vaccine (e.g., conjugated to a carrier and/or adjuvant (e.g., a protein or other carrier molecule)). In some embodiments, a *S. pneumonia* immunogen is an unconjugated vaccine. In some embodiments, the conjugate vaccine or unconjugated vaccine contains 1, 2, 3, 4, 5, 6, 7, 8, 9, 10, 11, 12, 13, 14, 15, 16 ,17, 18, 19, 20, 21, 22, 23 or more different immunogens (e.g., from an equal number of different serotypes of *S. pneumonia*). In some embodiments, the one or more different serotypes of *S. pneumonia* include, but are not limited to, serotypes 1, 2, 3, 4, 5, 6A, 6B, 7A, 7B, 7C, 7D, 7E, 7F, 8, 9A-9V, 12, 14, 18C, 19A-19F, 23A-23F, and 25. In some embodiments, the one or more different serotypes of *S. pneumonia* are selected from any one of the more the 90 different known *S. pneumonia* serotypes. In some embodiments, the one or more different serotypes of *S. pneumonia* is newly identified.

In a further embodiment, one or a plurality of healthy human subjects (e.g., human subjects with no known medical conditions) are administered a pneumococcal immunogen, recombinant pneumococcal protein, or a combination thereof present in a commercial pneumococcal vaccine. The invention is not limited by the type of commercial pneumococcal vaccine. Indeed, any pneumococcal vaccine known in the art can be utilized including, but not limited to, pneumococcal conjugate vaccine (PCV13 or PREVNAR13, Wyeth Pharmaceuticals, Collegeville, PA), SYNFLORIX, and/or pneumococcal polysaccharide vaccine (PPSV23 or PNEUMOVAX23, Merck Sharp & Dohme Corp., North Wales, PA). In one embodiment, one or a plurality of healthy human subjects receives a first or prime vaccination with a first anti-pneumococcal vaccine, and a subsequent boost vaccination with the first anti-pneumococcal vaccine or with a second, different anti-pneumococcal vaccine. For example, in one embodiment, one or a plurality of healthy human subjects receive a first or prime vaccination/immunization with a first anti-pneumococcal vaccine (e.g., PREVNAR), and then receive a boost vaccination/immunization (e.g., at 2 weeks, 4 weeks, 6, weeks, 8 weeks, 10 weeks, 12 weeks or longer post the prime vaccination/immunization) with a second anti-pneumococcal vaccine (e.g., PNEU-MOVAX23). At a time point subsequent to the sequential vaccination (e.g., at 2 weeks, 4 weeks, 6, weeks, 8 weeks, 10 weeks, 12 weeks or longer post the sequential vaccination), sera/plasma is harvested from the vaccinated, healthy human plasma donors. Plasma from the vaccinated donors may be pooled (with each other and/or with plasma from non-vaccinated donors) followed by isolation and/or purification of immune globulin from same (e.g., in order to generate an anti-pneumococcal hyper-immune globulin of the invention). Methods of harvesting plasma as well as extraction of immune globulin are well known by those of ordinary skill in the art.

In one embodiment, the invention provides a method for preparing a hyperimmune globulin having a high titer of opsonophagocytic antibody to *Streptococcus pneumonia* (e.g., a titer that is at least 2-fold, 3-fold, 4-fold, 5-fold, 7-fold, 10-fold, or more greater for at least about 55% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) compared to the anti-pneumococcal-specific, opsonophagocytic antibody titers for the same serotypes present in a control sample; or, a titer specific for 70% or more of the *S. pneumonia* serotypes selected from serotypes 4, 6B, 9V, 14, 18C, 19F, and 23, that is 2 fold or greater (e.g., 3-25 fold or greater) than the titer of opsonophagocytic antibodies specific for the same *S. pneumonia* serotypes present in a control sample; or, a titer between 1:64 and 1:8192 (e.g., at least 1:256 (e.g., for at least 50% or more (e.g., 60%, 65%, 70%, 75%, 80%, 85% or more)) of *S. pneumonia* serotypes 1, 3, 4, 5, 6B, 7F, 9V, 14, 18C, 19A, 19F, and 23F) as determined by an opsonophagocytic killing assay described herein) comprising the steps of immunizing healthy adult human plasma donors between the ages of 18-60 with a primary immunization with a multivalent *S. pneumonia* vaccine followed by immunization with a boost multivalent *S. pneumonia* vaccine that is either the same or may be different than the primary vaccine; harvesting plasma from the plasma donors subsequent to the boost immunization; pooling plasma from the vaccinated donors in order to obtain a pooled plasma containing a high titer of opsonophagocytic antibody titer to *S. pneumonia*; and preparing an immune globulin from the pooled plasma. In a further embodiment, the method comprises rendering the immune globulin obtained intravenously injectable. The immune globulin can be provided in solution and/or the pH and ionic strength of the solution can be adjusted so as to render it intravenously injectable. The invention is not limited by the number of individuals vaccinated according to the methods described herein. For example, 100, 200, 300, 400, 500, 600, 700, 800, 900, 1000, 1100, 1200, 1300, 1400 or more healthy adult human plasma donors can be vaccinated and plasma harvested from the donors. In one embodiment, the pooled plasma is made from pooling plasma from 1000 or more different vaccinated healthy adult human plasma donors. In one embodiment, the pooled plasma contains an opsonophagocytic antibody titer that is at least 2-fold, 3-fold, 4-fold, 5-fold, 7-fold, 10-fold, or more greater for at least about 55% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) compared to the opsonophagocytic anti-pneumococcal-specific antibody titers for the same serotypes present in a control sample (e.g., immune globulin prepared from plasma pooled from 1000 or more random non-vaccinated human plasma donors). In another embodiment, the pooled plasma contains an opsonophagocytic antibody titer specific for 70% or more of the *S. pneumonia* serotypes selected from serotypes 4, 6B, 9V, 14, 18C, 19F, and 23, that is 2 fold or greater (e.g., 3-25 fold or greater) than the titer of opsonophagocytic antibodies specific for the same *S. pneumonia* serotypes present in a control sample (e.g., immune globulin prepared from plasma pooled from 1000 or more random non-vaccinated human plasma donors). In yet another embodiment, the pooled plasma contains an opsonophagocytic antibody titer between 1:64 and 1:8192 (e.g., for at least 50% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) as determined by an opsonophagocytic killing assay described herein or known in the art.

The invention also provides an immune globulin (e.g., a hyperimmune globulin) prepared according the above described method. The immune globulin (e.g., hyperimmune globulin) so prepared can be used in various methods. For example, the immune globulin can be used in a method of treating *S. pneumonia* infection in a subject (e.g., comprising administering to the subject a therapeutically effective amount of the immune globulin). The immune globulin can also be used in a method of providing immunotherapy to a subject (e.g., comprising administering to the subject a therapeutically effective amount of the immune globulin).

The invention also provides, in one embodiment, a method of preparing a hyperimmune globulin having enhanced opsonophagocytic bactericidal activity against at least seven serotypes of *Streptococcus pneumonia* for the prevention or treatment of *S. pneumonia* infection comprising the steps of immunizing healthy adult human plasma donors with a primary immunization with a multivalent *S. pneumonia* conjugate vaccine followed by boost immunization with a multivalent polysaccharide *S. pneumonia* vaccine that is different than the prime vaccine; harvesting and pooling the plasma from the immunized plasma donors; and preparing immune globulin from the pooled plasma, wherein the immune globulin contains an opsonophagocytic antibody titer specific for each of the at least seven serotypes of *S. pneumonia* that is two-fold or higher (e.g., 3-25 fold or more higher) than the opsonophagocytic antibody titer specific for each of the at least seven serotypes of *S. pneumonia* present in a control sample (e.g., immune globulin prepared from plasma pooled from 1000 or more random non-vaccinated human plasma donors). The invention also provides a hyperimmune globulin prepared according the above described method. Hyperimmune globulin so prepared can be used in various methods. For example, the hyperimmune globulin can be used in a method of treating *S. pneumonia* infection in a subject comprising administering to the subject a therapeutically effective amount of the hyperimmune globulin. The hyperimmune globulin can also be used in a method of providing immunotherapy to a subject comprising administering to the subject a therapeutically effective amount of the hyperimmune globulin.

In some embodiments, the invention provides a method of preparing compositions (e.g., blood, plasma, and/or immune globulin (e.g., hyperimmune globulin) compositions) containing a high titer of opsonic, anti-pneumococcal antibodies involving screening plasma (e.g., pools of plasma or immunoglobulin; immunoglobulin or immunoglobulin preparations) for total anti-pneumococcal binding antibodies using an in vitro antigen-binding assay (e.g., using an ELISA) together with an opsonophagocytic killing assay (e.g., an opsonophagocytic killing assay described herein or known in the art). In some embodiments, the invention provides a method of preparing compositions (e.g., blood, plasma, and/or immune globulin compositions) containing a high titer of opsonic, anti-pneumococcal antibodies involving screening plasma (e.g., pools of plasma or immunoglobulin; immunoglobulin or immunoglobulin preparations) for total anti-pneumococcal opsonic antibody titer using an opsonophagocytic bactericidal assay (e.g., an assay described in Example 1). In another embodiment, the invention provides a method of preparing compositions (e.g., blood, plasma, and/or immune globulin compositions) containing a high titer of opsonic, anti-pneumococcal antibodies involving screening plasma (e.g., pools of plasma or immunoglobulin; immunoglobulin or immunoglobulin preparations) for total anti-pneumococcal binding antibodies using an in vitro antigen-binding assay (e.g., using an ELISA) followed by screening the plasma (e.g., pools of plasma or immunoglobulin; immunoglobulin or immunoglobulin preparations) for total anti-pneumococcal opsonic antibody titer using an opsonophagocytic bactericidal assay (e.g., an assay described in Example 1). In a further embodiment, protective efficacy can be documented in vivo by analyzing protective activity of the compositions (e.g., blood, plasma, and/or immune globulin compositions) containing a high titer of opsonic, anti-pneumococcal antibodies using an animal model of *S. pneumonia* infection (e.g., to determine morbidity, mortality, and/or bacterial clearance). The invention is not limited by the method or assay used to measure the opsonophagocytic titer of antibody present. Indeed, a variety of assays may be used including, but not limited to, those described herein (e.g., in Example 1).

The invention provides a method, in one embodiment, of generating a composition comprising obtaining plasma samples from donors (e.g., 50, 100, 300, 500, 1000 or more donors (e.g., healthy adult human plasma donors)) vaccinated with one or more anti-pneumococcal vaccines and pooling the plasma samples (e.g., with each other and/or with plasma from non-vaccinated donors) to generate a pooled plasma composition. In a further embodiment, immune globulin is prepared from the pooled plasma samples (e.g., immune globulin is fractionated, purified, and/or isolated from plasma via any method known in the art including those described herein). In a further embodiment, immune globulin of the invention is rendered intravenously injectable (e.g., via providing the immune globulin in solution, adjusting the pH, adjusting the ionic strength, etc.). As described herein, in one embodiment, a pooled plasma composition of the invention contains an opsonophagocytic antibody titer that is at least 2-fold, 3-fold, 4-fold, 5-fold, 7-fold, 10-fold, or more greater for at least about 55% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) compared to the anti-pneumococcal-specific, opsonic antibody titers for the same serotypes present in a control sample (e.g., immune globulin prepared from plasma pooled from 1000 or more random non-vaccinated human plasma donors). In another embodiment, the pooled plasma composition contains an opsonophagocytic antibody titer specific for 70% or more of the *S. pneumonia* serotypes selected from serotypes 4, 6B, 9V, 14, 18C, 19F, and 23, that is 2 fold or greater (e.g., 3-25 fold or greater) than the titer of opsonic antibodies specific for the same *S. pneumonia* serotypes present in a control sample (e.g., immune globulin prepared from plasma pooled from 1000 or more random non-vaccinated human plasma donors). In yet another embodiment, the pooled plasma composition contains an opsonophagocytic antibody titer between 1:64 and 1:8192 (e.g., for at least 50% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) as determined by an opsonophagocytic killing assay described herein.

In one embodiment, plasma samples (e.g., from vaccinated and/or non-vaccinated donors) are screened in order to confirm the absence of blood-borne pathogens (e.g., before or after pooling). In some embodiments, plasma and/or antibody samples are obtained from donor subjects in the form of donated or purchased biological material (e.g., blood or plasma). In some embodiments, plasma and/or antibody samples (e.g., blood, plasma, isolated antibodies, etc.) are obtained from a commercial source. In some embodiments, a plasma and/or antibody sample, blood donation, or plasma donation is screened for pathogens, and either cleaned or discarded if particular pathogens are present. In some embodiments, screening occurs prior to pooling a donor sample with other donor samples. In other embodiments, screening occurs after pooling of samples. Antibodies, blood, and/or plasma may be obtained from any suitable subjects. In some embodiments, antibodies, blood, and/or plasma are obtained from a subject who has recently (e.g., within 1 year, within 6 months, within 2 months, within 1 month, within 2 weeks, within 1 week, within 3 days, within 2 days, within 1 day) been vaccinated against or been exposed to one or more pneumococcal vaccines.

In some embodiments, blood, plasma and/or immune globulin samples identified (e.g., according to methods described herein) as containing a high titer of opsonic, anti-pneumococcal antibodies are combined (e.g., pooled) to produce a composition of the invention (e.g., hyperimmune globulin) comprising a high titer of opsonic, anti-pneumococcal antibodies.

Any suitable method for obtaining plasma, antibody samples, pooled plasma compositions and/or immunoglobulin from same are within the scope of the present invention. Further, any suitable method for producing, manufacturing, purifying, fractionating, enriching, etc. antibody samples and/or plasma pools is within the bounds of the present invention.

Exemplary techniques and procedures for collecting antibody samples and producing plasma pools are provide, for example, in: U.S. Pat. Nos. 4,174,388; 4,346,073; 4,482,483; 4,587,121; 4,617,379; 4,659,563; 4,665,159; 4,717,564; 4,717,766; 4,801,450; 4,863,730; 5,505,945; 5,582,827; 6,692,739; 6,962,700; 6,984,492; 7,045,131; 7,488,486; 7,597,891; 6,372,216; U.S. patent App. No. 2003/0118591; U.S. patent App. No. 2003/0133929 U.S. patent App. No. 2005/0053605; U.S. patent App. No. 2005/0287146; U.S. Patent App. No. 2006/0110407; U.S. patent App. No. 2006/0198848; U.S. patent App. No. 2006/0222651; U.S. patent App. No. 2007/0037170; U.S. patent App. No. 2007/0249550; U.S. patent App. No. 2009/0232798; U.S. patent App. No. 2009/0269359; U.S. patent App. No. 2010/0040601; U.S. patent App. No. 2011/0059085; and U.S. patent App. No. 2012/0121578; herein incorporated by reference in their entireties. Embodiments of the present invention may utilize any suitable combination of techniques, methods, or compositions from the above listed references.

Isolated immune globulin of the invention may be of the IgG fraction or isotype, but isolated immune globulin is not restricted to any particular fraction or isotype and may be IgG, IgM, IgA, IgD, IgE, or any combination thereof. It is also preferable that the isolated immune globulin be purely or antigenically human immune globulin.

In one embodiment, a composition comprising high titer of opsonic, anti-pneumococcal antibodies of the invention is a sterile solution with a pH of about 6.0-7.8 (e.g., 5.0-6.0, 6.0, 6.1, 6.2, 6.3, 6.4, 6.5, 6.6, 6.7, 6.8, 6.9, 7.0, 7.1, 7.2, 7.3, 7.4, 7.5, 7.6. 7.7, 7.8, or higher). In another embodiment, a composition comprising high titer of opsonic, anti-pneumococcal antibodies of the invention is prepared according US FDA standards for immune globulin preparation (see e.g., 37

CFR §§ 640.100; 640.101; 640.102; 640.103; 640.104, Apr. 1, 2013). In one embodiment, a composition comprising high titer of opsonic, anti-pneumococcal antibodies of the invention (e.g., hyperimmune globulin described herein, in particular, in the Examples) possesses at least the minimum level of antibody titers to *Corynebacterium diphtheria*, measles virus, and polio virus recommended by the FDA (e.g., see 37 CFR § 640.104) for treating patients with immune deficiency disease.

In one embodiment, the pooled plasma composition lacks detectable levels (e.g., detected using any method known in the art (e.g., recommended by the U.S. Food and Drug Administration)) of human immunodeficiency virus (HIV) 1 (HIV-1), HIV-2, *Treponema pallidum, Plasmodium falciparum, Plasmodium malariae, Plasmodium ovale, Plasmodium vivax, Plasmodium knowlesi*, hepatitis B virus(HBV), hepatitis C virus (HCV), prions, West Nile virus, parvovirus, *Typanosoma cruzi*, SARS coronavirus, and/or vaccinia virus. In one embodiment, each individual plasma sample used in a process or composition of the invention is collected only at an FDA approved blood establishments and is tested by serological tests (e.g., FDA approved serological tests) for human immunodeficiency virus (HIV) 1 (HIV-1), HIV-2, *Treponema pallidum, Plasmodium falciparum, Plasmodium malariae, Plasmodium ovale, Plasmodium vivax, Plasmodium knowlesi*, hepatitis B virus(HBV), hepatitis C virus (HCV), prions, West Nile virus, parvovirus, *Typanosoma cruzi*, SARS coronavirus, and/or vaccinia virus. In another embodiment, an individual plasma sample and/or a pooled plasma composition of the invention is tested for the presence of HIV-1, HIV-2, HBV, HCV, or other infectious agent (e.g., pathogen) using Nucleic Acid Testing (NAT) and used in a process or composition of the invention only when the absence of the pathogens is confirmed.

The invention is not limited by the type of subject (e.g., mammal, non-human primate, human, etc.) administered or treated with a composition of the invention (e.g., pooled plasma samples and/or immunotherapeutic composition comprising same). For example, the invention is not limited by the type of patient receiving a compositions (e.g., blood, plasma, and/or immune globulin (e.g., hyperimmune globulin) compositions) containing a high titer of opsonic, anti-pneumococcal antibodies. It is an object of the invention to provide and/or administer a composition of the invention to immunocompromised patients described herein.

In one embodiment, the pooled plasma comprises plasma samples obtained from 1000-3000 or more (e.g., more than 1000, 1250, 1500, 1750, 2000, 2500, 3000, 3500, 4000 or more) human subjects. In one embodiment, the composition comprising pooled plasma samples further comprises a pharmaceutically acceptable carrier (e.g., natural and/or non-naturally occurring carriers). In one embodiment, the pooled plasma composition is utilized to prepare immune globulin (e.g., for intravenous administration to a subject). In one embodiment, the pooled plasma composition and/or immune globulin provides a therapeutic benefit to a subject administered the composition that is not achievable via administration of a mixture of plasma samples obtained from 1000 or more random human subjects and/or immunoglobulin prepared from same (e.g., prevents or treats upper respiratory infection in a subject not prevented or treated with conventional IVIG). The invention is not limited by the type of therapeutic benefit provided. Indeed, a variety of therapeutic benefits may be attained including those described herein.

In one embodiment, the pooled plasma and/or immunoglobulin prepared from same of the invention reduces the incidence of infection (e.g., upper respiratory tract infection) in a subject administered the composition. In another embodiment, a pooled plasma and/or immunoglobulin prepared from same of the invention reduces the number of days a subject administered the pooled plasma and/or immunoglobulin of the invention is required to be administered antibiotics (e.g., to treat infection (e.g., upper respiratory tract infection)). In yet another embodiment, a pooled plasma and/or immunoglobulin prepared from same of the invention increases the trough level of circulating opsonic anti-pneumococcal antibodies in a subject (e.g., increases the level of opsonic antibody titer specific for *S. pneumonia* (e.g., thereby providing protective levels of anti-pneumococcal specific antibodies between scheduled dates of administration of the pooled plasma and/or immune globulin prepared from same of the invention (e.g., that are not maintained in a subject administered conventional IVIG))).

Additional objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows the pneumococcal serotype specific IgG antibody binding titers in individual vaccinated donor sera drawn at the following time points: immediately prior to primary PREVNAR vaccination (Pre), immediately prior to secondary PNEUMOVAX23 vaccination at week 4 (Week 4), at week 8, at week 10, at week 12 and at week 16. The average pneumococcal serotype specific IgG antibody binding titers are shown for pre and weeks 4, 8, 10, and 12, and for pooled pre and week 12. The fold increase in pneumococcal serotype specific IgG antibody binding titers between pre and week 12 are also shown.

FIG. 2 shows the pneumococcal serotype specific opsonic killing (OPK) titer in individual vaccinated donor sera drawn at the following time points: immediately prior to primary PREVNAR vaccination (Pre), immediately prior to secondary PNEUMOVAX23 vaccination at week 4 (Week 4), at week 8, at week 10, at week 12 and at week 16, specific to various pneumococcal serotypes. The average pneumococcal serotype specific opsonic titers are shown for pre and weeks 4, 8 , 10, and 12, and for pooled pre and week 12. The fold increase in pneumococcal serotype specific OPK titers between pre and week 12 are also shown.

FIG. 3 shows the pneumococcal serotype specific IgG antibody binding titer in pooled donor sera pooled from 40 subjects which were drawn at the following time points: immediately prior to primary PREVNAR vaccination (Pre), at week 8, at week 10, at week 12 and at week 16, and at month 5.

FIG. 4 shows the fold increase in pneumococcal serotype specific IgG antibody binding concentrations in pooled donor sera drawn at the following time points: immediately prior to primary PREVNAR vaccination (Pre), at week 8, at week 10, at week 12 and at week 16, and at month 5. (*=baseline).

FIG. 5 shows the pneumococcal serotype specific opsonic killing (OPK) titers in pooled donor sera pooled from 40 subjects which were drawn at the following time points:

Figure 9A:
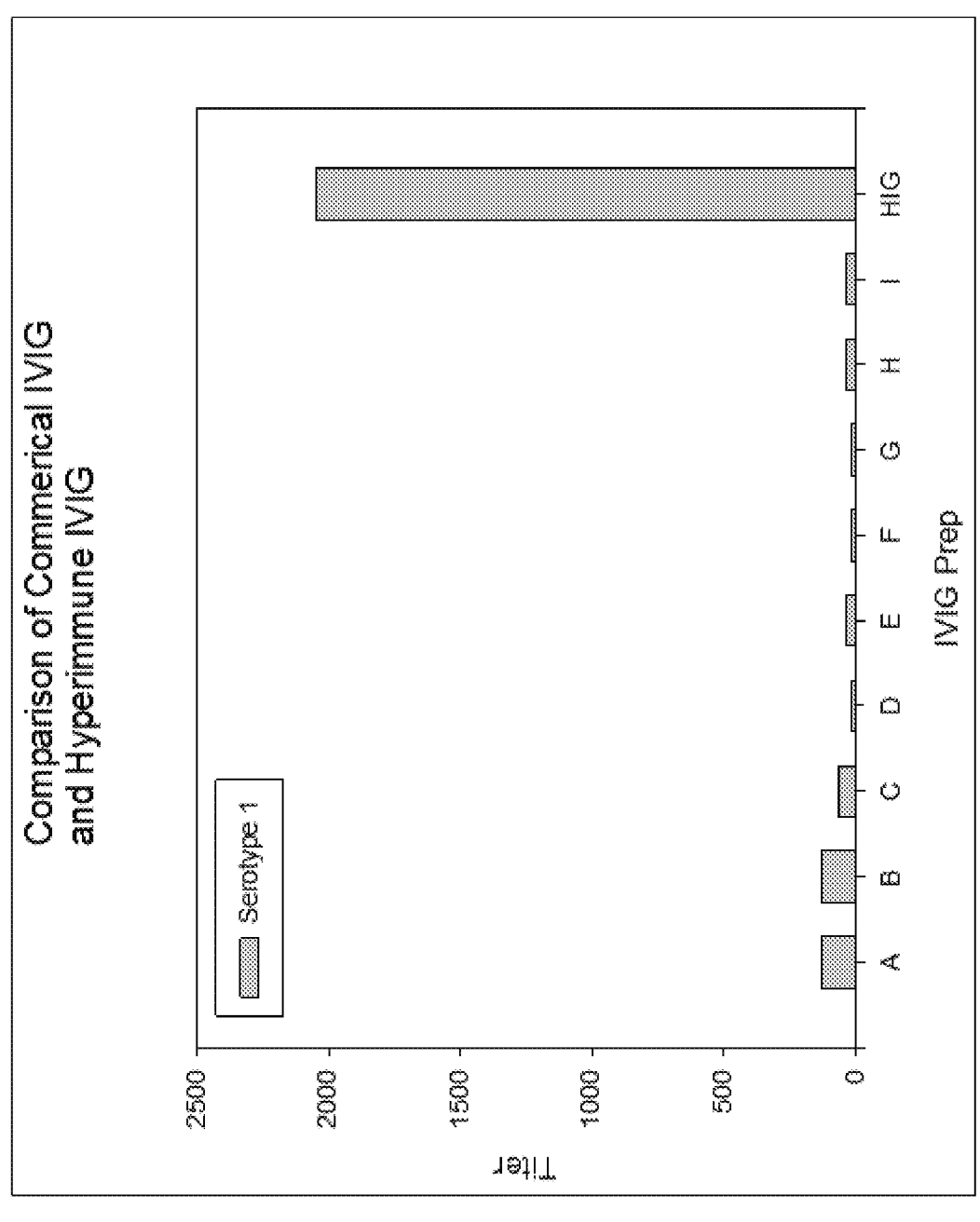

immediately prior to primary PREVNAR vaccination (Pre), at week 8, at week 10, at week 12 and at week 16, and at month 5.

FIG. 6 shows the pneumococcal serotype specific IgG antibody binding concentrations in purified immune globulin (IG) from pooled donor sera pooled from 40 individuals which were drawn at the indicated time points.

FIG. 7 shows the pneumococcal serotype specific OPK titers in purified IgG from pooled donor sera pooled from 40 individuals which were drawn at the indicated time points.

FIG. 8 shows a comparison of the OPK serotype specific titer of functional/opsonic antibodies present in pooled human sera from vaccinated donors versus the OPK serotype specific titer of functional/opsonic antibodies present in multiple different conventional, commercially available IVIG. Each column represents a single, unique *S. pneumonia* serotype. Each row represents a unique sample. Samples A-I represent different lots of conventional, commercially available IVIG. "IVIG Average" is the average OPK serotype specific titer of functional/opsonic antibodies present in a pooled sample containing equal amounts of each conventional, commercially available IVIG. "Donor sera pre-vaccination" represents the OPK serotype specific titer of functional/opsonic antibodies present in pooled human donor sera pre-vaccination described in Example 1. "Vaccinated donor sera" represents the OPK serotype specific titer of functional/opsonic antibodies present in pooled human donor sera at twelve weeks post vaccination described in Example 1. "Fold Titer Increase over commercial IVIG" represents the fold increase in OPK serotype specific titer of functional/opsonic antibodies present in pooled human donor sera at twelve weeks post vaccination described in Example 1 versus the average OPK serotype specific titer of functional/opsonic antibodies present in a pooled sample containing equal amounts of each conventional, commercially available IVIG.

Figure 9B:
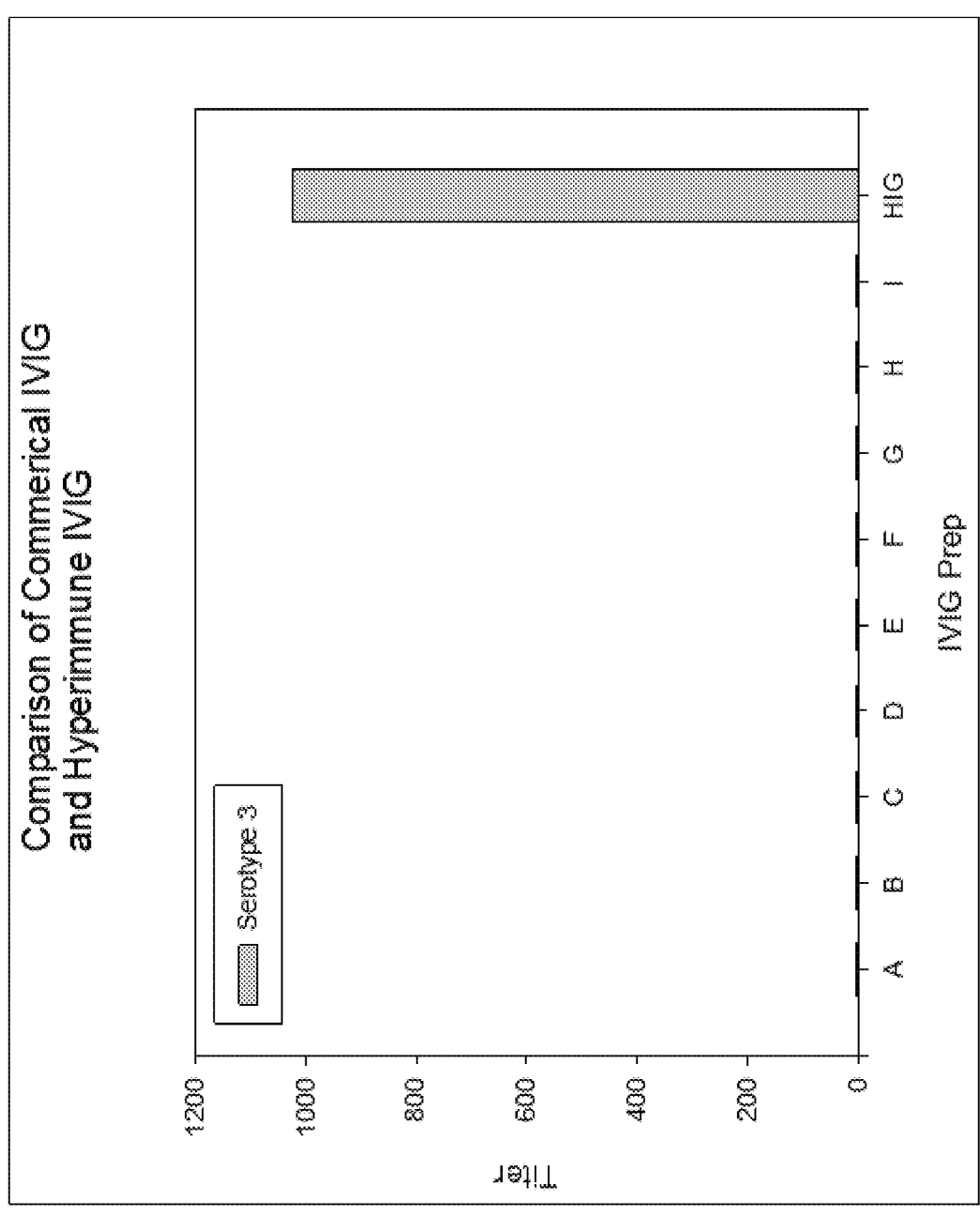
Figure 9C:
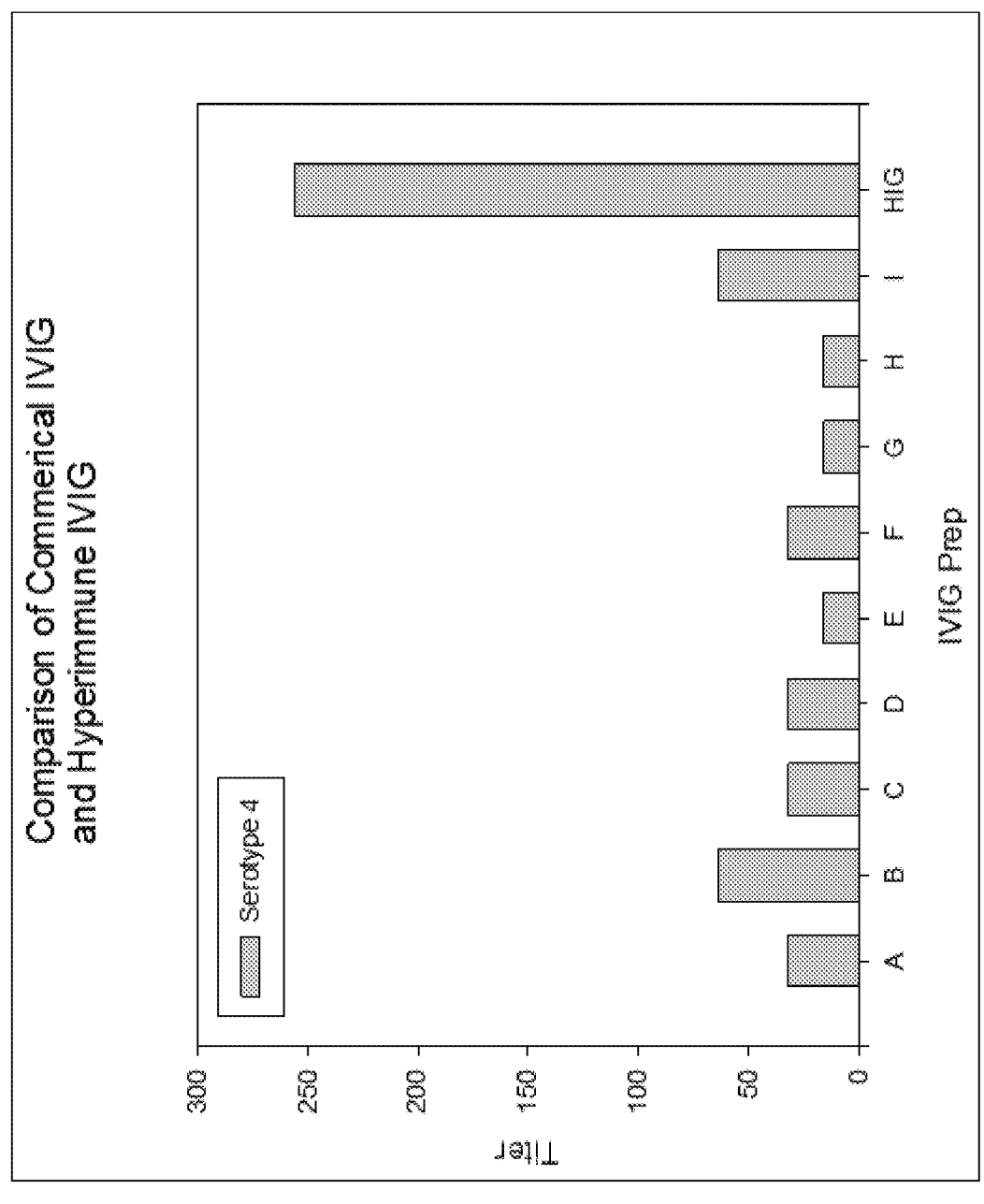
Figure 9D:
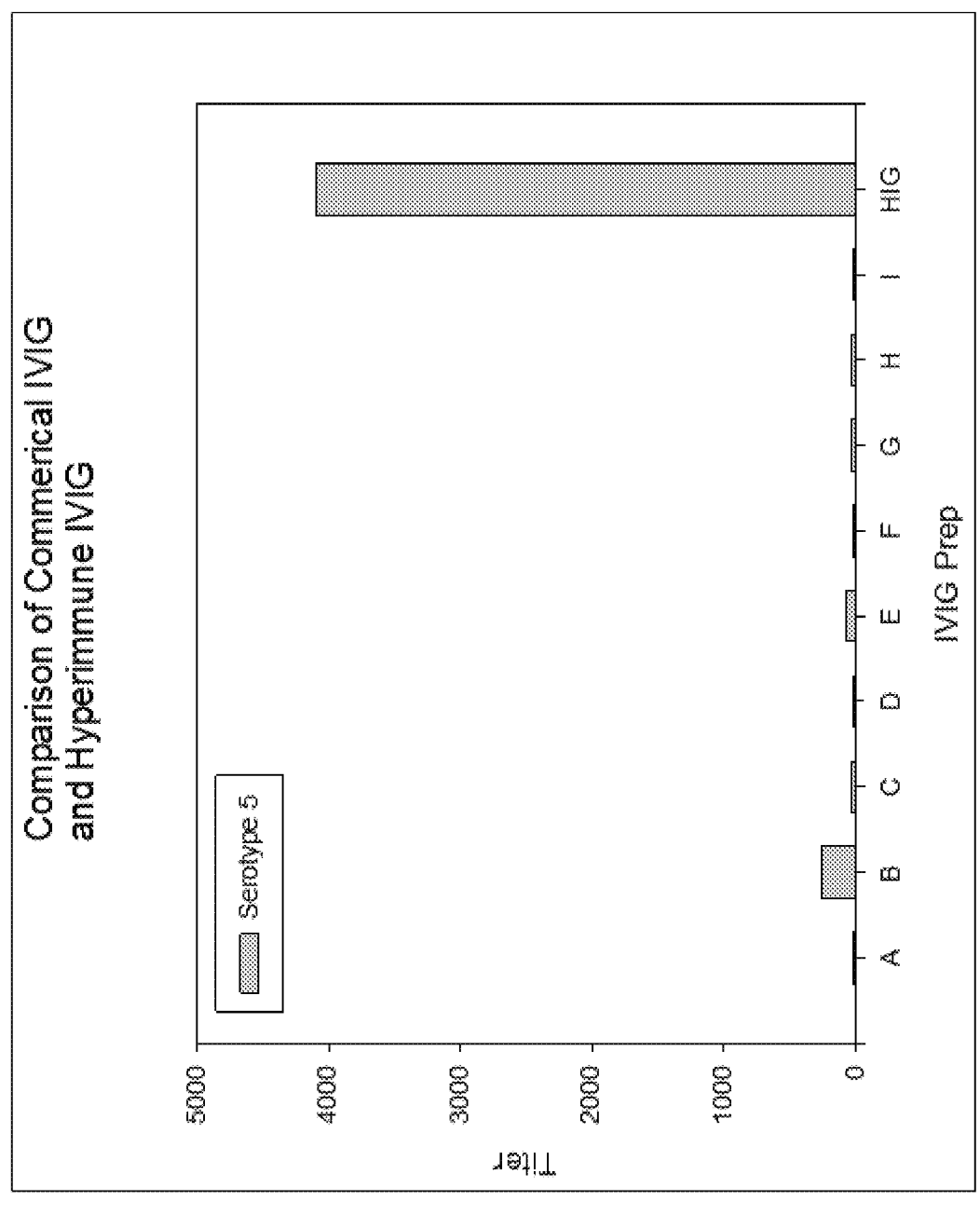
Figure 9E:
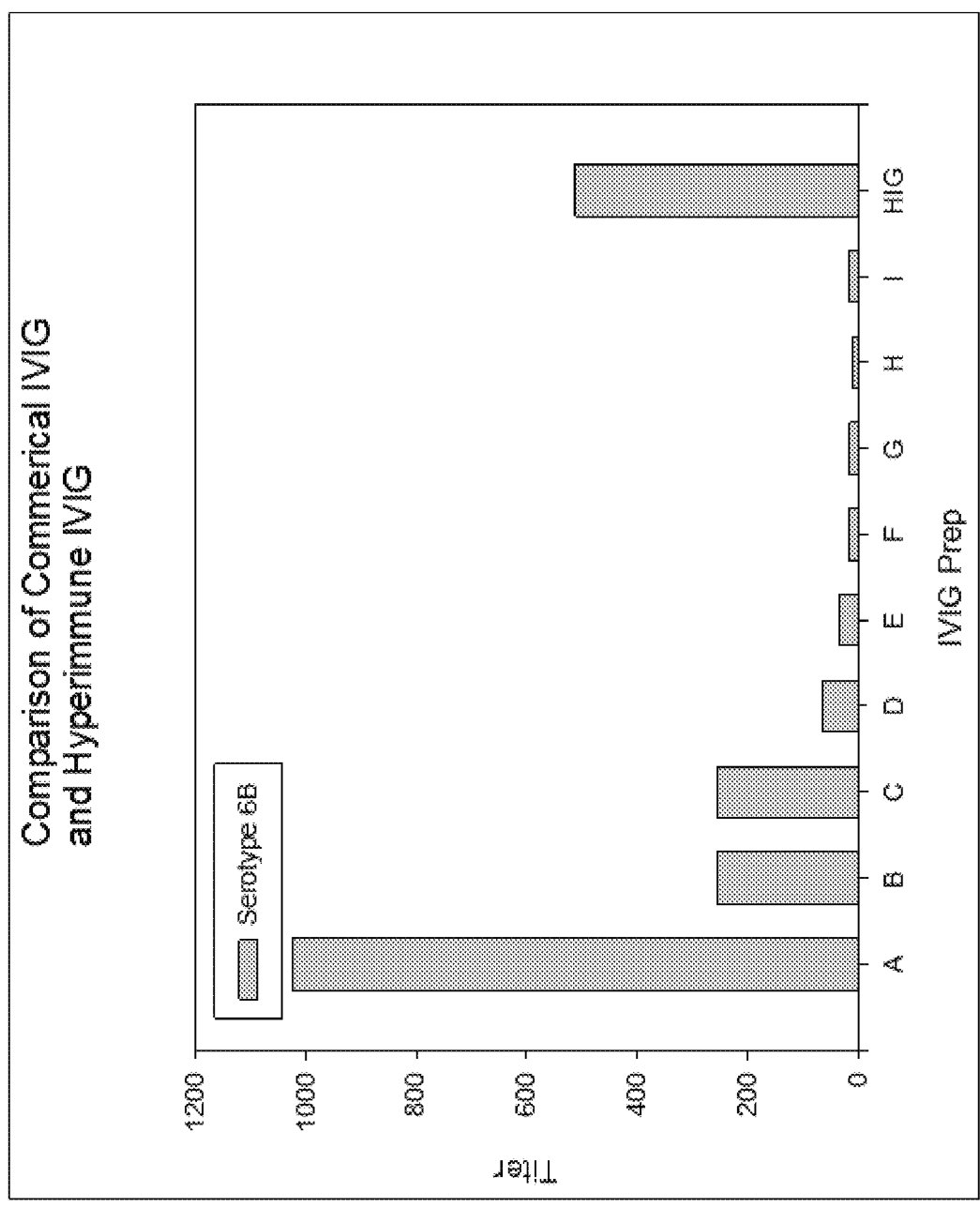
Figure 9F:
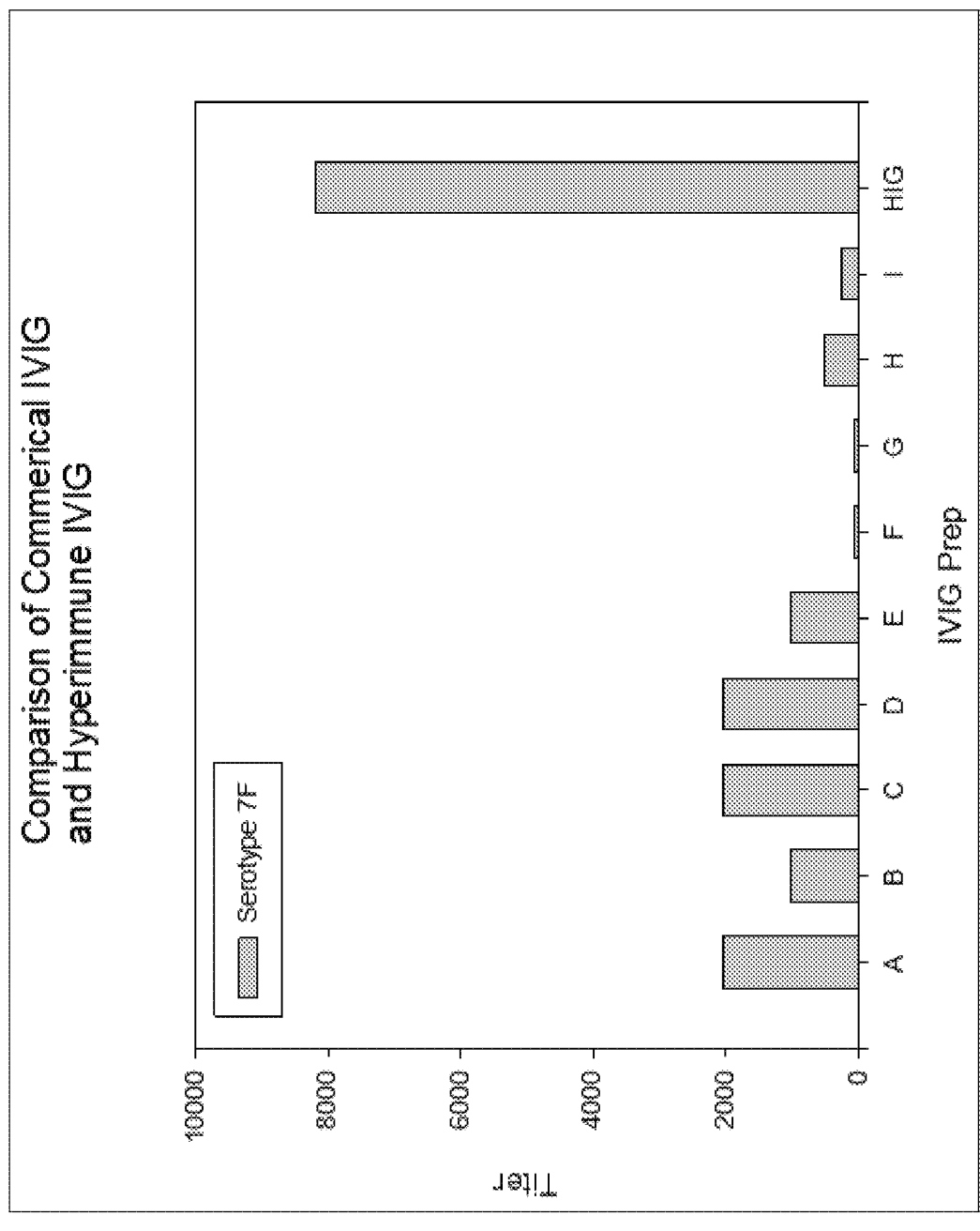
Figure 9G:
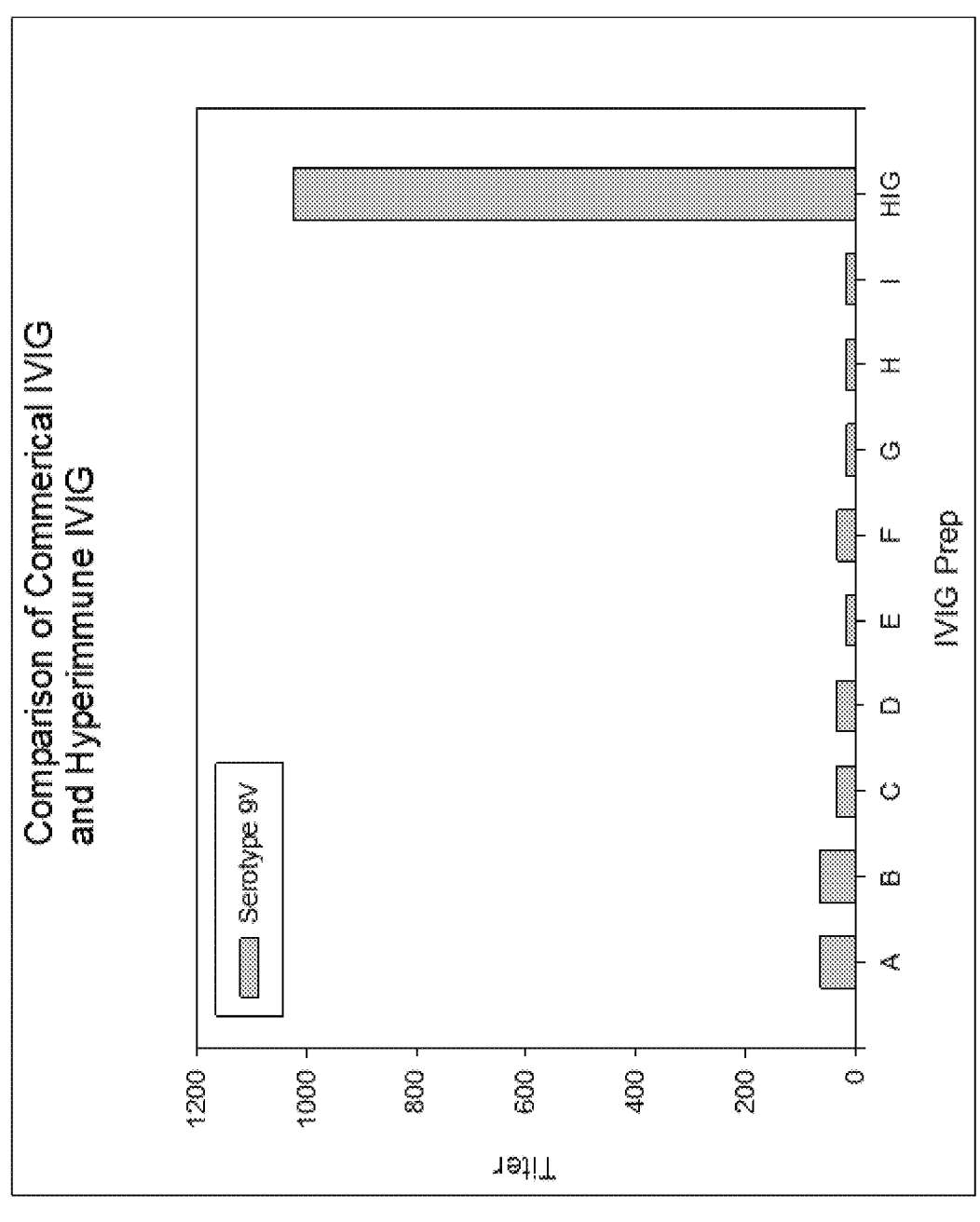
Figure 9H:
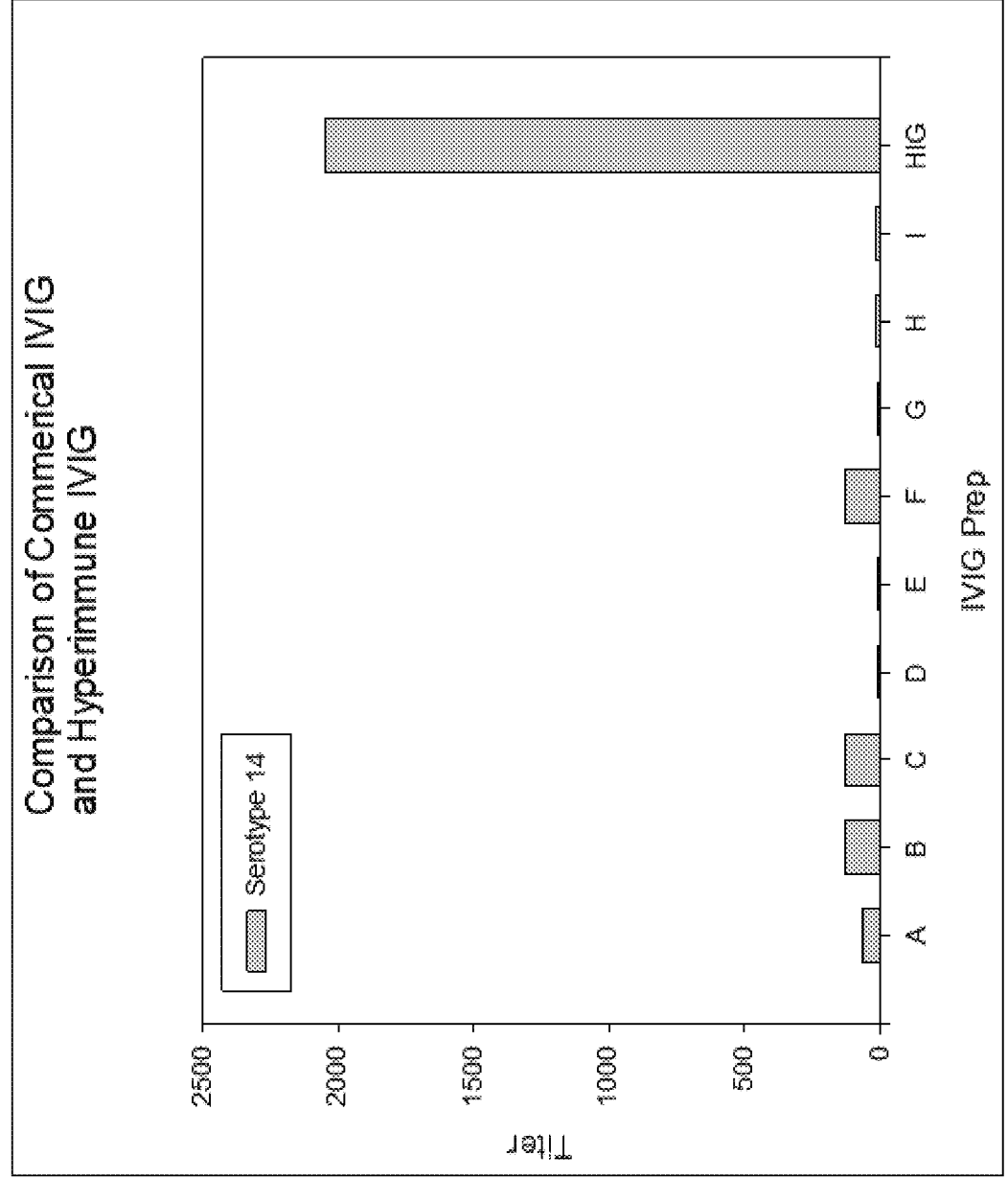
Figure 9I:
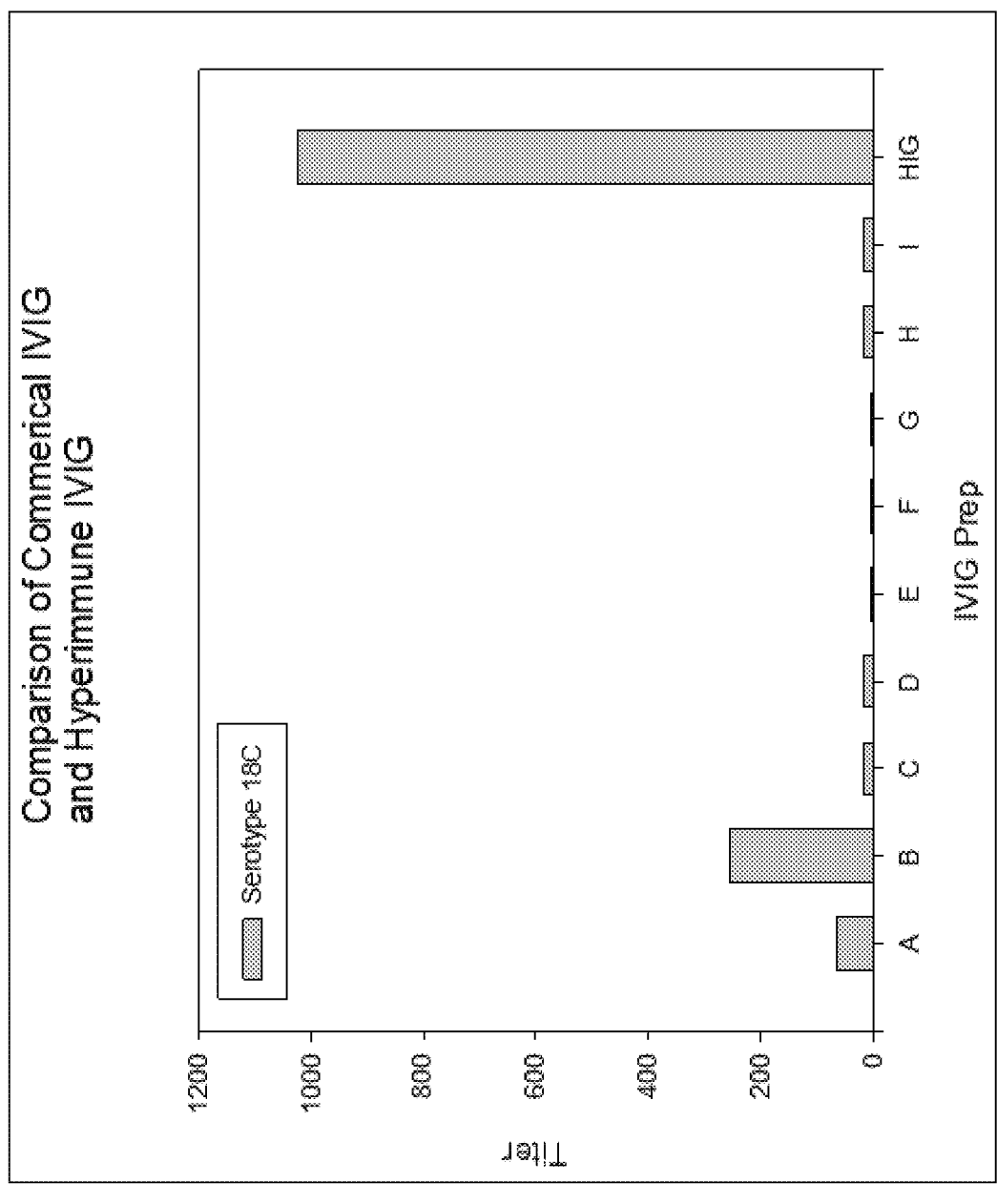
Figure 9J:
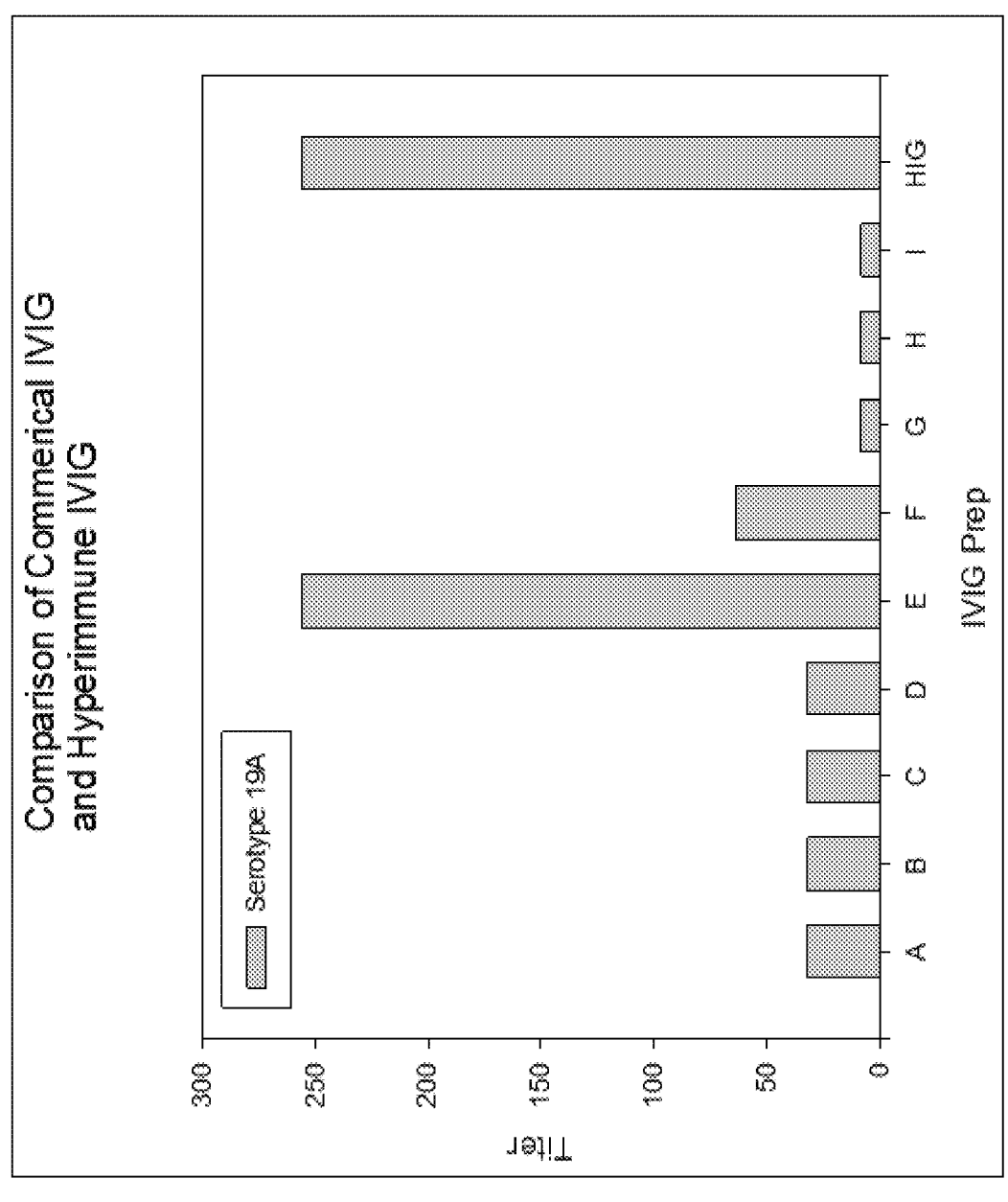
Figure 9K:
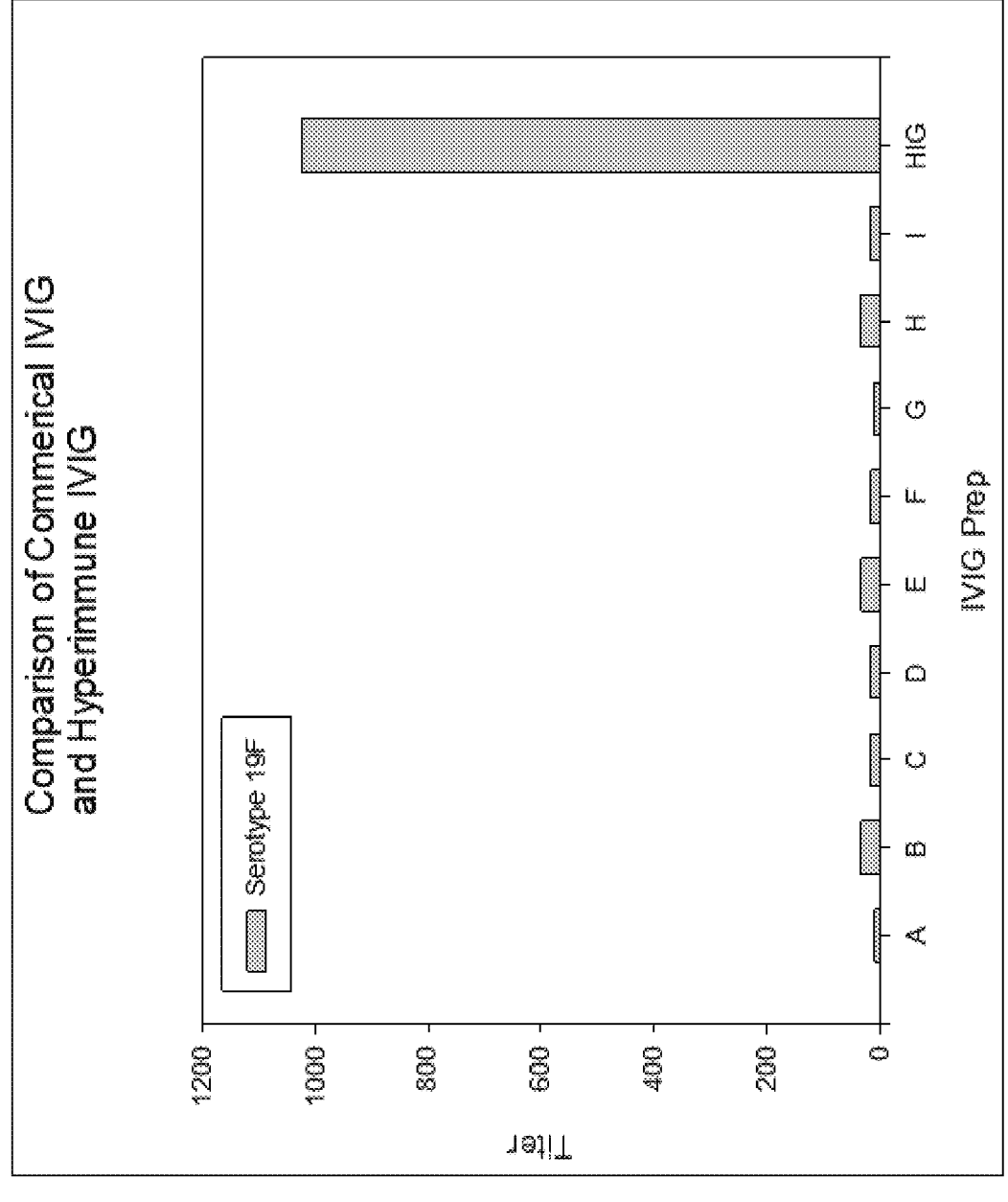
Figure 9L:
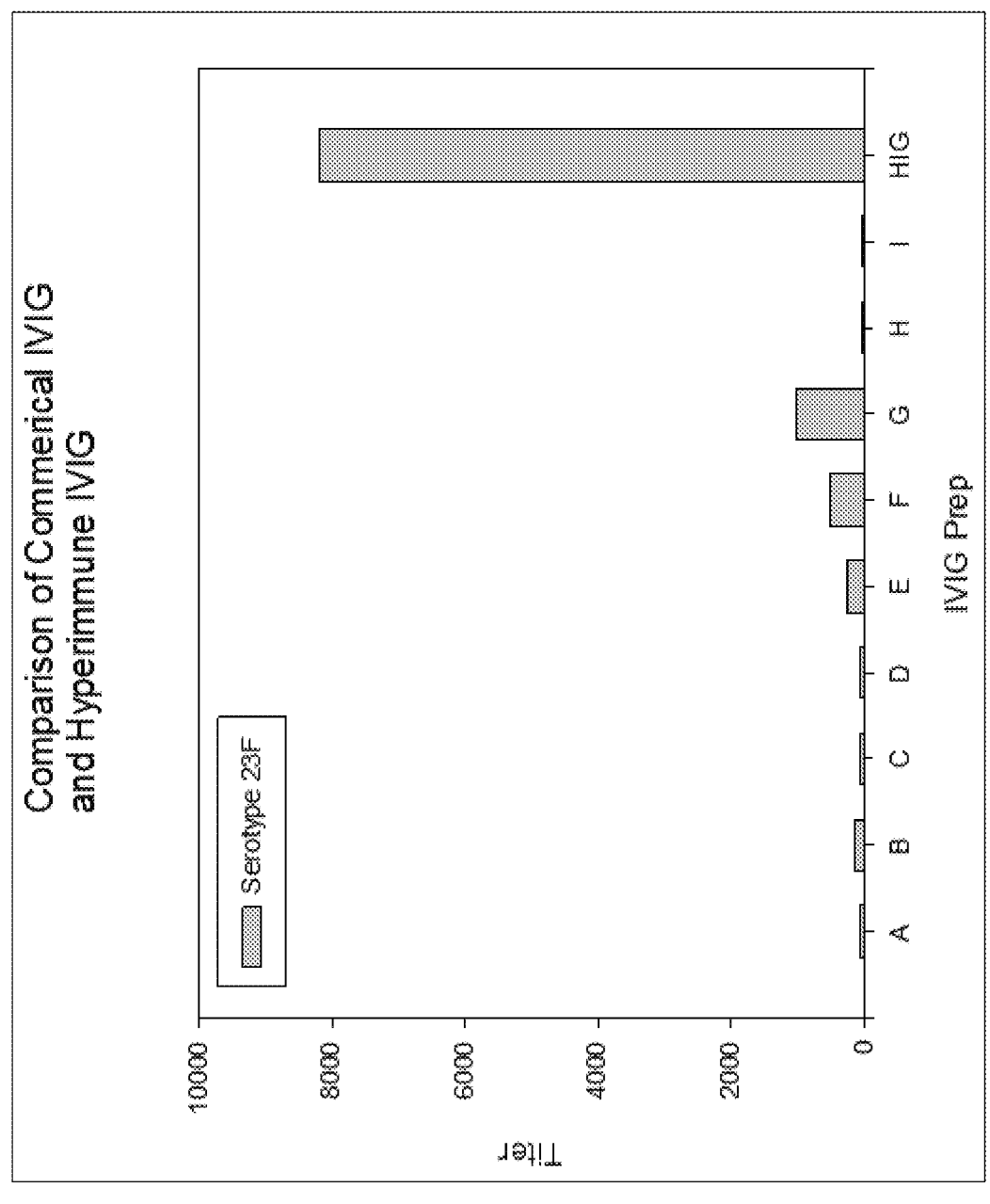

FIGS. 9A-9L depict the *S. pneumonia* serotype specific opsonic antibody titer present in nine different commercial lots of IVIG (samples A-I) compared to the *S. pneumonia* serotype specific opsonic antibody titer present in hyperimmune globulin of the invention containing a high titer of opsonic, anti-pneumococcal antibodies to each serotype.

FIG. 10 shows the percentage of subjects with primary immune deficiency disease that fall below protective levels (1.2 mg/ml) of anti-*S pneumonia* binding antibodies at trough after infusion of conventional IVIG.

DEFINITIONS

As used herein, the term "subject" refers to any human or animal (e.g., non-human primate, rodent, feline, canine, bovine, porcine, equine, etc.).

As used herein, the term "sample" is used in its broadest sense and encompass materials obtained from any source, and may be used, for example, to refer to materials obtained from a biological source, for example, obtained from animals (including humans), and further encompasses any fluids, solids and tissues. In particular embodiments of this invention, biological samples include blood and blood products such as plasma, serum and the like. However, these examples are not to be construed as limiting the types of samples that find use with the present invention.

As used herein, the term "antibody" refers to an immunoglobulin molecule that is typically composed of two identical pairs of polypeptide chains, each pair having one "light" (L) chain and one "heavy" (H) chain. Human light chains are classified as kappa and lambda light chains.

Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 3 or more amino acids. Each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$. Each light chain is comprised of a light chain variable region (abbreviated herein as LCVR or $V_L$) and a light chain constant region. The light chain constant region is comprised of one domain, CL. The constant regions of the antibodies may mediate the binding of the immunoglobulin to host tissues or factors, including various cells of the immune system (e.g., effector cells) and the first component (C1q) of the classical complement system. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of each heavy/light chain pair ($V_H$ and $V_L$), respectively, form the antibody binding site. The term "antibody" encompasses an antibody that is part of an antibody multimer (a multimeric form of antibodies), such as dimers, trimers, or higher-order multimers of monomeric antibodies. It also encompasses an antibody that is linked or attached to, or otherwise physically or functionally associated with, a non-antibody moiety. Further, the term "antibody" is not limited by any particular method of producing the antibody. For example, it includes, inter alia, recombinant antibodies, synthetic antibodies, monoclonal antibodies, polyclonal antibodies, bi-specific antibodies, and multi-specific antibodies.

As used herein, the term "antibody derivative" or "derivative" of an antibody refers to a molecule that is capable of binding to the same antigen that the antibody from which it is derived binds to and comprises an amino acid sequence that is the same or similar to the antibody linked to an additional molecular entity. The amino acid sequence of the antibody that is contained in the antibody derivative may be the full-length antibody, or may be any portion or portions of a full-length antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional entity by chemical coupling, genetic fusion, noncovalent association or otherwise. The term "antibody derivative" also encompasses chimeric antibodies, humanized antibodies, and molecules that are derived from modifications of the amino acid sequences of an antibody, such as conservation amino acid substitutions, additions, and insertions.

As used herein, the terms "antigen" and "immunogen" are used interchangeably to refer to any substance that is capable of inducing an adaptive immune response. An antigen may be whole cell (e.g. bacterial cell), virus, fungus, or an antigenic portion or component thereof. Examples of antigens include, but are not limited to, microbial pathogens, bacteria, viruses, proteins, glycoproteins, lipoproteins, peptides, glycopeptides, lipopeptides, toxoids, carbohydrates, tumor-specific antigens, and antigenic portions or components thereof.

As used herein, the term "antigen-binding fragment" of an antibody refers to one or more portions of a full-length antibody that retain the ability to bind to the same antigen that the antibody binds to.

As used herein, the terms "immunoglobulin," "immune globulin," "immunoglobulin molecule" and "IG" encompass (1) antibodies, (2) antigen-binding fragments of an antibody, and (3) derivatives of an antibody, each as defined herein. As described herein, immune globulin may be prepared from (e.g., fractionated from, isolated from, purified from, concentrated from, etc.) pooled plasma compositions (e.g., for administration to a subject). As used herein, the term "intravenous immune globulin (IVIG)" refers to conventional immunoglobulin prepared from the plasma of large numbers (e.g., 250, 500, 1000, or more) random human donors (e.g., HIZENTRA, Immune Globulin Subcutaneous, CSL Behring), whereas the terms "anti-pneumococcal immune globulin" or "anti-pneumococcal IVIG" or "anti-pneumococcal hyper-immune globulin" (e.g., as described herein and in the Examples), refers to immune globulin prepared from plasma donors (e.g., human plasma donors) according to methods of the invention (e.g., large numbers (e.g., 250, 500, 1000, or more) human plasma donors (e.g., healthy human plasma donors) that have been vaccinated with one or more anti-pneumococcal vaccines according to methods described herein), that contains an elevated anti-pneumococcal-specific, opsonic antibody titer when compared to a control sample.

The terms "opsonophagocytic antibody" and "opsonic antibody" are used interchangeably herein to refer to antibodies that function to actively cause bacteria or other foreign matter (e.g., cells or cell products) to become susceptible to the action of phagocytes (e.g., opsonic antibodies coat bacteria in turning causing the bacterial cells to become susceptible to phagocytosis due to interaction between the opsonic antibodies coating the bacterial cells and receptors present on the surface of phagocytes). For example, an opsonic anti-pneumococcal antibody is an antibody that binds to and coats the surface of S. pneumonia and causes the bacterium to become susceptible to phagocytosis/killing by phagocytes.

The terms "opsonophagocytic antibody titer" and "opsonic antibody titer" are used interchangeably herein to refer to the titer of functionally active opsonophagocytic antibodies (e.g., that correlate with protection against infection and/or disease). For example, an opsonic anti-pneumococcal antibody titer (e.g., measured by an OPK assay described herein) is the titer of opsonophagocytic antibodies specific for S. pneumonia in a sample (e.g., that is independent and distinct from the total amount of antibody capable of binding S. pneumonia present in the sample (e.g., measured by an ELISA assay).

As used herein, the term "hyperimmune globulin" refers to immunoglobulin prepared from the plasma of donors with high titers of antibody (e.g., opsonic antibody) against a specific organism (e.g., S. pneumonia). For example, as used herein, an "anti-pneumococcal hyperimmune globulin" is an immunoglobulin containing an elevated opsonic anti-pneumococcal antibody titer regardless of (e.g., that is independent and distinct from) the total titer or amount of antibody capable of binding S. pneumonia.

As described herein, an elevated opsonic anti-pneumococcal-specific antibody titer is one that is at least 2-fold, 3-fold, 4-fold, 5-fold, 7-fold, 10-fold, or more greater for at least about 55% or more (e.g., 60%, 65%, 70%, 75%, 80%, 85% or more) of S. pneumonia serotypes 1, 3, 4, 5, 6B, 7F, 9V, 14, 18C, 19A, 19F, and 23F) compared to the opsonic anti-pneumococcal-specific antibody titers for the same serotypes present in a control sample; or one that is specific for 70% or more of the S. pneumonia serotypes selected from serotypes 4, 6B, 9V, 14, 18C, 19F, and 23, and that is 2 fold or greater (e.g., 3-25 fold or greater) than the titer of opsonic antibodies specific for the same S. pneumonia serotypes present in a control sample; or one that is between 1:64 and 1:8192 (e.g., for at least 50% or more (e.g., 60%, 65%, 70%, 75%, 80%, 85% or more) of S. pneumonia serotypes 1, 3, 4, 5, 6B, 7F, 9V, 14, 18C, 19A, 19F, and 23F) as determined by an opsonophagocytic killing assay described herein; or one that is at least 2-fold, 3-fold, 4-fold, 5-fold or more greater than the opsonic anti-pneumococcal-specific antibody titer present in a control sample, e.g., for at least 55% or more of the pneumococcal serotypes selected from serotypes 1, 3, 4, 5, 6B, 7F, 9V, 14, 18C, 19A, 19F, and 23F (that is, at least 2-, 3-, 4-, 5-fold or more greater increase in the opsonic anti-pneumococcal-specific antibody titers specific for 7/12, 8/12, 9/12, 10/12, 11/12, or 12/12 of the pneumococcal serotypes compared to a control sample). The invention is not limited by the type of control sample utilized. For example, in one embodiment, a control sample is immune globulin prepared from the healthy human plasma donor(s) pre-vaccination (e.g., such that the pre-immunization levels of opsonic anti-pneumococcal-specific antibody titers of the human plasma donors are used as a baseline to measure the increase in the opsonic anti-pneumococcal-specific antibody titers post immunization). In another embodiment, a control sample is immune globulin prepared from a mixture of plasma samples obtained from 1000 or more random human plasma donors that have not been vaccinated with an anti-pneumococcal vaccine (e.g., such that the levels of opsonic anti-pneumococcal-specific antibody titers of the non-vaccinated human plasma donors are used as a baseline to measure the increase in the opsonic anti-pneumococcal-specific antibody titers present in human plasma donors vaccinated according to methods of the invention). Those of skill in the art will appreciate that other control samples may be utilized. An elevated opsonic anti-pneumococcal-specific antibody titer may also be a titer that is used to measure bacterial killing and/or one that is used as an accurate surrogate to predict the efficacy of an immuno-globulin preparation to protect against S. pneumonia infections.

As used herein, the phrase "pharmaceutically acceptable" refers to molecular entities and compositions that are physiologically tolerable and do not typically produce an unacceptable allergic or similar untoward reaction when administered to a human.

PNEUMOVAX (Merck Sharp & Dohme Corp., North Wales, PA) refers to pneumococcal polysaccharide vaccine composed of purified preparations of pneumococcal capsular polysaccharide. PPSV23 contains polysaccharide antigen from the following 23 types of pneumococcal bacteria: 1, 2, 3, 4, 5, 6B, 7F, 8, 9N, 9V, 10A, 11A, 12F, 14, 15B, 17F, 18C, 19F, 19A, 20, 22F, 23F, and 33F. It contains 25 µg of each antigen per dose and contains 0.25% phenol as a preservative.

PREVNAR-13 (Wyeth Pharmaceuticals, Collegeville, PA) refers to a pneumococcal conjugate vaccine that includes purified capsular polysaccharide of 13 serotypes of Streptococcus pneumonia (1, 3, 4, 5, 6A, 6B, 7F, 9V, 14, 19A, 19F, 18C, and 23F) conjugated to a nontoxic variant of diphtheria toxin known as CRM197. A 0.5-milliliter (mL)

PCV13 dose contains approximately 2.2 micrograms (µg) of polysaccharide from each of 12 serotypes and approximately 4.4 µg of polysaccharide from serotype 6B; the total concentration of CRM197 is approximately 34 µg. he vaccine contains 0.02% polysorbate 80 (P80), 0.125 milligrams (mg) of aluminum as aluminum phosphate (AlPO4) adjuvant, and 5 mL of succinate buffer. The vaccine does not contain thimerosal preservative.

As used herein, the term "antibody sample" refers to an antibody-containing composition (e.g., fluid (e.g., plasma, blood, purified antibodies, blood or plasma fractions, blood or plasma components etc.)) taken from or provided by a donor (e.g., natural source) or obtained from a synthetic, recombinant, other in vitro source, or from a commercial source. The antibody sample may exhibit elevated titer of a particular antibody or set of antibodies based on the pathogenic/antigenic exposures (e.g., natural exposure or through vaccination) of the donor or the antibodies engineered to be produced in the synthetic, recombinant, or in vitro context. Herein, an antibody sample with elevated titer of antibody X is referred to as an "X-elevated antibody sample." For example, an antibody sample with elevated titer of antibodies against S. pneumonia is referred to as a "S. pneumonia-elevated antibody sample."

As used herein, the term "isolated antibody" or "isolated binding molecule" refers to an antibody or binding molecule that is identified and separated from at least one contaminant with which it is ordinarily associated in its source. Examples of an isolated antibody include: an antibody that: (1) is not associated with one or more naturally associated components that accompany it in its natural state; (2) is substantially free of other proteins from its origin source; or (3) is expressed recombinantly, in vitro, or cell-free, or is produced synthetically and the is removed the environment in which it was produced.

As used herein, the terms "pooled plasma," "pooled plasma samples" and "pooled plasma composition" refer to a mixture of two or more plasma samples and/or a composition prepared from same (e.g., immune globulin). Elevated titer of a particular antibody or set of antibodies in pooled plasma reflects the elevated titers of the antibody samples that make up the pooled plasma. For example, plasma samples may be obtained from subjects that have been vaccinated (e.g., with a pneumococcal vaccine) and therefore have a high titer of antibody (e.g., high titer of total binding antibody and/or a high opsonic antibody titer) to a pathogen (S. pneumonia) as compared to the antibody level(s) found in the population as a whole. Upon pooling of the plasma samples, a pooled plasma composition is produced (e.g., that has elevated titer of antibodies specific to the particular pathogen). Herein, a pooled plasma with elevated titer of antibody X (e.g., wherein "X" is a microbial pathogen) is referred to as "X-elevated antibody pool." For example, a pooled plasma with elevated titer of binding antibodies against S. pneumonia is referred to as "S. pneumonia-elevated antibody pool." Pooled plasma compositions can be used to prepare immune globulin (e.g., that is subsequently administered to a subject) via methods known in the art (e.g., fractionation, purification, isolation, etc.). The invention provides that both pooled plasma compositions and immune globulin prepared from same may be administered to a subject to provide prophylactic and/or therapeutic benefits to the subject. Accordingly, the term pooled plasma composition may refer to immune globulin prepared from pooled plasma/pooled plasma samples.

As used herein, the term, "spiked antibody pool" refers to a pooled plasma spiked or combined with antibodies or other immunoglobulin produced synthetically, recombinantly, or through other in vitro means.

As used herein, the term "purified" or "to purify" means the result of any process that removes some of a contaminant from the component of interest, such as a protein (e.g., antibody) or nucleic acid. The percent of a purified component is thereby increased in the sample.

As used herein, the term "immunotherapeutic agents" refers to a chemical or biological substance that can enhance an immune response (e.g., specific or general) of a mammal. As used herein, the term "donor" refers to a subject that provides a biological sample (e.g., blood, plasma, etc.). A donor/donor sample may be screened for the presence or absence of specific pathogens (e.g., using U.S. Food and Drug Administration (FDA) guidelines for assessing safety standards for blood products (e.g., issued by the FDA Blood Products Advisory Committee). For example, a donor/donor sample may be screened according to FDA guidelines to verify the absence of one or more blood borne pathogens (e.g., human immunodeficiency virus (HIV) 1 (HIV-1), HIV-2; Treponema pallidum (syphilis); Plasmodium falciparum, P. malariae, P. ovale, P. vivax or P. knowlesi (malaria); hepatitis B virus(HBV), hepatitis C virus HCV); prions (Creutzfeldt Jakob disease); West Nile virus; parvovirus; Typanosoma cruzi; SARS coronavirus (SARS); vaccinia virus or other pathogen routinely screened or that is recommended to be screed for by a regulatory body such as the FDA).

As used herein, an "immunostimulatory amount" refers to that amount of a vaccine (e.g., anti-pneumococcal vaccine) that is able to stimulate an immune response. An immune response includes the set of biological effects leading to the body's production of immunoglobulins, or antibodies, in response to a foreign entity. Accordingly, immune response refers to the activation of B cells, in vivo or in culture, through stimulation of B cell surface Ig receptor molecules. The measurement of the immune response is within the ordinary skill of those in this art and includes the determination of antibody levels using methods described in the series by P. Tijssen, Laboratory Techniques in Biochemistry and Molecular Biology: Practice and Theory of Enzyme Immunoassays, (Burdon & van Knippenberg eds., 3rd ed., 1985) Elsevier, New York; and Antibodies: A Laboratory Manual, (Harlow & Lane eds., 1988), Cold Spring Harbor Laboratory Press; as well as procedures such as countercurrent immuno-electrophoresis (GIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530, all of which are incorporated by reference. Measurement of the immune response also includes detection or determination of B cell activation events that may precede antibody production, or signal an increase in antibody production. Such measurements include, B cell proliferation assays, phosphorylation assays, assays of intracytoplasmic free calcium concentration, and other methods of determining B cell activation known in the art. Representative assays are provided in Mongini et al., J. Immunol. 159:3782-91 (1997); Frade, et al., BBRC 188:833-842 (1992); Tsokos et al., J. Immunol. 144:1640-1645 (1990); Delcayre et al., BBRC 159:1213-1220 (1989); and Nemerow et al., J. Immunol. 135:3068-73 (1985) each of which is incorporated by reference. In preferred embodiments, the practice of the invention includes promoting, enhancing or stimulating an immune response. These actions refer to establishing an immune response that did not previously exist; to optimizing or increasing a desired immune response; to establishing or increasing a secondary response characterized by increased isotype switching, memory response, or both; to providing a statistically increased immunoprotective effect against a pathogen; to generating an equivalent or greater humoral immune response, or other measure of B cell activation, from a reduced or limiting dose of antigen; to generating an increased humoral immune response, or other measure of B cell activation, in response to an equivalent dose of antigen; or to lowering the affinity threshold for B cell activation in vivo or in vitro. Preferably, an immunostimulatory amount refers to that amount of vaccine that is able to stimulate an immune response in a subject (e.g., a donor), and from which subject plasma, serum or other blood component is harvested for use in the compositions and methods of the invention (e.g., for the therapeutic and/or prophylactic treatment of pneumococcal infection in a subject treated with compositions and methods described herein)).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "adjuvant" refers to any substance that can stimulate an immune response. Some adjuvants can cause activation of a cell of the immune system (e.g., an adjuvant can cause an immune cell to produce and secrete a cytokine). Examples of adjuvants that can cause activation of a cell of the immune system include, but are not limited to, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); cholera toxin (CT), and Leishmania elongation factor (a purified Leishmania protein; Corixa Corporation, Seattle, Wash.). Traditional adjuvants are well known in the art and include, for example, aluminum phosphate or hydroxide salts ("alum"). In some embodiments, compositions of the present invention are administered with one or more adjuvants (e.g., to skew the immune response towards a Th1 and/or Th2 type response). In some embodiments, an adjuvants described in US2005158329; US2009010964; US2004047882; or U.S. Pat. No. 6,262,029 (each of which is hereby incorporated by reference in its entirety) is utilized.

As used herein, the term "an amount effective to induce an immune response" (e.g., of a pneumococcal vaccine), refers to the dosage level required (e.g., when administered to a subject) to stimulate, generate and/or elicit an immune response in the subject. An effective amount can be administered in one or more administrations (e.g., via the same or different route), applications, or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethyl glycol, other natural and non-naturally occurring carries, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

DETAILED DESCRIPTION OF THE INVENTION

*Streptococcus pneumonia* is a leading cause of mortality and morbidity worldwide. Its major virulence factor is the capsular polysaccharide. Old age and antibody immunodeficiency (e.g., resulting from a primary immunodeficiency described herein) are the primary risk factors for pneumococcal infection. The World Health Organization (WHO) estimates that 1.6 million people die of pneumococcal diseases each year. Although most of the more than 90 known capsular serotypes can cause serious disease, a limited number cause the majority of cases of invasive pneumococcal disease (IPD). Immunity to *S. pneumonia* is mediated by phagocytosis of the bacteria in the presence of complement and serotype specific, opsonic antibody. Evaluation of serologic responses to different pneumococcal vaccines in large clinical trials has provided correlates of protection required to release new vaccines. For predicting protection against IPD disease, the WHO recommends a reference threshold of 0.2 to 0.35 µg/mL for pneumococcal conjugate vaccines (all serotypes); for polysaccharide vaccines, the current guideline is 1.3 µg/mL. A more accurate surrogate marker that is indicative of protection and that has been accepted by the FDA as correlating with clinical efficacy is the opsonic antibody titer and this has been found to be sufficiently accurate that it has replaced the need for vaccine trials. For example, opsonic titers in a vaccinated individual of 1:8 are generally regarded to be correlates of protection against the various serotypes of *S. pneumonia*. If a vaccine induces an opsonic titer of 1:8 against a particular serotype that vaccine can be regarded as clinically efficacious even in the absence of a clinical trial demonstrating reduced numbers of infections in vaccinated individuals as compared to non-vaccinated individuals.

Primary immunodeficiencies (PIDs) are a group of greater than 200 genetically inherited disorders characterized by deficiencies in individual components of the innate or adaptive immune system, with a clinical result of an increased susceptibility to infection. The most frequent immune deficiency is antibody deficiency. The main clinical features of patients with antibody deficiency (aka hypogammaglobinaemia) are recurrent infections of the respiratory tract with *Streptococcus pneumonia* being the most frequent isolated bacterium (See, e.g., Fried and Bonilla, Clin Microbiol Rev. 2009;22:396-414; Busse et al., J Allergy ClinImmunol. 2002;109:1001-1004).

For the last several decades, long-term administration of human polyvalent intravenous immunoglobulin (IVIG, also referred to herein as "conventional IVIG") has been the mainstay therapy for reducing the severity and frequency of infections in immune deficient (e.g., antibody deficient) patients (See, e.g., Salehzadeh et al., J Microbiol Immunol Infect 2010, 43(1): 11-17; Favre et al., Allergy 2005 60:385-390). Infusion of IVIG results rapidly in an immunoglobulin G (IgG) concentration peak, followed by an IgG decrease over time. The IgG level just before the next infusion (that is, the trough level) is monitored to evaluate the adequacy of a particular infusion regimen. In general, PID patients treated with IVIG receive infusions every three or four weeks. While IVIG infusion every three or four weeks has generally been successful to prevent serious lower respiratory tract infections in PID patients, there exists a significant percentage of PID patients that continue to experience upper respiratory tract infections, with associated morbidity and sickness, while being treated. This is despite the fact that most of the immune compromised patients receiving IVIG appear to have acceptable levels of total immunoglobulin as well as acceptable levels of anti-*S. pneumonia* IgG at trough (See, e.g., Favre et al., Allergy 2005 60:385-390). Furthermore, antibiotics have been used but are often ineffective.

Thus, administration of exogenous pooled human IVIG has been an important therapy in clinical medicine for patients with immune deficiency (e.g., antibody deficiencies) and appears to have prevented the occurrence of serious lower respiratory tract infections. However, and in stark contrast, conventional IVIG therapy has failed to prevent or treat the significant occurrence of the less life threatening upper respiratory tract infections (e.g., caused by *S. pneumonia*) that occur in PID patients (See, e.g., Favre et al., Allergy 2005 60:385-390; Simao-Gurge et al., Allergo Immnopathol 2017, 45:55-62). That is, while total IgG concentrations achieved by regular infusions of conventional IVIG prevent serious lower respiratory tract infections in PID patients, there remains substantial and significant morbidity from the less clinically serious upper respiratory infections in PID patients caused by *S. pneumonia* that in turn result in significant health complications, a decreased quality of life, and an indiscriminate use of broad spectrum antibiotics in the patients in an attempt to control infections.

Disclosed herein are compositions and methods for the treatment of infection caused by *Streptococcus pneumonia*. In particular, the invention provides human hyperimmune globulin and compositions thereof for preventing or treating pneumococcal infection. The invention provides methods of producing hyperimmune globulin containing high titers of opsonic anti-pneumococcal antibodies, compositions containing same, and methods of using the compositions for the prevention and treatment of pneumococcal infection. The invention further provides methods of preventing or treating pneumococcal infection (e.g., upper respiratory infections (e.g., bronchitis, otitis, sinusitis, etc.)) in immunocompromised subjects via administration of hyperimmune globulin compositions of the invention (e.g., containing a high titer of opsonic anti-pneumococcal antibodies) to immunocompromised subjects.

As described in detail herein (e.g., in the Examples), the invention provides a novel hyperimmune globulin composition containing a high titer of opsonic anti-pneumococcal antibodies that is surprisingly and significantly different than conventional immune globulin preparations as well as other IVIG preparations (e.g., other hyperimmune IVIG preparations). In particular, as described in Examples 2-4, it was surprisingly discovered that hyperimmune globulin prepared according to methods of the invention have an elevated titer of opsonic anti-pneumococcal antibodies that are functionally and broadly reactive against a multitude of *S. pneumonia* serotypes and enhance phagocytosis and killing of *S. pneumonia* in vitro (e.g., the antibodies are opsonophagocytic), independent of the total amount of binding anti-pneumococcal antibodies (e.g., as measured by ELISA) that are present in the composition. That is, experiments conducted during development of embodiments of the invention unexpectedly identified that total IgG binding antibody to the capsular polysaccharide of *S pneumonia* did not correlate with and was not predictive of the amount of functional, opsonic antibody present in immune globulin prepared from the sera of a vaccinated host (See, e.g., Examples 2-4). Thus, low levels of binding antibody may be associated with high levels of protective opsonic antibodies, and vice versa. Thus, measurement of total antibody levels only in immunoglobulin preparations does not predict or correlate with protective efficacy of that preparation. Thus, in one embodiment, the invention provides identification and characterization of plasma and/or immune globulin compositions containing a desired functional, opsonic antibody titer rather than one in which only the total amount of IgG is known (e.g., due to the identification of the lack of a correlation between total anti-pneumococcal IgG antibody titer and the titer of opsonic anti-pneumococcal antibodies present in plasma or immune globulin prepared from same from vaccinated donors).

Furthermore, a pronounced variability in the serotype specific opsonic titers was discovered in various commercial lots of conventional IVIG (See, e.g., FIG. 9A-9L, samples A-I in each representing commercial IVIG) and that a heightened titer to one serotype did not predict or correlate with a heightened titer to any of the other serotypes. This indicated that the individual heightened response in any individual conventional IVIG did not reflect a general enhanced immune response to *S pneumonia* but rather sporadic enhanced response(s) to very specific serotypes (See, e.g., Malgorzata et al., Clin Diagn Lab Immunol 2004, 11(6): 1158-1164). In marked contrast, the opsonic antibody titers observed within immune globulin prepared from immunized donors according to the invention were noted as enhanced to all serotypes without exception (See, e.g., Example 5, FIG. 8 and see FIG. 9A-9L, sample HIG—"hyperimmune globulin" of the invention). Depending on the serotype, there was between a 3-256 fold increase in the opsonic anti-pneumococcal antibody titer in the immune globulin from immunized donors compared to various different commercial lots of immune globulin (See, e.g., Example 5 and FIG. 8, commercial/conventional IVIG samples A-I versus hyperimmune donor sera). Thus, in some embodiments, compositions and methods of the invention for generating compositions (e.g., blood, plasma, and/or immune globulin compositions) containing an elevated opsonic anti-pneumococcal antibody titer provides a heterogeneous composition comprising opsonic anti-pneumococcal antibody titers specific to a multitude of pneumococcal serotypes (e.g., 9, 10, 11, 12, 13, 14, 15 or more serotypes) and/or significantly elevated (e.g., 3-256 fold more) opsonic antibody titers compared to conventional, commercial immune globulin.

Thus, due to the identification of the discordance between the total anti-pneumococcal binding IgG antibody titer and the titer of opsonic anti-pneumococcal antibodies present in plasma or immune globulin prepared from same from vaccinated donor plasma disclosed herein, it is a further object of the invention to provide a plasma and/or immune globulin composition (e.g., anti-pneumococcal hyperimmune globulin) containing a desired elevated functional, opsonic anti-pneumococcal antibody titer (e.g., of at least 1:64 to about 1:8192 (e.g., regardless of the total anti-pneumococcal binding antibody titer (e.g., by pooling plasma and/or immune globulin harvested from vaccinated donor plasma and/or immune globulin identified as possessing a high titer of opsonic anti-pneumococcal antibodies with each other, and/or, with vaccinated donor plasma and/or immune globulin that may not have a high titer of opsonic anti-pneumococcal antibodies, but that when pooled with the high titer opsonic anti-pneumococcal antibody donor plasma and/or immune globulin do not dilute the total opsonic titer to an undesirable level as compared to control sample))).

The present disclosure also describes the discovery that standard/conventional immunoglobulin pools of normal donors (e.g., used to generate commercially available, standard/conventional IVIG) do not have reliable and consistent high levels of opsonic antibody for multiple serotypes of *S. pneumonia*, whereas an immune globulin composition (e.g., anti-pneumococcal hyperimmune globulin) containing a broadly reactive, high titer of opsonic, anti-pneumococcal antibodies of the invention against a multitude of serotypes when given intravenously immediately provides specific, functional antibodies that promote phagocytosis and killing of a multitude of *S. pneumonia* serotypes by phagocytes. The invention is not limited by the serotype or number of serotypes of *S. pneumonia* for which the functional, opsonic antibodies present within a hyperimmune globulin (e.g., IVIG) composition of the invention promotes the opsonophagocytosis and/or killing. Indeed, the invention provides a composition (e.g., a hyperimmune plasma composition and/or hyperimmune globulin (e.g., IVIG) composition) of the invention contains broadly reactive, opsonic antibodies to at least 9 of 12, 10 of 12, 11 of 12 or all 12 of 12 of the following serotypes of *S. pneumonia*: 1, 3, 4, 5, 6B, 7F, 9V, 14, 18C, 19A, 19F, and 23F (See, e.g., Examples 2-5). That is, the invention provides compositions and methods of obtaining same that comprise an elevated opsonic anti-pneumococcal-specific antibody titer that is at least 2-fold, 3-fold, 4-fold, 5-fold, 7-fold, 10-fold, or more greater than the opsonic anti-pneumococcal-specific antibody titer present in a control sample (e.g., for at least 75% of the pneumococcal serotypes selected from serotypes 1, 3, 4, 5, 6B, 7F, 9V, 14, 18C, 19A, 19F, and 23F). In another embodiment, the invention provides a hyperimmune globulin (e.g., IVIG) composition that contains a high titer of broadly reactive, opsonic antibodies to at least 70%, at least 75%, at least 80%, at least 85%, at least 90%, 95%, 98%, or more of each serotype present in a vaccine or a plurality of vaccines utilized to immunize one or more plasma donors from which the immune globulin is derived.

It is a further advantage and object of the invention to provide a hyperimmune globulin (e.g., IVIG) composition containing broadly reactive, opsonic antibodies specific for *S. pneumonia* to a patient (e.g., an immune compromised patient (e.g., a PIDD patient)) in order to treat (e.g., therapeutically and/or prophylactically) pneumococcal infection in the patient (e.g., by inhibiting *S. pneumonia* growth and/or clearing *S. pneumonia* from the blood of the patient). The invention also provides a hyperimmune globulin (e.g., IVIG) composition containing broadly reactive, opsonic antibodies specific for *S. pneumonia* to a patient (e.g., an immune compromised patient (e.g., a PIDD patient)) in order to treat pneumococcal infection in the patient (e.g., by improving or enhancing *S. pneumonia* clearance from the blood of the patient). The invention also provides a hyperimmune globulin (e.g., IVIG) composition containing broadly reactive, opsonic antibodies specific for *S. pneumonia* to a patient (e.g., an immune compromised patient (e.g., a PIDD patient)) in order to prevent upper respiratory tract infections in the patient that are not preventable with conventional IVIG treatment. The invention is not limited by the type of upper respiratory tract infection prevented and/or treated and may include, but is not limited to, rhinosinusitis (sinusitis), otitis media, pharyngitis, epiglottitis, laryngotracheitis, and laryngotracheobronchitis. Similarly, compositions and methods of using (e.g., administering) the same find use in preventing and/or treating signs or symptoms of upper respiratory tract infection including, but not limited to, cough, sneezing, nasal discharge, nasal congestion, runny nose, fever, scratchy or sore throat, and nasal breathing.

The invention is not limited by the type of streptococcal infection treated (e.g., prophylactically and/or therapeutically). Indeed, any streptococcal infection caused by the streptococcus group of bacteria may be treated. There are more than 90 different strains of *Streptococcus pneumonia* (*S. pneumonia*) bacteria (known as serotypes), some of which cause more serious infection than others. The symptoms of a pneumococcal infection can vary, depending on the type of infection. Common symptoms include: a high temperature (fever) of 38 C (100.4 F), aches and pains, and/or headache Pneumococcal infections usually fall into one of two categories: non-invasive pneumococcal infections-these occur outside the major organs or the blood and tend to be less serious; and invasive pneumococcal infections-these occur inside a major organ or the blood and tend to be more serious. Compositions of the invention and methods of using same find use in treating (e.g., therapeutically and/or prophylactically) both non-invasive as well as invasive pneumococcal infections.

In one embodiment, the invention provides compositions and methods for obtaining a composition comprising pooled plasma samples (e.g., plasma from a plurality of donors (e.g., donors that have been vaccinated with one or more pneumococcal vaccines)) that contain high titers of opsonic anti-pneumococcal antibodies. Thus, it is an object of the invention to provide methods of generating compositions (e.g., blood, plasma, and/or immune globulin compositions) containing a high titer of opsonic, anti-pneumococcal antibodies. In one embodiment, one or a plurality of healthy adult human subjects (e.g., human subjects with no known medical conditions) are administered a pneumococcal immunogen, recombinant pneumococcal protein, or a combination thereof. In some embodiments, a *S. pneumonia* immunogen is a *S. pneumonia* cell membrane sugar (e.g., a polysaccharide). In some embodiments, a *S. pneumonia* immunogen is a conjugate vaccine (e.g., conjugated to a carrier and/or adjuvant (e.g., a protein or other carrier molecule). In some embodiments, a *S. pneumonia* immunogen is an unconjugated vaccine. In some embodiments, the conjugate vaccine or unconjugated vaccine contains 1, 2, 3, 4, 5, 6, 7, 8, 9, 10, 11, 12, 13, 14, 15, 16 ,17, 18, 19, 20, 21, 22, 23 or more different immunogens (e.g., from an equal number of different serotypes of *S. pneumonia*). In some embodiments, the one or more different serotypes of *S. pneumonia* include, but are not limited to, serotypes 1, 2, 3, 4, 5, 6A, 6B, 7A, 7B, 7C, 7D, 7E, 7F, 8, 9A-9V, 12, 14, 18C, 19A-19F, 23A-23F, and 25. In some embodiments, the one or more different serotypes of *S. pneumonia* are selected from any one of the more the 90 different *S. pneumonia* serotypes identified. In some embodiments, the one or more different serotypes of *S. pneumonia* is newly identified.

One or a plurality of healthy human subjects (e.g., human subjects with no known medical conditions) can be administered a pneumococcal immunogen, recombinant pneumococcal protein, or a combination thereof present in a commercial pneumococcal vaccine. The invention is not limited by the type of commercial pneumococcal vaccine. Indeed, any pneumococcal vaccine known in the art can be utilized including, but not limited to, pneumococcal conjugate vaccine (PCV13 or PREVNAR13, Wyeth Pharmaceuticals, Collegeville, PA), SYNFLORIX, and/or pneumococcal polysaccharide vaccine (PPSV23 or PNEUMOVAX23, Merck Sharp & Dohme Corp., North Wales, PA). In one embodiment, one or a plurality of healthy human subjects receives a first or prime vaccination with a first anti-pneumococcal vaccine, and a subsequent boost vaccination with the first anti-pneumococcal vaccine or with a second, different anti-pneumococcal vaccine. For example, in one embodiment, one or a plurality of healthy human subjects receive a first or prime vaccination/immunization with a first anti-pneumococcal vaccine (e.g., PREVNAR), and then receive a boost vaccination/immunization (e.g., at 2 weeks, 4 weeks, 6, weeks, 8 weeks, 10 weeks, 12 weeks or longer post the prime vaccination/immunization) with a second anti-pneumococcal vaccine (e.g., PNEUMOVAX23). At a time point subsequent to the sequential vaccination (e.g., at 2 weeks, 4 weeks, 6, weeks, 8 weeks, 10 weeks, 12 weeks or longer post the sequential vaccination), sera/plasma is harvested from the vaccinated, healthy human plasma donors. Plasma from the vaccinated donors may be pooled (with each other and/or with plasma from non-vaccinated donors) followed by harvest of immune globulin from same. Methods of harvesting plasma as well as immune globulin are well known by those of ordinary skill in the art.

In one embodiment, the invention provides a method for preparing a hyperimmune globulin having a high titer of opsonophagocytic antibody to *Streptococcus pneumonia* (e.g., a titer that is at least 2-fold, 3-fold, 4-fold, 5-fold, 7-fold, 10-fold, or more greater for at least about 55% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) compared to the opsonophagocytic anti-pneumococcal-specific antibody titers for the same serotypes present in a control sample; or, a titer specific for 70% or more of the *S. pneumonia* serotypes selected from serotypes 4, 6B, 9V, 14, 18C, 19F, and 23, that is 2 fold or greater (e.g., 3-25 fold or greater) than the titer of opsonophagocytic antibodies specific for the same *S. pneumonia* serotypes present in a control sample; or, a titer between 1:64 and 1:8192 (e.g., for at least 50% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) as determined by an opsonophagocytic killing assay described herein) comprising the steps of immunizing healthy adult human plasma donors between the ages of 18-60 with a prime multivalent *S. pneumonia* vaccine followed by immunization with a boost multivalent *S. pneumonia* vaccine that is different than the prime vaccine; harvesting plasma from the plasma donors subsequent to the boost immunization; pooling plasma from the vaccinated donors in order to obtain a pooled plasma containing a high titer of opsonophagocytic antibody titer to *S. pneumonia*; and preparing an immune globulin from the pooled plasma. In a further embodiment, the method comprises rendering the immune globulin obtained intravenously injectable. The immune globulin can be provided in solution and/or the pH and ionic strength of the solution can be adjusted so as to render it intravenously injectable. The invention is not limited by the number of individuals vaccinated according to the methods described herein. For example, 100, 200, 300, 400, 500, 600, 700, 800, 900, 1000, 1100, 1200, 1300, 1400 or more healthy adult human plasma donors can be vaccinated and plasma harvested from the donors. In one embodiment, the pooled plasma is made from pooling plasma from 1000 or more different healthy vaccinated adult human plasma donors. In one embodiment, the pooled plasma contains an opsonophagocytic antibody titer that is at least 2-fold, 3-fold, 4-fold, 5-fold, 7-fold, 10-fold, or more greater for at least about 55% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) compared to the opsonophagocytic anti-pneumococcal-specific antibody titers for the same serotypes present in a control sample (e.g., plasma, or immune globulin prepared from plasma, pooled from 1000 or more random non-vaccinated human plasma donors). In another embodiment, the pooled plasma contains an opsonophagocytic antibody titer specific for 70% or more of the *S. pneumonia* serotypes selected from serotypes 4, 6B, 9V, 14, 18C, 19F, and 23, that is 2 fold or greater (e.g., 3-25 fold or greater) than the titer of opsonophagocytic antibodies specific for the same *S. pneumonia* serotypes present in a control sample (e.g., plasma, or immune globulin prepared from plasma, pooled from 1000 or more random non-vaccinated human plasma donors). In yet another embodiment, the pooled plasma contains an opsonophagocytic antibody titer between 1:64 and 1:8192 (e.g., for at least 50% or more (e.g., 60%, 65%, 70%, 75%, 80%, 85% or more) of *S. pneumonia* serotypes 1, 3, 4, 5, 6B, 7F, 9V, 14, 18C, 19A, 19F, and 23F) as determined by an opsonophagocytic killing assay described herein. The invention also provides hyperimmune globulin prepared according the above described method. Hyperimmune globulin so prepared can be used in various methods. For example, the hyperimmune globulin can be used in a method of treating *S. pneumonia* infection in a subject (e.g., comprising administering to the subject a therapeutically effective amount of the hyperimmune globulin). The hyperimmune globulin can also be used in a method of providing immunotherapy to a subject (e.g., comprising administering to the subject a therapeutically effective amount of the hyperimmune globulin).

The invention also provides, in one embodiment, a method of preparing immune globulin having enhanced opsonophagocytic bactericidal activity against at least seven serotypes of *Streptococcus pneumonia* (e.g., serotypes 4, 6B, 9V, 14, 18C, 19F, and 23F) for the prevention or treatment of *S. pneumonia* infection comprising the steps of immunizing healthy adult human plasma donors with a primary immunization with a multivalent *S. pneumonia* conjugate vaccine followed by boost immunization with a multivalent polysaccharide *S. pneumonia* vaccine that is different than the prime vaccine; harvesting and pooling the plasma from the immunized plasma donors; and preparing immune globulin from the pooled plasma, wherein the immune globulin contains an opsonophagocytic antibody titer specific for each of the at least seven serotypes of *S. pneumonia* that is two-fold or higher than the opsonophagocytic antibody titer specific for each of the at least seven serotypes of *S. pneumonia* present in a control sample (e.g., immune globulin prepared from plasma pooled from 1000 or more random non-vaccinated human plasma donors). The invention also provides an immune globulin prepared according the above described method. Immune globulin so prepared can be used in various methods. For example, the immune globulin can be used in a method of treating *S. pneumonia* infection in a subject comprising administering to the subject a therapeutically effective amount of the immune globulin. The immune globulin can also be used in a method of providing immunotherapy to a subject comprising administering to the subject a therapeutically effective amount of the immune globulin.

Experiments conducted during development of embodiments of the invention discovered that significant numbers of patients being treated with IVIG had trough anti-*S. pneumonia* antibody concentrations that fell below what is regarded as protective. For example, as shown in FIG. 10, it was determined that a significant percentage of patients with primary immune deficiency disease being treated with conventional IVIG had serotype-specific levels of total anti-*S. pneumonia* binding antibodies that fell below a protective level (below 1.2 µg/ml) at trough.

All immune globulin fractionated and/or isolated from sera and used for intravenous infusion contains little if any measurable IgA which may account for the inability of the immune globulin to protect at mucosal surfaces (e.g., thereby leading to increased upper respiratory tract infection in immune deficient patients receiving conventional IVIG). Thus, while a mechanism is not needed to practice the present invention, and while the present invention is not limited to any particular mechanism of action, in some embodiments, a hyperimmune globulin composition of the invention that contains a high concentration of broadly reactive, opsonic anti-*S. pneumonia* antibodies (e.g., provided in a hyperimmune globulin composition of the invention) permits gradient diffusion of higher concentrations of functional, broadly reactive, opsonic anti-pneumococcal IgG across mucosal membranes thereby affording mucosal protection and reduced incidence of upper respiratory infection (e.g., compared to conventional IVIG that does not have a high concentration of broadly reactive, opsonic anti-*S. pneumonia* antibodies and therefore much less or no gradient diffusion resulting in high incidence of upper respiratory tract infection in immune compromised patients treated with conventional IVIG)).

Thus, the invention provides hyperimmune globulin prepared according the any of the methods described herein that contains an elevated titer of opsonic antibodies specific for 1, 2, 3, 4, 5, 6, 7, 8, 9, 10, 11, 12, 13, 14, 15, 16 ,17, 18, 19, 20, 21, 22, 23 or more different serotypes of *S. pneumonia* including, but are not limited to, serotypes 1, 2, 3, 4, 5, 6A, 6B, 7A, 7B, 7C, 7D, 7E, 7F, 8, 9A-9V, 12, 14, 18C, 19A-19F, 23A-23F, and 25. While an understanding of a mechanism is not needed to practice the present invention and while the present invention is not limited to any particular mechanism of action, pooling of vaccinated donor sera provides desired levels (e.g., therapeutically and/or prophylactically protective levels) of broadly reactive, opsonic IgGs against all serotypes present in one or more vaccines utilized to vaccinate healthy adult human plasma donors, (e.g., despite any serotype to serotype variation and/or degree of dilution while pooling). Accordingly, in some embodiments, any individual difference in serotype specific opsonic IgG concentration can be normalized without compromising the protective levels of these antibodies by pooling of the sera. Purification of immune globulin from serum did not result in any deficit in any pneumococcal serotype specific opsonic IgG nor its functional activities.

Preparation of Purified Immunoglobulin. In one embodiment, purified immunoglobulin is prepared that has a high titer of pneumococcal specific, opsonic antibodies. The term "high titer" in this context means the presence of an antibody in an amount which is 2-fold or greater (e.g., up to 10-20 or more times higher than that found in a normal population of 1000 random samples).

The blood product can be prepared by (i) selection and purification of the immunoglobulin from a donor which has been vaccinated (e.g., via a process of the invention) and has high titers of pneumococcal specific, opsonic antibodies, or (ii) the combination of donor immunoglobulin from a multitude of individuals (e.g., 100, 200, 200-500, 500-1000, or 1000 or more subjects) which have been vaccinated according to a method of the invention.

Plasmapheresis may be used to harvest serum/plasma from a vaccinated donor. The term plasmapheresis describes a technique in which blood is removed from an animal, separated into its cellular and plasma components, the cells are then returned to the animal, and the plasma retained. Large volume plasmapheresis requires the removed plasma to be replaced by a suitable fluid, and when this is done, the technique is often known as plasma exchange. Any components found in plasma can be removed by plasma exchange. Plasma extracted this way for commercial sale is available for use in a preferred embodiment of this invention.

In some embodiments, it is preferred to identify and maintain a consistent donor group by repeated drawing of small quantities of blood, for example, drawing of blood once a month from humans. The frequency of the drawing may influence the quantity which may be safely drawn. In general, it is desired to draw the maximum amount of blood over the course of time without causing detriment to the health of the donor. This may dictate drawing small amounts with great frequency, or the maximum amount possible at a reduced frequency. The blood volume of the donor may be estimated by standard formulas available from the Center for Disease Control. Methods of blood and plasma collection is generally standard and well to known to those of skill in the art. Any method can be used that achieves the desired results.

Following plasma isolation, immune globulin (antibodies) may be purified away from other cell products. This can be accomplished by a variety of protein isolation procedures, known to those skilled in the art of immunoglobulin purification, such as Cohn fractionation, ion exchange, affinity purification, etc. Means for preparing and characterizing antibodies are well known in the art. For example, serum samples can be passed over protein A or protein G sepharose columns to bind IgG (depending on the isotype). The bound antibodies can then eluted with, e.g. a pH 5.0 citrate buffer. The elute fractions containing the Abs, are dialyzed against an isotonic buffer. Alternatively, the eluate is also passed over an anti-immunoglobulin-sepharose column. The Ab can then eluted with 3.5 M magnesium chloride. Abs purified in this way can then tested for binding activity by, for example, an isotype-specific ELISA and immunofluorescence staining assay of the target cells, or for opsonic (opsonophagocytic) activity (e.g., using one or more of the opsonic killing assays described herein).

In one embodiment, when plasma samples are harvested and mixed (e.g., from a plurality of subjects (e.g., 100, 200, 200-500, 500-1000, 1000 or more subjects) immunized according to methods described herein), the mixed plasma or immune globulin obtained (e.g., isolated and/or fractionated) from same contains seroprotective antibody titers to measles, diphtheria and/or polio (e.g., contain antibody titers to measles, diphtheria and/or polio that provide a subject administered the blended plasma composition or immunoglobulin obtained from same serum levels of antibodies specific for measles, diphtheria and polio to prevent, or protect from, infection with same). In another embodiment, when plasma samples are mixed from a plurality of vaccinated subjects, the mixed plasma or immune globulin obtained (e.g., fractionated) from same contains seroprotective antibody titers to measles, diphtheria, polio, and/or tetanus (e.g., contain antibody titers to measles, diphtheria, polio, and/or tetanus that provide a subject administered the mixed plasma composition or immune globulin obtained from same serum levels of antibodies specific for measles, diphtheria, polio, and/or tetanus to prevent, or protect from, infection with same (e.g., meets the antibody titer levels recommended by U.S. Food and Drug Administration (e.g., for the treatment of immune deficiency disease and/or treatment of or prevention of infection in an immune deficient subject))). In one embodiment, the mixed/pooled plasma comprises plasma samples obtained from 1000-3000 or more (e.g., more than 1000, 1250, 1500, 1750, 2000, 2500, 3000, 3500, 4000 or more human subjects). In one embodiment, the pooled plasma is utilized to prepare immunoglobulin (e.g., for intravenous administration to a subject). In one embodiment, the pooled plasma and/or immunoglobulin provides a therapeutic benefit to a subject administered the pooled plasma and/or immunoglobulin that is not achievable via administration of a mixture of plasma samples (or immune globulin prepared from same) obtained from 1000 or more random human subjects. The invention is not limited by the type of therapeutic benefit provided. Indeed, a variety of therapeutic benefits may be attained including those described herein (e.g., treatment of pneumococcal infection (e.g., upper respiratory tract infections)). In one embodiment, the pooled plasma and/or immune globulin possesses enhanced anti-pneumococcal opsonophagocytic properties compared to a mixture of plasma samples obtained from 1000 or more random human subjects or immune globulin prepared from same. For example, in one embodiment, the pooled plasma possesses enhanced anti-pneumococcal opsonophagocytic properties against ten or more different pneumococcal serotypes (e.g., 10, 10-20, 20-30, or more serotypes). In a further embodiment, the enhanced anti-pneumococcal opsonophagocytic properties reduce and/or prevent infection in a subject administered the composition for a duration of time that is longer than, and not achievable in, a subject administered a mixture of plasma samples obtained from 1000 or more random (e.g., non-vaccinated) human subjects. In one embodiment, the pooled plasma and/or immune globulin prepared from same reduces the incidence of infection in a subject administered the composition. In another embodiment, a pooled plasma and/or immune globulin prepared from same reduces the number of days a subject administered the pooled plasma and/or immunoglobulin is required to be administered antibiotics (e.g., to treat infection). In yet another embodiment, a pooled plasma and/or immune globulin prepared from same increases the trough level of circulating anti-pneumococcal opsonophagocytic antibodies in a subject (e.g., increases the level of anti-opsonophagocytic antibody titer specific for ten or more pneumococcal serotypes (e.g., thereby providing protective levels of anti-pneumococcal opsonophagocytic antibodies between scheduled dates of administration of the pooled plasma and/or immune globulin prepared from same that are not maintained in a subject administered a mixture of plasma samples obtained from 1000 or more random human subjects or immune globulin prepared from same)). In one embodiment, the composition comprising pooled plasma samples further comprises a pharmaceutically acceptable carrier (e.g., any natural or non-naturally occurring carrier(s) known in the art). In one embodiment, a subject administered immunoglobulin prepared from pooled plasma according to the invention displays a mean fold increase in anti-pneumococcal opsonophagocytic antibody titer that is at least 2 fold, 3 fold, 4 fold, at least 5 fold, at least 6 fold, at least 7 fold, at least 8 fold, at least 9 fold or more at a time point of at least 1 to 14 days post administration (e.g., 14 day, 15 days, 16 days, 17 days, 18 days, 19 days or more) of the immune globulin. The invention is not limited by the amount of immune globulin administered to a subject. In one embodiment, a subject is administered between 100-5000 mg/kg of the immunoglobulin one time, or daily for two or more days (e.g., 2, 3, 4, or more consecutive days). In another embodiment, such doses are administered intermittently, e.g. every week, every two weeks, every three weeks, every four weeks, etc. In one embodiment, a subject is administered between 750-1500 mg/kg of immune globulin on day one and between 750-1500 mg/kg immune globulin on day 2. In one embodiment, a subject is administered 1500 mg/kg of immune globulin on day one and 750 mg/kg immune globulin on day 2. In another embodiment, a subject is administered 750 mg/kg of immune globulin on day one and 750 mg/kg immune globulin on day 2. In one embodiments, a subject is administered immune globulin on day one, optionally administered immune globulin on day 2, and then re-administered immune globulin every 21 days. In one embodiments, a subject is administered immune globulin on day one, optionally administered immune globulin on day 2, and then re-administered immune globulin every 28 days. In one embodiment, the pooled plasma and/or immune globulin prepared from same reduces the incidence of pneumococcal infection in a subject administered the composition. In yet another embodiment, a pooled plasma and/or immune globulin prepared from same increases the trough level of circulating anti-pneumococcal opsonophagocytic antibodies and increases the trough level of circulating anti-measles, anti-diphtheria, anti-polio, and/or anti-tetanus specific antibodies in a subject (e.g., increases the level of anti-pneumococcal opsonophagocytic antibody titers specific for pneumococcal serotypes and measles, diphtheria, polio, and/or tetanus (e.g., thereby providing protective levels of anti-pneumococcal opsonophagocytic antibodies and anti-measles, anti-diphtheria, anti-polio, and/or anti-tetanus specific antibodies between scheduled dates of administration of the pooled plasma and/or immune globulin prepared from same that are not maintained in a subject administered a mixture of plasma samples obtained from 1000 or more random human subjects (e.g., non-vaccinated subjects) or immune globulin prepared from same)).

In some embodiments, plasma and/or antibody samples comprise donated and/or purchased body fluid samples, for example individual blood or blood component samples (e.g., plasma). These samples may be purified and/or screened for the presence of pathogens or other impurities (e.g., before or after pooling). Multiple donor antibody samples (e.g., donor plasma samples or other antibody-containing samples) can pooled together to create a pooled plasma sample. In some embodiments, the pooled antibody samples are purified, screened, and/or concentrated. In one embodiment, pooling of samples (e.g., 1000 or more samples) occurs in a manner that uses the fewest possible number of samples (e.g., generated by the compositions and methods described herein) but that still maintains a desired, standardized and elevated level of anti-pneumococcal opsonophagocytic antibodies.

As described herein, certain embodiments of the invention utilize plasma from subjects that have been administered immunogenic substances (e.g., vaccines) in order to generate elevated levels of anti-pneumococcal opsonophagocytic antibodies within the subject. The invention is not limited by the type of vaccine and/or antigen (e.g., S. pneumonia antigen) used for administration to a subject (e.g., donor) to induce the expression of specific antibodies. In some embodiments, the antigen is a S. pneumonia antigen or fragment or component thereof. In some embodiments, the antigen is a polysaccharide (e.g., unconjugated or conjugated to a carrier or protein) or a plurality of the same. In some embodiments, the antigen (e.g., S. pneumonia antigen) is a vaccine comprising components capable of inducing specific antibodies (e.g., antibodies that are specific to multiple different serotypes of S. pneumonia). In some embodiments, a vaccine is a commercially available vaccine. The invention is not limited by the vaccine. Indeed, a variety of vaccines (e.g., S. pneumonia vaccines) may be utilized including, but not limited to, PREVNAR, SYNFLORIX, PNEUMOVAX as well as others known in the art.

Similarly, the invention is not limited by the type or route of administration/immunization. Indeed, any route/type of immunization may be utilized including, but not limited to, the methods described in U.S. patent Publication Nos. US2008026002, US2007009542; US2002094338; US2005070876; US2002010428; US2009047353; US2008066739; and US2002038111), each of which is hereby incorporated by reference in its entirety. In like manner, the invention is not limited by the vaccine formulation (e.g., of a S. pneumonia vaccine). Indeed, any formulation may be utilized including, but not limited to, those described in US2002107265, hereby incorporated by reference in its entirety. In some embodiments, the vaccine is a multivalent vaccine in which additional antigens are added (See, e.g. US2007161088; US2006121059, each of which is hereby incorporated by reference in its entirety.). In some embodiments, antigens are purified prior to use in a vaccine (e.g., a conjugate vaccine) (See, e.g., US2008286838 hereby incorporated by reference in its entirety). Methods of culture of microorganisms useful in a process of manufacturing a pneumococcal conjugate vaccines are described in US2010290996, hereby incorporated by reference in its entirety. Alternatively, in some embodiments, antigens (e.g., S. pneumonia antigens) are utilized that are not conjugated to a carrier protein (See, e.g., US2009136547, hereby incorporated by reference in its entirety). In some embodiments, immunomodulators are utilized (See, e.g., US2004156857; U.S. Pat. No. 5,985,264; and WO11041691, each of which is hereby incorporated by reference in its entirety). In some embodiments, therapeutic antibodies are produced in a donor administered an antigen (e.g., an *S. pneumonia* antigen) and/or vaccine according to the methods described in WO05070458; U.S. Pat. No. 20,091,91217; and WO10094720, each of which is hereby incorporated by reference in its entirety. In some embodiments, antigens (e.g., vaccines (e.g., conjugate or unconjugated vaccines)) are used to generate antibodies (e.g., present in serum and/or plasma) that are useful against infectious disease organisms (e.g., as described in, for example, US2003099672; WO0062802, each of which is hereby incorporated by reference in its entirety).

In some embodiments, a polysaccharide vaccine is used (e.g., containing multiple *S. pneumonia* serotypes (e.g., containing purified polysaccharides from 1, 2, 3, 4, or more or all 23 of the following *S. pneumonia* serotypes: 1, 2, 3, 4, 5, 6b, 7F, 8,9N, 9V, 10A, 11A, 12F, 14, 15B, 17F, 18C, 19F, 19A, 20, 22F, 23F and 33F). Although an understanding of a mechanism is not needed to practice the present invention, and while the present invention is not limited to any particular mechanism of action, in some embodiments, an antigen (e.g., a *S. pneumonia* antigen) or vaccine that stimulates B-cells (e.g., plasma cells) to generate and secrete specific (e.g., *S. pneumonia*-specific) immunoglobulin without the assistance of T cells finds use in the invention.

In some embodiments, a conjugated vaccine is utilized that contains capsular polysaccharides (e.g., from a plurality of *S. pneumonia* serotypes) that is covalently bound to a carrier and/or adjuvant (e.g., the diphtheria toxoid CRM197). Although an understanding of a mechanism is not needed to practice the present invention, and while the present invention is not limited to any particular mechanism of action, in some embodiments, any antigen (e.g., *S. pneumonia* antigen) or vaccine that stimulates B-cells (e.g., plasma cells) to generate and secrete specific (e.g., *S. pneumonia*-specific) immunoglobulin (e.g., *S. pneumonia*-specific IgM and/or IgG) via interaction with specific type 2 helper T cells) and/or production of memory B cells (e.g., *S. pneumonia*-specific memory B cells) finds use in the invention.

Thus, in some embodiments, the invention provides methods of stimulating high levels of opsonophagocytic anti-pneumococcal antibodies in a donor, which includes administering to an animal, for example a human, a pharmaceutically-acceptable composition comprising an immunologically effective amount of an antigen composition (e.g., an *S. pneumonia* antigen composition). The composition can include partially or significantly purified antigens (e.g., *S. pneumonia* antigens (e.g., polysaccharide, protein and/or peptide epitopes, obtained from natural or recombinant sources, which may be obtained naturally or either chemically synthesized, or alternatively produced in vitro from recombinant host cells expressing DNA segments encoding such epitopes)).

Methods to determine the efficacy of immunization (e.g., determining the level of *S. pneumonia*-specific antibody titers) are known in the art, and any known method may be utilized to assess the efficacy of immunization (e.g., the efficacy of inducing opsonophagocytic anti-pneumococcal antibodies (e.g., an opsonophagocytic killing assay described herein or known in the art)). In some embodiments, detection methods for the evaluation of the efficacy of a vaccine (e.g., a pneumococcal conjugate vaccine) is used as described in, for example, US2005260694; U.S. Pat. Nos. 4,308,026; 4,185,084; or US2005208608, each of which is hereby incorporated by reference in its entirety.

In some embodiments, kits and methods are provided that identify samples and/or pools with specific antibody titers (e.g., opsonophagocytic anti-pneumococcal antibody titers that are elevated). In one embodiment, a suitable amount of a detection reagent (e.g., antibody specific for antibodies, an antigen, or other reagent known in the art) is immobilized on a solid support and labeled with a detectable agent. Antibodies can be immobilized to a variety of solid substrates by known methods. Suitable solid support substrates include materials having a membrane or coating supported by or attached to sticks, beads, cups, flat packs, or other solid support. Other solid substrates include cell culture plates, ELISA plates, tubes, and polymeric membranes. The antibodies can be labeled with a detectable agent such as a fluorochrome, a radioactive label, biotin, or another enzyme, such as horseradish peroxidase, alkaline phosphatase and 2-galactosidase. If the detection reagent is an enzyme, a means for detecting the detection reagent can be supplied with the kit. A suitable means for detecting a detectable agent employs an enzyme as a detectable agent and an enzyme substrate that changes color upon contact with the enzyme. The kit can also contain a means to evaluate the product of the assay, for example, a color chart, or numerical reference chart. Some suitable methods for characterizing samples and pools are provided in the references incorporated by reference herein. The present invention is not limited by the method used to characterize samples and pools as having elevated titer. Assays to determine the level of anti-pneumococcal opsonophagocytic antibodies in plasma, immune globulin, and/or pools thereof may also be used (e.g., as described in the Examples).

In certain embodiments, compositions are provided (e.g., antibody samples, pooled plasma samples, immune globulins, etc.) in which antibodies have been purified and/or isolated from one or more contaminants. Human immunoglobulins were first isolated on a large scale during the 1940's by F. J. Cohn. In some embodiments, the techniques provided by Cohn (Cohn et al., J. Am. Chem. Soc. 1946; 68:459-475; herein incorporated by reference in its entirety) or modified Cohn-techniques are utilized in preparation of immune globulins herein. In some embodiments, various purification and isolation methods are utilized to produce substantially unmodified, unaltered, non-denatured and/or native immune globulin molecules of high purity. Exemplary techniques are provided, for example, in U.S. Pat. No. 4,482,483, herein incorporated by reference in its entirety. In some embodiments, compositions (e.g., antibody pools) comprise >50% immunoglobulin (e.g., >60%, >70%, >80%, >90%, >95%, >99%). Various methods may be utilized for producing such compositions, including, for example, standard protein purification and isolation techniques as well as fractionation of biological fluids (e.g., plasma). Descriptions of fractionation of antibodies for use in immunotherapeutics are found, for example in U.S. Pat. No. 4,346,073 and other references provided herein, each of which is incorporated by reference in their entireties. In certain embodiments, immunoglobulins are purified by a fractional precipitation method, ion-exchange chromatography, size exclusion chromatography, ultrafiltration, affinity chromatography, or any suitable combinations thereof (See, e.g., U.S. Pat. Nos. 7,597,891; 4,256,631; 4,305,870; Lullau et al., J. Biol. Chem. 1996; 271:16300-16309; Corthesy, Biochem. Soc.

Trans. 1997; 25:471-475; and Crottet et al., Biochem. J. 1999; 341:299-306; herein incorporated by reference in their entireties).

A composition of the invention (e.g., pooled plasma and/or immune globulin prepared from same) can be administered by any suitable means, including parenteral, subcutaneous, intraperitoneal, intrapulmonary, and, if desired for local treatment, intralesional administration. Parenteral infusions include intramuscular, intravenous, intraarterial, intraperitoneal, or subcutaneous administration. In addition, compositions of the invention may be administered by pulse infusion, particularly with declining doses. Dosing can be by any suitable route, e.g. by injections, such as intravenous or subcutaneous injections, depending in part on whether the administration is acute or chronic.

A composition of the invention may be formulated, dosed, and/or administered in a fashion consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners. Compositions of the invention need not be, but optionally are formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a composition of the invention (when used alone or in combination with one or more other additional therapeutic agents) may depend upon a number of factors including the type of disease to be treated, the type of antibody, the patient's size, body surface area, age, the particular compound to be administered, sex, time and route of administration, general health, interaction with other drugs being concurrently administered, the severity and course of the disease, whether the antibody is administered for preventive or therapeutic purposes, previous therapy, and the patient's clinical history.

An exact dosage may be determined by the individual physician in view of the patient to be treated. Dosage and administration are adjusted to provide sufficient levels of the active moiety (e.g., plasma pool) or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks, four weeks, six weeks, eight weeks or more, depending on half-life and clearance rate of the particular formulation.

A composition of the invention may be administered to the patient at one time or over a series of treatments. Depending on the type and severity of the disease, about 1 µg/kg to 5000 mg/kg (e.g. 0.5 mg/kg-1500 mg/kg) of a composition of the invention can be an initial candidate dosage for administration to the patient, whether, for example, by one or more separate administrations, or by continuous infusion. As described herein, additional drugs or agents (e.g., antimicrobials (e.g., antibiotics, antivirals, antifungals, etc.), other immunoglobulin compositions (e.g., conventional IVIG), anti-inflammatory and/or healing compounds, etc.) may be administered concurrently with a pooled plasma composition of the invention. An exemplary daily dosage of such agent may range from about 1 µg/kg to 100 mg/kg or more. For repeated administrations over several days or longer, depending on the condition, the treatment can generally be sustained until a desired suppression of disease symptoms occurs. One exemplary dosage of a composition of the invention would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to a patient. Such doses may be administered intermittently, e.g. every week or every two or three weeks. A medical practitioner is readily able to monitor the therapeutic administration of a composition of the invention and can in turn determine if higher or lower doses of the composition is to be administered.

Compositions of the invention may be administered (e.g., intravenously, orally, intramuscularly, subcutaneously, etc.) to a patient in a pharmaceutically acceptable carrier such as physiological saline. Such methods are well known to those of ordinary skill in the art.

Accordingly, in some embodiments of the present invention, a composition of the invention can be administered to a patient alone, or in combination with other drugs or in pharmaceutical compositions where it is mixed with excipient(s) or other pharmaceutically acceptable carriers. In one embodiment of the present invention, the pharmaceutically acceptable carrier is pharmaceutically inert. Depending on the condition being treated, pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may for example, include oral or transmucosal administration; as well as parenteral delivery, including intramuscular, subcutaneous, intramedullary, intrathecal, intraventricular, intravenous, intraperitoneal, or intranasal administration.

For injection, a composition of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the compositions of the present invention (e.g., pharmaceutical compositions) can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of a composition of the invention may be that amount that results in the inhibition of growth and/or killing of bacteria in a subject. Determination of effective amounts is well within the capability of those skilled in the art, especially in light of the disclosure provided herein.

In addition to the active ingredients pharmaceutical compositions may contain suitable pharmaceutically acceptable carriers comprising excipients and auxiliaries that facilitate processing of the compositions of the invention into preparations which can be used pharmaceutically.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the compositions in water-soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compositions to allow for the preparation of highly concentrated solutions.

Compositions of the invention formulated in a pharmaceutical acceptable carrier may be prepared, placed in an appropriate container, and labeled for treatment of an indicated condition. Conditions indicated on the label may include treatment or prevention of a viral or bacterial infection.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-% mannitol at a pH range of 4.5 to 5.5 that is combined with buffer prior to use.

Compositions of the present invention (e.g., anti-pneumococcal hyperimmune globulin) can be combined with additional agents (e.g., antibodies, antibody fragments, antibody-like molecules, monoclonal antibodies, antimicrobials, other immune globulin compositions (e.g., conventional IVIG), or other proteins or small molecules) to enhance the immunotherapeutic and/or anti-inflammatory affect. Such additional agents may be produced recombinantly, synthetically, in vitro, etc. The present invention is not limited by the types of additional agents that an anti-pneumococcal hyperimmune globulin is co-administered and/or combined with. In some embodiments, recombinant or synthetic antibodies (e.g., humanized monoclonals) or antibody fragments (e.g., directed to a specific pathogen or antigen) are co-administered and/or added. In addition, antibodies (e.g., monoclonal, polyclonal, etc.) for specified bacteria and viruses can be co-administered and/or added to the compositions. In some embodiments, various therapeutics (e.g., anti-inflammatory agents, chemotherapeutics), stabilizers, buffers, etc. are co-administered and/or added to the anti-pneumococcal hyperimmune globulin, for example, to further enhance the efficacy, stability, administerability, duration of action, range of uses, etc. In one embodiment, an anti-pneumococcal hyperimmune globulin is co-administered with a conventional IVIG (e.g., to a patient with primary immunodeficiency disease (e.g., to treat (e.g., prophylactically and/or therapeutically) infection (e.g., caused by *S. pneumonia, Corynebacterium diphtheria*, measles virus, and/or polio virus)).

Compositions may optionally contain carriers such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the immunoglobulins can be brought about by the use of agents delaying absorption, for example, aluminum monostearate and gelatin.

In some embodiments, anti-pneumococcal hyperimmune globulin of the invention is administered to a subject to provide therapeutic, preventative, prophylactic, and/or other benefits.

Diseases and conditions for which administration of the anti-pneumococcal hyperimmune globulin of the invention is to be used therapeutically or prophylactically include, but are not limited to: common variable immunodeficiency, IgA deficiency, human immunodeficiency virus (HIV) infection, bacterial and viral infections such as respiratory tract infection with influenza, respiratory tract infection with respiratory syncytial virus, respiratory tract infection with rhinovirus, respiratory tract infection with adenovirus: protozoan infections such as giadiasis, yeast infections; chronic lymphocytic leukemia; multiple myeloma; macroglobulinemia; chronic bronchitis; broncliectasis; asthma; immune suppression associated with bone marrow transplantation; immune suppression associated with cyclophosphamide administration; immune suppression associated with azathiaprine administration; immune suppression associated with methotrexate administration; immune suppression associated with chlorambucil administration; immune suppression associated with nitrogen mustard administration; immune suppression associated with 6-mercaptopurine administration; immune suppression associated with thioguanine administration; severe combined immunodeficiency; adenosine deaminase deficiency; major histocompatibility class I (Bare leukocyte syndrome) and class II deficiencies; purine nucleoside phosphorylase deficiency; DiGeorge Syndrome; transient hypogammaglobulinemia of infancy; X-linked agammaglobulinemia; X-linked agammaglobulinemia with growth hormone deficiency; transcobalamin II deficiency; immunodeficiency with thymoma; immunodeficiency with hereditary defective response to Epstein Barr virus; immunoglobulin deficiency with increased IgM; P chain deficiency; ataxia telangiectasia; immunodeficiency with partial albinism; sequelae of selective IgA deficiency such as those due to rheumatoid arthritis; juvenile rheumatoid arthritis; systemic lupus erythematosus; thyroiditis; pernicious anemia; dermatomyositis; Coomb's positive hemolytic anemia; idiopathic Addison's disease; cerebral vasculitis and idiopathic thrombocytopenic purpura.

In some embodiments, compositions and methods of the present invention provide anti-inflammatory benefits when administered to a subject. Pooled immunoglobulins have been shown to provide an anti-inflammatory action when passively administered (See, e.g., Nimmerjahn and Ravetch, Annu. Rev. Immunol. 2008. 26:513-33.; Ramakrishna et al. Plos Pathogens. 2011. 7:6:e1002071.; herein incorporated by reference in their entireties). In some embodiments, anti-pneumococcal hyperimmune globulin of the invention exerts enhanced anti-inflammatory effect (e.g., 10% enhancement, 20% enhancement, 50% enhancement, 2-fold enhancement 3-fold enhancement, 5-fold enhancement, 10-fold enhancement, or greater) compared to the anti-inflammatory effect of a mixture of plasma samples obtained from random human subjects (e.g., 1000 or more random human subjects). Although an understanding of a mechanism is not necessary to practice the present invention and while the present invention is not limited to any particular mechanism, in one embodiment, anti-pneumococcal hyperimmune globulin of the invention displays significantly enhanced anti-inflammatory effect compared to a conventional IVIG because the pooled plasma composition of the invention comprises plasma from at least 1000 donors (e.g., compared to a conventional hyperimmune globulin prepared from a limited number of donors (e.g., in one embodiment, the larger the number of different plasma samples pooled, the more beneficial the anti-inflammatory effect (e.g., the greater the histopathological benefit (e.g., reduction of epithelial cell death)) observed)).

In some embodiments of the present invention, compositions of the invention are administered alone, while in other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

In one embodiment, anti-pneumococcal hyperimmune globulin provided herein further comprises one or more biologically active agents. The invention is not limited to the type of biologically active agent/material. Indeed, a variety of biologically active agents/materials may be used including, but not limited to, antibodies, anti-toxin material, anti-inflammatory agent, anti-cancer agent, antimicrobial agent, therapeutic agent, antihistamine, cytokine, chemokine, vitamin, mineral, or the like. In one embodiment, the biologically active agent is an anti-toxin agent. In one embodiment, the anti-toxin agent is a mono-specific, bi-specific or multi-specific antibody with specificity toward a viral, bacterial or fungal toxin. In a further embodiment, the bacterial or fungal toxin is selected from *Botulinum* neurotoxin, Tetanus toxin, *E. coli* toxin, *Clostridium difficile* toxin, Vibrio RTX toxin, Staphylococcal toxins, Cyanobacteria toxin, and mycotoxins. In another embodiment, the immunotherapeutic composition further comprises an aliquot of a single or multiple monoclonal antibodies with a single or multiple specificities (e.g., the immunogenic composition may be spiked with one or more antibodies or biologically active material (e.g., a monoclonal antibody of any specificity, an anti-toxin agent, etc.)). The invention is not limited by the type of one or more antibodies that are added to (e.g., spiked into) the immunogenic composition. Indeed, any one or more antibodies (e.g., specific for a pathogen or pathogen product) may be used including, but not limited to standard antibodies, bi-specific antibodies, multi-specific antibodies, or the like known in the art (e.g., specific for one or a multiplicity of antigens).

The invention is not limited by the type of subject treated with the compositions and methods of the invention. Indeed, a variety of subjects may be so treated, including, but not limited to, a subject at risk of developing an infection (e.g., upper respiratory tract or other type of infection (e.g., thereby reducing the risk of developing infection in a subject having an elevated risk of infection)). In one embodiment, a subject treated with a composition of the invention has or is diagnosed as having a primary immunodeficiency disease (PIDD). In another embodiment, the subject is an end stage renal disease (ESRD) patient; cancer patient on immunosuppressive therapy, AIDS patient, diabetic patient, neonate, transplant patient, patient on immunosuppression therapy, patient with PIDD and other immune deficiencies, patient with malfunctioning immune system, autoimmune disease patient, an elderly person in an extended care facility, patient with autoimmune disease on immunosuppressive therapy, transplant patient, patient with invasive surgical procedure, burn patient, or other patient in acute care setting.

EXPERIMENTAL

The following examples are provided in order to demonstrate and further illustrate certain preferred embodiments and aspects of the present invention and are not to be construed as limiting the scope thereof.

Example 1

Generation of Hyperimmune Plasma Donors, Hyperimmune Serum and Immune Globulin Prepared From Same Experiments were conducted during development of embodiments of the invention in an effort to generate hyperimmune plasma donors possessing hyperimmune plasma/sera for a wide variety of pneumococcal serotypes. A non-limiting example of these experiments is provided below.

Healthy human (male and female) subjects between the ages of 18-45 were selected for immunization. In particular, each subject was required to be devoid of any known medical condition in order to participate in the study and to function as a vaccinated human plasma donor.

Each study participant was administered the following vaccination regimen: primary vaccination/dose of PREVNAR (PCV13) (0.5 mL intramuscular injection according to manufacturer's instructions) at day 0 followed by a secondary vaccination of PNEUMOVAX23 (0.5 mL intramuscular injection according to manufacturer's instructions) at 4 weeks. Blood was drawn (10 mL) from each participant at the following time points: immediately prior to primary PREVNAR vaccination, immediately prior to secondary PNEUMOVAX23 vaccination at week 4, at week 8, at week 10, at week 12 and at week 16. Serum samples were prepared from each blood sample, aliquoted, and stored at $-70°C.\pm10°$ C. Various studies (e.g., described below) were carried out with the serum samples.

Quantification of serotype specific anti-pneumococcal polysaccharide (PS) antibodies (IgG Testing). Pneumococcal serotype (ST) specific IgG was quantified adopting previously described methods (See, e.g., Lai et al., 2005 J Immunolo Meth 296:135-147). Briefly, spectrally distinct luminex beads were conjugated to pneumococcal (Pnc) ST specific capsular polysaccharide (PS) obtained from ATCC. Test serum samples were co-mixed with the PS conjugated beads and the ST specific IgG was quantified with the human reference serum, 89SF. The serotype specific concentration in the serum samples were expressed as μg/mL.

Opsonophagocytic Killing Assay (OPK) The functional antibody concentrations (titer) in the serum samples was tested adopting previously described methods (See, e.g., Romero-Steiner et al., 1997 Clin Diagn Lab Immunol. Jul;4(4): 415-22.). Briefly, HL-60 cells (Human promyelocytic leukocytes) differentiated into polymorphonuclear (PMN) lineage were used as effector cells. Live *S. pneumonia* serotype specific strains were used as the target and baby rabbit complement (PELFREEZE, Inc, Rogers, AR) was used as the complement source for opsonophagocytic killing. Reagents stored at 4±2° C. were brought to room temperature prior to performing the assay. 10 μL of HBSS (+) with Gelatin, hereafter known as assay buffer, was added to each well of a 96 well plate, except for row A. 20 μL of undiluted quality control sera was added to wells A1 through A3. 20 µL of diluted sample material was added to wells A4-A12. The QC sera and unknown samples were serially diluted 1:2. The complement control wells and cell control wells have 10 µL of assay buffer at this point.

A working *S. pneumonia* bacterial suspension was diluted to a concentration of 8.0×105 colonies per 20 µL. 20 µL of the bacterial suspension was added to each well of the plate, including control wells. The plate incubated for 30 minutes at room temperature on a plate shaker set to 200 rpm. 10 µL of frozen baby rabbit complement was added to every well except the cell control. The cell control received 10 µL of assay buffer in its place. The plate incubated for 15 minutes at room temperature on a plate shaker set to 200 rpm. 40 µL of differentiated HL60 PMNs were added to every well on the plate. The concentration of cells was determined so that 100,000 cells were added per well. The plate incubated for 30 minutes at room temperature on a plate shaker set to 200 rpm.

Using a multichannel pipet, 5 µL from each well in a row was simultaneously added to a 150×15 mm petri dish containing Chocolate Agar. The dish was angled to allow the sample volume to run down the agar plate in parallel rows. The dishes were incubated overnight at 37° C. and 5% CO2. The next day, plates were photographed and colony forming units (CFUs) counted. Bacterial killing was calculated as the percent kill within a well (CFU per well/average complement control CFU*100). The reciprocal of dilution that has >50% killing of the target bacterium compared to the complement control was reported as the OPK titer. Since the first dilution was 1:8, serum samples with no titers were reported 1:4 for computational purposes.

Example 2

Identification and Characterization of Pneumococcal Serotype Specific Total and Functional Antibody Response in Immunized Individuals Individual serum sample were drawn at different time points (immediately prior to primary PREVNAR vaccination, immediately prior to secondary PNEUMOVAX23 vaccination at week 4, at week 8, at week 10, at week 12 and at week 16) from study participants. The serum were analyzed for pneumococcal (Pnc) serotype (ST) specific IgG concentration (See IgG testing in Example 1, above). In addition to the individual serum samples, pooled serum was generated by pooling an equal amount of sera from each participant pre-and post-week 12 and the pooled serum samples were also characterized to assess the effect of pooling on the IgG testing outcome. Additionally, both the individual and pooled serum samples were tested for functional antibody response utilizing the opsonophagocytic killing assay (OPK) described in Example 1.

Pneumococcal serotype specific IgG concentrations/titer. Serum samples from each individual (n=10) prime-boost immunized with PREVNAR-PNEUMOVAX23 was analyzed for Pnc ST specific IgG. The Pnc ST specific IgG titers are shown in FIG. 1. Inter-donor and -ST variations were recorded for IgG response in the serum samples. While 9/10 donors were seen to mount a robust IgG response to Pnc STs, there exist differences in ST specific responses. Among the donors, 7/10 had peak IgG concentrations at 4 weeks post PNEUMOVAX23 vaccination (PNEUMOVAX23 boost response, eight weeks after prime vaccination) followed by a gradual drop that remained several fold above the baseline even at week 12. Despite these variations, all donors demonstrated Pnc ST specific IgG concentrations above protective level (>0.2 µg/mL) of immunity (See, e.g., Balmer et al., Clin Exp Immunol. 2003 September;133(3): 364-9). IgG concentration in the pooled sera indicated 2.2-30 fold increase in IgG concentrations at the end of the study period (week 12) from the baseline (pre). Among these, maximum increase in IgG response was recorded for serotype ST 1 followed by serotypes ST23F, and ST 4. Serotype ST19A exhibited the least fold increase in IgG concentration (2.2 fold) followed by ST 3 (2.6 fold) and ST14 (3.2 fold).

Functional/opsonic antibody titer (OPK). FIG. 2 shows data pertaining to the OPK titer in the donor sera specific to various Pnc STs. Baseline OPK titers tag along the IgG concentration. The fold increase in functional antibody titer ranged from 4-256 fold (See FIG. 2). Surprisingly, it was discovered that the total amount of IgG (e.g., shown in FIG. 1) was not correlated with the amount of total functional, opsonic antibody. For example, serotype ST14 had only a modest increase in total IgG titer (3.2 fold, See FIG. 1). However, it had the highest increase in functional response (opsonic antibody titer) of 256 fold over baseline.

Example 3

Quantification of Total and Functional Pneumococcal Serotype Antibodies in Pooled Human Sera Vaccinated human plasma donor (n=34) serum samples were drawn at one month intervals from between 1 month pre-vaccination-to month 5 post vaccination. At these 6 time points, serum samples were pooled and analyzed for Pnc ST specific IgG concentration (IgG testing) and functional antibodies using OPK described in Example 1 above. Antibody concentrations (serotype specific IgG and OPK) and fold increase over pre-vaccination baseline was determined.

Serum samples from individuals vaccinated (prime-boost immunized with PREVNAR-PNEUMOVAX23) were pooled at each 1 month interval from between 1 month pre-vaccination-to month 5 post vaccination and the pooled serum from each time point was analyzed for Pnc ST specific IgG. The Pnc ST specific IgG titer in the pooled donor sera drawn at each time point is shown in FIG. 3. The average IgG concentration in the post immune pooled sera ranged from 4.4-37.59 µg/mL. The reduction in overall IgG concentrations compared to week 12 end point was possibly due to a gradual drop in IgG levels after the spike observed at week 4 post boost vaccination resulting in the reduction of IgG concentration over time. Nevertheless, the fold increase in IgG concentration over the baseline (See FIG. 4) indicated a similar pattern as to that shown in FIG. 1 with the higher response to ST1, ST23F, and ST4.

OPK. The OPK titers in the pooled donor sera specific to various Pnc STs is shown in FIG. 5. Average post immunization OPK titer for ST1 was exceptionally high (36044) while all other STs had a minimum of a log lower titer. Even though high OPK titers were recorded in the individual serum samples tested at week 12 (See FIG. 2) the titers were not a log higher than the other serotypes.

Example 4

Identification and Characterization of Total and Functional Pneumococcal Serotype Antibodies in Purified Human IgG Serum samples drawn at different time points from the study participants (n=34) was pooled at each of the individual time points (pre, week 4, 8, 10, 12, 16, and month 5) and IgG was purified from the pooled samples using standard protein A immunosorbent columns. The purified IgG was analyzed for Pnc ST specific IgG concentration (IgG testing) and functional antibodies using OPK as described in Example 1. Antibody concentrations (serotype specific IgG) and functional antibody titer (OPK) were characterized. Additionally, characterization of the results were carried out in order to understand the relationship between the in vitro and ex vivo techniques based on regression analysis of the individual outcomes.

Pneumococcal serotype specific IgG concentrations. Serum samples from individuals vaccinated with the prime-boost immunization regimen with PREVNAR-PNEU-MOVAX23 were pooled at one month intervals from 1 month pre-vaccination until 5 months post and the pooled serum from each time point and IgG purified. The pooled sera were analyzed for Pnc ST specific IgG. The Pnc ST specific IgG of the pooled sera is shown in FIG. 6. Average IgG concentration in the post immune pooled sera ranged from 3.2-23.3 µg/mL resulting in reduction of IgG concentration over time. Nevertheless, the fold increase in IgG concentration over the baseline (See FIG. 4) indicated similar pattern as shown in FIG. 1 with the higher response for ST1, ST23F and ST4.

OPK: The OPK titer in the pooled donor sera specific to various Pnc STs is presented in FIG. 7. Average post immunization OPK titer ranged from 213-5826.7 with highest titer for ST7F (5826.7) followed by ST23F (4778.7) and ST5 (4096).

Example 5

Comparison of the OPK Serotype Titer Present in Pooled Human Sera from Vaccinated Donors Versus the OPK Serotype Titer Present in Conventional, Commercially Available IVIG OPK Assay. The OPK assay described in Example 1 above was used. Briefly, reagents stored at 4±2° C. were brought to room temperature prior to performing the assay. 10 µL of HBSS (+) with Gelatin, hereafter known as assay buffer, was added to each well of a 96 well plate, except for row A. 20 µL of undiluted quality control sera was added to wells A1 through A3. 20 µL of diluted sample material was added to wells A4-A12. The QC sera and unknown samples were serially diluted 1:2. The complement control wells and cell control wells have 10 µL of assay buffer at this point.

A working *S. pneumonia* bacterial suspension was diluted to a concentration of 8.0×105 colonies per 20 µL. 20 µL of the bacterial suspension was added to each well of the plate, including control wells. The plate incubated for 30 minutes at room temperature on a plate shaker set to 200 rpm. 10 µL of frozen baby rabbit complement was added to every well except the cell control. The cell control received 10 µL of assay buffer in its place. The plate incubated for 15 minutes at room temperature on a plate shaker set to 200 rpm. 40 µL of differentiated HL60 PMNs were added to every well on the plate. The concentration of cells was determined so that 100,000 cells were added per well. The plate incubated for 30 minutes at room temperature on a plate shaker set to 200 rpm.

Using a multichannel pipet, 5 µL from each well in a row was simultaneously added to a 150×15 mm petri dish containing Chocolate Agar. The dish was angled to allow the sample volume to run down the agar plate in parallel rows. The dishes were incubated overnight at 37° C. and 5% CO2.

The next day, plates were photographed and colony forming units (CFUs) counted. Bacterial killing was calculated as the percent kill within a well (CFU per well/average complement control CFU*100).

FIG. 8 shows a comparison of the OPK serotype specific titer of functional/opsonic antibodies present in pooled human sera from vaccinated donors versus the OPK serotype specific titer of functional/opsonic antibodies present in nine random and different, conventional, commercially available IVIG. Each column represents a single, unique *S. pneumonia* serotype. Each row represents a unique sample. Samples A-I represent conventional, commercially available IVIG.

As shown in FIG. 8, a pronounced variability in the serotype specific opsonic titers was discovered in the commercial lots of IVIG . It was further discovered that a heightened titer to one serotype did not predict or correlate with a heightened titer to any of the other serotypes suggesting that the individual heightened response did not reflect a general enhanced immune response to *S pneumonia* but rather sporadic enhanced response(s) to very specific serotypes. In marked contrast, the opsonic antibody titers observed using the immune globulin from immunized donors were noted as enhanced to all serotypes without exception. Additionally, there was a 3-256 fold increase in the opsonic anti-pneumococcal antibody titer in the immune globulin from immunized donors compared to the commercial lots of immune globulin. Thus, in some embodiments, compositions and methods of the invention for generating compositions (e.g., blood, plasma, and/or immune globulin compositions) containing an elevated opsonic anti-pneumococcal antibody titer provides a homogeneous composition comprising opsonic anti-pneumococcal antibody titers specific to all multiple pneumococcal serotypes (e.g., 9, 10, 11, 12, 13, 14, 15 or more serotypes) and/or significantly elevated opsonic antibody titers compared to conventional, commercial immune globulin (e.g., that is 2×,3×, 4×, 5×, 6×, 7×, 8×, 9×, 10×, or more greater opsonic antibody titer).

What is claimed is:

1. A method of treating pneumococcal infection in a subject comprising administering to the subject a therapeutically effective amount of an immunotherapeutic composition comprising:
   A) immune globulin prepared from pooled plasma samples from healthy adult human plasma donors vaccinated with a primary and a secondary anti-pneumococcal vaccine, wherein the samples are screened for one or more pathogens, and wherein the pooled plasma contains opsonophagocytic antibody titers specific for at least 7 or more *S. pneumonia* serotypes selected from the group consisting of *S. pneumonia* serotypes 1, 2, 3, 4, 5, 6A, 6B, 7A, 7B, 7C, 7D, 7E, 7F, 8, 9A-9V, 12, 14, 18C, 19A-19F, 23A-23F, and 25, wherein the opsonophagocytic antibody titers specific for the 7 or more *S. pneumonia* serotypes are each at least 3-fold higher than the opsonophagocytic antibody titers specific for the 7 or more *S. pneumonia* serotypes present in a control sample, wherein the control sample is immune globulin prepared from plasma pooled from 500 or more random human plasma donors that have not been vaccinated with an anti-pneumococcal vaccine; and
   B) a pharmaceutically acceptable carrier.
2. The method of claim 1, wherein the samples are screened for the one or more pathogens prior to pooling.

3. The method of claim 1, wherein the samples are screened for the one or more pathogens after pooling of the samples.

4. The method of claim 1, wherein the treating pneumococcal infection comprises therapeutically treating the pneumococcal infection.

5. The method of claim 1, wherein the treating pneumococcal infection comprises prophylactically treating the pneumococcal infection.

6. The method of claim 1, wherein the samples are screened for the one or more pathogens using nucleic acid testing.

7. The method of claim 1, wherein the samples are screened for the one or more pathogens using a serological test.

8. The method of claim 1, wherein the immunotherapeutic composition is administered to the subject via intravenous administration.

9. The method of claim 1, wherein the immunotherapeutic composition further comprises neutralizing antibodies specific for one or more of *Corynebacterium diphtheria*, measles virus, polio virus, and *Haemophilus influenza.*

10. The method of claim 9, wherein the immunotherapeutic composition is used to treat infection caused by *S. pneumonia, Corynebacterium diphtheria*, measles virus, and/or polio virus.

11. The method of claim 1, wherein the pooled plasma contains opsonophagocytic antibody titers specific for at least 7 or more *S. pneumonia* serotypes selected from the group of *S. pneumonia* serotypes 1, 3, 4, 5, 6B, 7F, 9V, 14, 18C, 19A, 19F, and 23F.

12. The method of claim 11, wherein the pooled plasma contains opsonophagocytic antibody titers specific for at least 7 or more *S. pneumonia* serotypes selected from the group of *S. pneumonia* serotypes 1, 3, 4, 5, 6B, 7F, 9V, 14, 18C, 19A, 19F, and 23F, wherein the opsonophagocytic antibody titers specific for the 7 or more *S. pneumonia* serotypes are each at least 5-fold higher than the opsonophagocytic antibody titers specific for the 7 or more *S. pneumonia* serotypes present in the control sample.

13. The method of claim 1, wherein the pooled plasma contains opsonophagocytic antibody titers specific for at least 7 or more *S. pneumonia* serotypes selected from the group of *S. pneumonia* serotypes 1, 3, 4, 5, 6B, 7F, 9V, 14, 18C, 19A, 19F, and 23F, wherein the opsonophagocytic antibody titers specific for the 7 or more *S. pneumonia* serotypes are each at least 10-fold higher than the opsonophagocytic antibody titers specific for the 7 or more *S. pneumonia* serotypes present in the control sample.

14. The method of claim 1, wherein the immunotherapeutic composition further comprises a recombinant antibody, synthetic antibody, monoclonal antibody, polyclonal antibody, bi-specific antibody, or multi-specific antibody.

15. The method of claim 14, wherein the mono-specific, bi-specific or multi-specific antibody has specificity toward a bacterial or fungal toxin selected from the group consisting of *Botulinum* neurotoxin, Tetanus toxin, *E. coli* toxin, *Clostridium difficile* toxin, *Vibrio* RTX toxin, *Staphylococcal* toxins, *Cyanobacteria* toxin, and mycotoxins.

16. The method of claim 1, wherein the subject is selected from the group consisting of an end stage renal disease (ESRD) patient, a patient on immunosuppressive therapy, an AIDS patient, a diabetic patient, a neonate, a transplant patient, a patient with malfunctioning immune system, an elderly person, a patient with autoimmune disease, a burn patient, a cancer patient, and a patient in an acute care setting.

17. The method of claim 1, wherein the subject has a primary immunodeficiency disease.

18. The method of claim 1, wherein the method further comprises administrating one or more biologically active agents.

19. The method of claim 18, wherein the one or more biologically active agents is selected from the group consisting of antibodies, anti-toxin material, anti-inflammatory agents, anti-cancer agents, antimicrobial agents, therapeutic agents, antihistamines, cytokines, chemokines, and vitamins.

* * * * *